US009875256B2

(12) United States Patent
Takata et al.

(10) Patent No.: US 9,875,256 B2
(45) Date of Patent: Jan. 23, 2018

(54) CONTROL METHOD OF INFORMATION TERMINAL AND RECORDING MEDIUM

(71) Applicant: Panasonic Intellectual Property Management Co., Ltd., Osaka (JP)

(72) Inventors: Kazutoyo Takata, Fukui (JP); Kazuki Kozuka, Osaka (JP); Kenji Kondo, Fukui (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 64 days.

(21) Appl. No.: 15/011,136

(22) Filed: Jan. 29, 2016

(65) Prior Publication Data
US 2016/0247300 A1 Aug. 25, 2016

(30) Foreign Application Priority Data

Feb. 19, 2015 (JP) ................................. 2015-030361

(51) Int. Cl.
*G06K 9/00* (2006.01)
*G06F 17/30* (2006.01)
*G06F 19/00* (2011.01)

(52) U.S. Cl.
CPC ...... *G06F 17/30259* (2013.01); *G06F 19/321* (2013.01); *G06F 19/3443* (2013.01)

(58) Field of Classification Search
USPC .......... 382/131, 128, 100; 345/502; 705/2, 3
See application file for complete search history.

(56) References Cited

U.S. PATENT DOCUMENTS

| 7,930,193 | B2* | 4/2011 | Marx | G06F 19/321 |
| | | | | 705/2 |
| 8,213,699 | B2* | 7/2012 | Wakai | G06F 19/321 |
| | | | | 382/131 |
| 8,238,624 | B2* | 8/2012 | Doi | G06T 1/00 |
| | | | | 345/502 |
| 8,447,090 | B2* | 5/2013 | Wakai | G06F 19/321 |
| | | | | 382/131 |

(Continued)

FOREIGN PATENT DOCUMENTS

| JP | 2005-065728 | 3/2005 |
| JP | 2005-160503 | 6/2005 |

(Continued)

OTHER PUBLICATIONS

Akira Oosawa et al., "Development of "Synapse Case Match", Content-based Image Retrieval System for Supporting Image Diagnosis", Fujifilm Research & Development (No. 58-2013).

*Primary Examiner* — Anh H Do
(74) *Attorney, Agent, or Firm* — Wenderoth, Lind & Ponack, L.L.P.

(57) ABSTRACT

A display window is displayed on a display of an information terminal, the display window including a first display area that displays similar medical images received from a case retrieval system and an instruction function that changes the display number of the similar medical images displayed in the first display area. If an instruction by the instruction function is detected, the display size of an individual area for displaying each of the similar medical images is changed while the display size of a sick portion of each of the similar medical images the same size, and hence the display number of the similar medical images displayed in the first display area is changed.

13 Claims, 51 Drawing Sheets

(56) References Cited

U.S. PATENT DOCUMENTS

| | | | |
|---|---|---|---|
| 9,168,007 B2 * | 10/2015 | Ozaki | ................ A61B 6/032 |
| 2008/0243395 A1 | 10/2008 | Oosawa et al. | |
| 2010/0232661 A1 | 9/2010 | Hisanaga et al. | |
| 2013/0184582 A1 | 7/2013 | Kanayama et al. | |

FOREIGN PATENT DOCUMENTS

| | | |
|---|---|---|
| JP | 2008-188177 | 8/2008 |
| JP | 2008-257292 | 10/2008 |
| JP | 2010-211749 | 9/2010 |
| JP | 2013-144050 | 7/2013 |
| JP | 2014-004252 | 1/2014 |

* cited by examiner

FIG. 8

| DISEASE NAME LIST | 730 | |
|---|---|---|
| MYCOSIS | 14 | 731 |
|   ASPERGILLOSIS | 8 | 732 |
|   CRYPTOCOCCOSIS | 6 | 733 |
| NEOPLASTIC | 13 | 734 |
|   LUNG CANCER | 10 | 735 |
|   METASTATIC LUNG CANCER | 3 | 736 |
| NONNEOPLASTIC | 6 | 737 |
|   LUNG ABSCESS | 4 | 738 |
|   SARCOIDOSIS | 1 | 739 |
|   SEPTIC EMBOLI | 1 | 740 |
| MYCOBACTERIOSIS | 6 | 741 |
|   NONTUBERCULOUS MYCOBACTERIA | 4 | 742 |
|   TUBERCULOSIS | 2 | 743 |
| OTHERS | 2 | 744 |
|   BRONCHIECTASIS | 1 | 745 |
|   ... | 1 | |

FIG. 11

SICK DISTRIBUTION ⌐750
☐ DIFFUSE ⌐751    ☐ MULTIPLE ⌐755
▨ SEGMENTAL ⌐752  ▨ SUBPLEURAL ⌐756
☐ BRONCHIAL ⌐753  ☐ HEMATOGENOUS ⌐757
☐ BILATERAL ⌐754

FIG. 12

SICK DISTRIBUTION ⌐750
☐ DIFFUSE ⌐751    ☐ MULTIPLE ⌐755
▨ SEGMENTAL ⌐752  ▨ SUBPLEURAL ⌐756
☑ BRONCHIAL ⌐753  ☐ HEMATOGENOUS ⌐757
☐ BILATERAL ⌐754

FIG. 14

SICK DISTRIBUTION  ⌐750
☑ DIFFUSE ⌐751   ☐ MULTIPLE ⌐755
▦ SEGMENTAL ⌐752   ▦ SUBPLEURAL ⌐756
☐ BRONCHIAL ⌐753   ☑ HEMATOGENOUS ⌐757
☐ BILATERAL ⌐754

| | | |
|---|---|---|
| 1100 | PATIENT ID | 123456 |
| 1200 | NAME | PANA TARO |
| 1300 | AGE | 28 |
| 1400 | SEX | MALE |
| 1500 | MEDICAL HISTORY | NONE |
| 1600 | FAMILY MEDICAL HISTORY | NONE |
| 17001 | CHIEF COMPLAINT | COUGH |
| 1800 | INSPECTION INFORMATION | (SEE FIG. 17) |
| 1900 | DEFINITE DIAGNOSIS | MYCOPLASMA PNEUMONIA |

| | | |
|---|---|---|
| 1810 → | INSPECTION ID | 13227895 |
| 1820 → | INSPECTION DATE | 2/5/20XX 10:00 |
| 1830 → | INSPECTION TYPE | BLOOD TEST |
| 1840 → | INSPECTION RESULT | YYYY1 |

| | |
|---|---|
| INSPECTION ID | 13227903 |
| INSPECTION DATE | 2/5/20XX 11:00 |
| INSPECTION TYPE | PLAIN X-RAY (CHEST) |
| INSPECTION RESULT | YYYY2 |

| | |
|---|---|
| INSPECTION ID | 13227989 |
| INSPECTION DATE | 2/9/20XX 9:00 |
| INSPECTION TYPE | CT (CHEST) |
| INSPECTION RESULT | YYYY3 |

| INSPECTION ID | 13227989 |
|---|---|
| REMARK | MULTIPLE NODULES WITH SIZES OF 0.5 TO 1 cm IN RIGHT LUNG FIELD ... |
| DIAGNOSIS | INFLAMMATORY NODULE OR TUBERCULOSIS IS SUSPECTED. |

1810 — INSPECTION ID
3100 — REMARK
3200 — DIAGNOSIS

FIG. 23

| PATIENT ID | PATIENT NAME | INSPECTION DATE | INSPECTION ID | INSPECTION TYPE |
|---|---|---|---|---|
| 443982 | YAMADA ICHIRO | 12/1/20XX | 23982874 | MR (HEAD) |
| 123456 | PANA TARO | 5/8/20XX | 13227989 | CT (CHEST) |
| 345455 | ... | ... | ... | ... |
| 235982 | ... | ... | ... | ... |

| SERIES ID | DEFINITION | IMAGE |
|---|---|---|
|  |  |  |
|  |  |  |
|  |  |  |

FIG. 24

| PATIENT ID | PATIENT NAME | INSPECTION DATE | INSPECTION ID | INSPECTION TYPE |
|---|---|---|---|---|
| 443982 | YAMADA ICHIRO | 12/1/20XX | 23982874 | MR (HEAD) |
| 123456 | PANA TARO | 5/8/20XX | 13227989 | CT (CHEST) |
| 345455 | ... | ... | ... | ... |
| 235982 | ... | ... | ... | ... |

| SERIES ID | DEFINITION | IMAGE |
|---|---|---|
| CT152729 | LUNG WINDOW<br>SLICE THICKNESS: 5 mm | |
| CT152730 | LUNG WINDOW<br>SLICE THICKNESS: 1 mm | |
| CT152731 | MEDIASTINAL WINDOW<br>SLICE THICKNESS: 5 mm | |

FIG. 29

| DISEASE NAME ID | BROAD CATEGORY DISEASE NAME | DETAILED CATEGORY DISEASE NAME | NUMBER OF CASES | SIMILAR CASE ID |
|---|---|---|---|---|
| DIS528 | NEOPLASTIC | LUNG CANCER | 10 | SIM258, SIM551, SIM1209, SIM2341, ... |
| DIS922 | MYCOSIS | ASPERGILLOSIS | 8 | ... |
| ... | MYCOSIS | CRYPTOCOCCOSIS | 6 | ... |
| ... | NONNEOPLASTIC | LUNG ABSCESS | 4 | ... |
| ... | MYCOBACTERIOSIS | NONTUBERCULOUS MYCOBACTERIA | 4 | ... |
| ... | ... | ... | ... | ... |

FIG. 30

DISEASE NAME LIST 730

| | |
|---|---|
| LUNG CANCER | 10 |
| ASPERGILLOSIS | 8 |
| CRYPTOCOCCOSIS | 6 |
| LUNG ABSCESS | 4 |
| NONTUBERCULOUS MYCOBACTERIA | 4 |
| METASTATIC LUNG CANCER | 3 |
| TUBERCULOSIS | 2 |
| INFLAMMATORY NODULE | 1 |
| SEPTIC EMBOLI | 1 |
| BRONCHIECTASIS | 1 |
| UNKNOWN | 1 |

FIG. 31

DISEASE NAME LIST 730

| | |
|---|---|
| MYCOSIS | 14 |
| NEOPLASTIC | 13 |
| NONNEOPLASTIC | 6 |
| MYCOBACTERIOSIS | 6 |
| OTHERS | 2 |

FIG. 32

| DISEASE NAME LIST | 730 |
|---|---|
| MYCOSIS | 14 |
|   ASPERGILLOSIS | 8 |
|   CRYPTOCOCCOSIS | 6 |
| NEOPLASTIC | 13 |
|   LUNG CANCER | 10 |
|   METASTATIC LUNG CANCER | 3 |
| NONNEOPLASTIC | 6 |
|   LUNG ABSCESS | 4 |
|   SARCOIDOSIS | 1 |
|   SEPTIC EMBOLI | 1 |
| MYCOBACTERIOSIS | 6 |
|   NONTUBERCULOUS MYCOBACTERIA | 4 |
|   TUBERCULOSIS | 2 |
| OTHERS | 2 |
|   BRONCHIECTASIS | 1 |
|   ... | 1 |

FIG. 34

| DISTRIBUTION NAME | NUMBER OF CASES | SIMILAR CASE ID |
|---|---|---|
| DIFFUSE | 3 | SIM2521, SIM4123, SIM5225 |
| SEGMENTAL | 0 | NONE |
| BRONCHIAL | 2 | SIM0006, SIM1892, SIM4399 |
| BILATERAL | 12 | ... |
| MULTIPLE | 22 | ... |
| SUBPLEURAL | 0 | NONE |
| HEMATOGENOUS | 5 | ... |

| NUMBER OF ROWS | 2 |
|---|---|
| NUMBER OF COLUMNS | 2 |

~4411

| POSITION | SLICE ID |
|---|---|
| 1ST ROW AND 1ST COLUMN | CT12353515_1 |
| 1ST ROW AND 2ND COLUMN | — |
| 2ND ROW AND 1ST COLUMN | — |
| 2ND ROW AND 2ND COLUMN | — |

~4412

CONTROL METHOD OF INFORMATION TERMINAL AND RECORDING MEDIUM

BACKGROUND

1. Technical Field

The present disclosure relates to a control method of an information terminal for retrieving a similar medical image similar to a target medical image for reading, and also relates to a recording medium.

2. Description of the Related Art

In recent years, for example, medical imaging apparatuses of computed tomography (CT), magnetic resonance imaging (MRI), etc., are being developed and widely used. CT or MRI provides digitalized and highly precise medical images by a large volume. Also, medical images read by doctors with reading reports are gradually increasingly stored in picture archiving and communication systems (PACS). For example, as disclosed in Japanese Unexamined Patent Application Publication No. 2008-257292, there is gradually developed a technique of retrieving a past medical image similar to a target medical image for reading from past cases stored in PACS for reference in new reading.

SUMMARY

However, further improvement has been required.

In one general aspect, the techniques disclosed here feature a control method of an information terminal connected to a case retrieval system that retrieves a medical image by referencing a medical image database in which the medical image is registered, the information terminal including a display, the method including: having a computer of the information terminal receive a number NC, being 2 or larger, of similar medical images each having predetermined similarity to a target medical image, being a target medical image for reading, from the case retrieval system, each of the number NC of the similar medical images including sick portion information indicative of a sick portion in the similar medical image; having the display show a display window including a first display area including a number M, being in a range from 1 to the number NC, of individual areas displaying the number M of the similar medical images included in the number NC of the similar medical images, and an instruction function to change a display number of the similar medical images included in the number M of the similar medical images displayed in the first display area; and if an instruction by the instruction function is detected, changing a display size of each of the individual areas while keeping a display size of the sick portion of each of the similar medical images a same size, and hence changing the display number of the similar medical images included in the number M of the similar medical images displayed in the first display area.

With the aspect, further improvement can be provided.

It should be noted that general or specific embodiments may be implemented as a system, a method, an integrated circuit, a computer program, a storage medium, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 8 is an enlarged view of a disease name list display area;

FIG. 11 is an enlarged view of a distribution list display area;

FIG. 12 illustrates the distribution list display area with a checkmark input;

FIG. 14 illustrates the distribution list display area when a plurality of checkmarks are input;

FIG. 16 illustrates a data configuration of patient information;

FIG. 17 illustrates a data configuration of inspection information registered in the patient information shown in FIG. 16;

FIG. 19 illustrates a data configuration of a diagnosis report;

FIG. 23 is a window view of an inspection list;

FIG. 24 is a window view of an inspection list after an inspection is selected;

FIG. 29 illustrates a data configuration of a disease name list generated in S2703 in FIG. 27;

FIG. 30 illustrates a first display example of a disease name list display area;

FIG. 31 illustrates a second display example of a disease name list display area;

FIG. 32 illustrates a third display example of a disease name list display area;

FIG. 34 illustrates a data configuration of a distribution list generated in S2704 in FIG. 27;

FIG. 35 illustrates a data configuration of display box management information;

DETAILED DESCRIPTION

Figure 1:
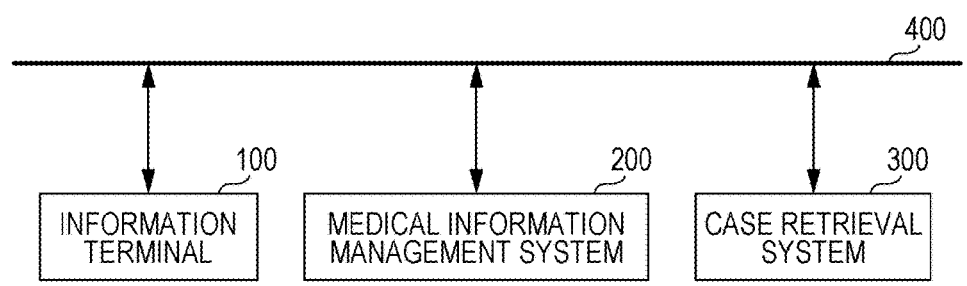
FIG. 1 is a general configuration diagram of a hospital information system with an information terminal according to an embodiment applied.

Underlying Knowledge Forming Basis of the Present Disclosure

Focusing points of an aspect according to the present disclosure are described first.

Japanese Unexamined Patent Application Publication No. 2008-257292 (hereinafter, referred to as document '292) discloses an image diagnosis support apparatus that presents case images useful for determining a disease or statistical information etc. relating to the disease in image diagnosis based on a diagnosis target image. A window for retrieval results by the image diagnosis support apparatus displays a diagnosis target image and information on representative cases on a disease basis. To be specific, the window for the retrieval results displays i) images of representative cases of top 3 diseases A, D, and G, ii) similarity to a diagnosis target image on a disease basis, the number of registered cases, and the number of representative cases, iii) the number of retrievals (the total number of retrieved diseases), and iv) a software button of "next page" for referencing information of other diseases which cannot be displayed in one window (see paragraphs [0062] to [0063], and FIG. 6(E)).

However, the document '292 does not describe enlarging the images of the representative cases in the window for the retrieval results. Therefore, the document '292 does not even disclose simply enlarging the images of the representative cases, or an idea of, for example, enlarging each of the images of the representative cases about a sick portion included in the images of the representative cases in the window for the retrieval results with limitation on the number of displayed images.

Japanese Unexamined Patent Application Publication No. 2014-4252 (hereinafter, referred to as document '252) discloses a medical image display device that improves comparative image reading efficiency for medical images of the same patient. In this case, the comparative image reading represents i) comparative image reading with use of image data obtained by different image diagnosis devices or under different imaging conditions from the same patient, or ii) comparative image reading with use of past and latest image data obtained by the same image diagnosis device from the same patient. That is, the comparative image reading in the document '252 is comparative image reading with use of image data from the same patient. A display window of the medical image display device displays 3 types of software buttons including "standard," "magnification basis," and "size basis" for enlarging or reducing thumbnail images displayed in a thumbnail display area (see paragraph [0040] and FIG. 6). When "magnification basis" or "size basis" is selected, the thumbnail images are displayed in an enlarged manner to include sick ranges or sick positions. Accordingly, checking a sick portion with the thumbnail images displayed in a list is easier than a case when "standard" is selected. Also, if "size basis" is selected, the thumbnail size of the thumbnail images is the same as the size in the case when "standard" is selected to keep viewability (see paragraphs [0041] to [0043] and FIG. 7). In the document '252, the thumbnail images are displayed in the order in a time series (for example, see FIG. 6 in the document '252).

However, in the document '252, if "magnification basis" or "size basis" is selected, all the thumbnail images including the sick ranges or the sick positions are enlarged. That is, in addition to the thumbnail images displayed in the thumbnail display area, hidden thumbnail images not displayed in the thumbnail display area are enlarged (for example, see FIGS. 6 and 7 in the document '252). This is to compare images of the same patient with time (comparative image reading). Since comparative image reading is performed mainly for follow-up, medical images are typically captured every half year or every year. Owing to this, the number of medical images is less possibly large, and hence even if all the thumbnail images are enlarged, the processing load on the system is not markedly increased. Also, since the thumbnail images are images of the same patient, it is not required to check whether or not the thumbnail images are similar to each other unlike a case in which a target image for reading is compared with an image of another patient. That is, the thumbnail images in the document '252 are used for studying a change in the sick portion of the same patient in a time series. Owing to this, when images are enlarged, it is not required to enlarge some thumbnail images based on similarity to an image of another patient while not enlarging the other thumbnail images.

OOSAWA Akira and 4 others, "Development of 'SYNAPS Case Match,' Content-based Image Retrieval System for Supporting Image Diagnosis," FUJIFILM Research & Development, FUJIFILM Corporation, Mar. 27, 2013, No. 58, pp. 11 to 14 (hereinafter, referred to as report) discloses a similar case retrieval system for supporting image diagnosis by a doctor by instantly extracting and presenting proper information from clinical knowledge stored in the aforementioned PACS or other system by a function of retrieving past similar cases with use of an image of a sick portion. To be specific, this system retrieves a plurality of case images having similar sick features in inspection images and displays the case images in the order of similarity. Then, a reference case image is selected from the plurality of displayed case images, and is displayed next to an inspection image (see p. 12, "2.2 Advantages of This System" and FIG. 3).

However, for the system disclosed in the aforementioned report, enlarging the plurality of case images displayed in the order of similarity is not described. Therefore, the report does not even disclose simply enlarging the case images, or an idea of, for example, enlarging each of the images of the representative cases about a sick portion included in the images of the representative cases in the window for the retrieval results with limitation on the number of displayed images.

To study about a sick portion appearing in a target medial image for reading, the disease name of which is not specified yet, it is effective to reference a similar medical image similar to the target medical image for reading in other medical images, the disease names of which are already specified. However, if such a system is constructed, a markedly large number of medical images are registered in the medical image database. Even in this case, it is desirable to effectively present a similar medical image useful for diagnosis on the target medical image for reading to a doctor.

With the above-described consideration, the inventors have conceived respective aspects described below.

According to an aspect of the present disclosure, there is provided a control method of an information terminal connected to a case retrieval system that retrieves a medical image by referencing a medical image database in which the medical image is registered, the information terminal including a display, the method including:

having a computer of the information terminal receive a number NC, being 2 or larger, of similar medical images each having predetermined similarity to a target medical image, being a target medical image for reading, from the case retrieval system, each of the number NC of the similar medical images including sick portion information indicative of a sick portion in the similar medical image;

having the display show a display window including a first display area including a number M, being in a range from 1 to the number NC, of individual areas displaying the number M of the similar medical images included in the number NC of the similar medical images, and an instruction function to change a display number of the similar medical images included in the number M of the similar medical images displayed in the first display area; and if an instruction by the instruction function is detected, changing a display size of each of the individual areas while keeping a display size of the sick portion of each of the similar medical images a same size, and hence changing the display number of the similar medical images included in the number M of the similar medical images displayed in the first display area.

With the aspect, the number NC of the similar medical images each having the predetermined similarity to the target medical image is received from the case retrieval system, and the number M of the similar medical images included in the number NC of the similar medical images are displayed in the display. Accordingly, a similar medical image, which is referenced when a disease name of a sick portion appearing in the target medical image is studied, can be efficiently extracted from a large number of medical images registered in the medical image database and can be presented to a doctor. The similar medical image, which is referenced in diagnosis on the target medical image for reading, can be effectively presented to the doctor.

Also, with the aspect, the display number of the similar medical images included in the number M of the similar medical images displayed in the first display area can be changed. At this time, by changing the display size of each of the individual areas included in the first display area while keeping the display size of the sick portion of each of the similar medical images the same size, the display number of the similar medical images included in the number M of the similar medical images displayed in the first display area can be changed. That is, the doctor can desirably change the display number of the similar medical images displayed in the first display area. Consequently, viewability in a retrieval result window of the case retrieval system can be improved. This can make contribute to improvement in diagnosis accuracy.

Also, in the aspect, the display size of the sick portion is kept the same size because the area that the doctor is interested in similar case retrieval is a sick portion of each similar medical image. That is, the doctor makes diagnosis on whether or not a similar medical image is similar to a target medical image mainly for a sick portion of the similar medical image. Owing to this, to keep the display size of the sick portion of each similar medical image the same size is to keep information required for diagnosis without deteriorated. Further, to keep the display size of the sick portion the same size may be advantageous in view of diagnosis as compared with a case in which the display size of the sick portion is increased. That is, since the display size of the sick portion is kept the same size, even after the display size of each individual area is changed, the doctor can easily recognize the area of the sick portion of each similar medical image. If the display size of the sick portion is increased, the area of the sick portion of each similar medical image may not be easily recognized merely by watching the similar medical image displayed in the first display area. Then, when the doctor compares the target medical image with each similar medical image, the doctor may not easily determine whether or not the area of the sick portion is identical. Therefore, in this embodiment, the display size of the sick portion is kept the same size. The reason why the display size of each individual area is changed, that is, the reason why an area other than the sick portion is trimmed is that the area deleted by trimming is less important as information required for diagnosis as compared with the sick portion.

Hence, with this embodiment, information required for diagnosis can be properly presented to the doctor while viewability of the retrieval result window is improved. Consequently, this can contribute to improvement in diagnosis accuracy by a doctor.

Also, in the aspect, for example, if an instruction to increase the display number of the similar medical images by the instruction function is detected, the display size of each of the individual areas may be reduced while the display size of the sick portion of each of the similar medical images is kept the same size, and hence the display number of the similar medical images included in the number M of the similar medical images displayed in the first display area may be increased.

In this case, reducing the display size of each of the individual areas while keeping the display size of the sick portion of each of the similar medical images the same size corresponds to that the area other than the sick portion of each of the similar medical images is deleted by trimming. In other words, the display size of each individual area is reduced by the amount of the area deleted by trimming. Then, since the display size of each individual area is reduced, the display number of the similar medical images that are included in the number M of the similar medical images and that can be displayed in the first display area is increased. Consequently, the number NC of the similar medical images hidden from the first display area when the display size of each individual area is the original size can be displayed in the first display area.

Accordingly, with the aspect, since the number NC of the similar medical images can be displayed in the first display area, viewability of the retrieval result window of the case retrieval system can be improved.

Also, in the aspect, for example, the instruction function may be a scroll bar, and if movement of the scroll bar is detected, the display size of each of the individual areas may be changed while the display size of the sick portion of each of the similar medical images is kept the same size, and hence the display number of the similar medical images included in the number M of the similar medical images displayed in the first display area may be changed.

With this aspect, the display number of the similar medical images included in the number M of the similar medical images displayed in the first display area is increased in accordance with the movement of the scroll bar. Accordingly, the doctor can change the display number of the similar medical images included in the number M of the similar medical images displayed in the first display area by an easy operation. Accordingly, the load of operation of the doctor is decreased, the doctor can concentrate on specialized diagnosis by the amount of decreased load, and hence diagnosis accuracy can be increased.

Also, in the aspect, for example, if an instruction to increase the display number of the similar medical images by the scroll bar is detected, the display size of each of the individual areas may be reduced as a moving distance of the scroll bar is increased.

With this embodiment, the display number of the similar medical images included in the number M of the similar medical images displayed in the first display area is increased in accordance with the moving distance of the scroll bar. That is, the doctor can control the display number of the similar medical images included in the number M of the similar medical images displayed in the first display area, by a simple operation of adjusting the moving distance of the scroll bar. Accordingly, the load of operation of the doctor is decreased, the doctor can concentrate on specialized diagnosis by the amount of decreased load, and hence diagnosis accuracy can be increased.

Also, in the aspect, for example, the display sizes of the individual areas displayed in the first display area may be identical.

With the aspect, since the display sizes of the individual areas displayed in the first display area are identical, viewability is increased as compared with a case in which the display sizes of the individual areas are not uniform.

Also, in the aspect, for example, the target medical image and the similar medical images may be medical images captured by tomography, each of the similar medical images may include imaging condition information indicative of an imaging condition of the tomography, and the number M of the similar medical images may be classified by the imaging condition based on the imaging condition information and displayed in the first display area.

In this case, the imaging condition information includes, for example, one of a T1-weighted image and a T2-weighted image captured by magnetic resonance imaging. In the T1-weighted image, fat etc. appears white and blood etc. appears black. In contrast, in the T2-weighted image, fat, blood, etc. appear white and calcification etc. appears black. That is, a target appearing white is different depending on whether the image is the T1-weighted image or the T2-weighted image. Hence, when the number M of the similar medical images are displayed in the first display area, if the T1-weighted image or the T2-weighted image is displayed in a mixed manner, the doctor may be confused.

With this embodiment, the number M of the similar medical images are classified and displayed in the first display area by imaging condition. Accordingly, the doctor who performs diagnosis can recognize the imaging condition of each similar medical image at a glance, and the doctor can perform diagnosis without being confused. Further, since similar case determination can be held by imaging condition, diagnosis accuracy can be increased.

Also, in the aspect, for example, related similar medical images may be added to the similar medical images, the related similar medical images each having an imaging condition different from the imaging condition of each of the similar medical images for a same imaging target, and the similar medical images and the related similar medical images of the similar medical images may be classified in a same column direction or a same row direction by the imaging condition and displayed in the first display area.

In this case, when imaging is performed on a patient by magnetic resonance imaging, imaging may be performed under a plurality of imaging conditions in one-time imaging. That is, a plurality of medical images may be obtained in one-time imaging. If one of the plurality of obtained similar medical images serves as a similar medical image, the other similar medical images serve as related similar medical images. Information which cannot be obtained from the similar medical image can be obtained from the related similar medical images. This information is useful when similar cases of the target medical image are studied.

With the aspect, when the respective similar medical images displayed in the first display area are determined whether or not being similar to the target medical image, the study can be held also by using the related similar medical images. Accordingly, diagnosis accuracy can be increased.

Also, in the aspect, for example, when the number NC of the similar medical images received from the case retrieval system are displayed in the first display area, the display size of each of the individual areas may be changed while the display size of the sick portion of each of the similar medical images is kept the same size in accordance with a total number of imaging conditions included in the number NC of the received similar medical images, and the similar medical images and the related similar medical images of the similar medical images may be classified and displayed in the same column direction or the same row direction by the imaging condition.

With the aspect, the display size of each of the individual areas is automatically changed while the display size of the sick portion of each of the similar medical images is kept the same size in accordance with the total number of imaging conditions included in the number NC of the similar medical images received from the case retrieval system, and the similar medical images and the related similar medical images of are classified and displayed in the same column direction or the same row direction by the imaging condition. That is, in the window of initial retrieval results, the above-described display window is displayed without any operation by the doctor. Accordingly, the load of operation of the doctor is decreased, the doctor can concentrate on specialized diagnosis by the amount of decreased load, and hence diagnosis accuracy can be increased.

Also, in the aspect, for example, the control method may have the computer of the information terminal detect designation information indicative of a region of interest in the target medical image, transmit information indicative of a feature amount of the region of interest to the case retrieval system, and receive the feature amount of the region of interest and a similar medical image having the predetermined similarity from the case retrieval system.

Also, in the aspect, for example, the control method may have the computer of the information terminal detect designation information indicative of a region of interest in the target medical image, transmit the target medical image and the designation information to the case retrieval system, and receive a feature amount of the region of interest obtained from the target medical image and the designation information, and a similar medical image having the predetermined similarity from the case retrieval system.

According to another aspect, there is provided a non-transitory computer-readable recording medium including a program causing processing to be executed in an information terminal connected to a case retrieval system that retrieves a medical image by referencing a medical image database in which the medical image is registered, the information terminal including a display, in which the information terminal includes a processor, the recording medium is non-volatile, a computer of the information terminal can read data from the recording medium, and the processing has the computer receive a number NC, being 2 or larger, of similar medical images each having predetermined similarity to a target medical image, being a target medical image for reading, from the case retrieval system, each of the number NC of the similar medical images including sick portion information indicative of a sick portion in the similar medical image;

having the display show a display window including a first display area including a number M, being in a range from 1 to the number NC, of individual areas displaying the number M of the similar medical images included in the number NC of the similar medical images, and an instruction function to change a display number of the similar medical images included in the number M of the similar medical images displayed in the first display area; and if an instruction by the instruction function is detected, changing a display size of each of the individual areas while keeping a display size of a sick portion of each of the similar medical images a same size, and hence changing the display number of the similar medical images included in the number M of the similar medical images displayed in the first display area.

According to still another aspect, there is provided a control method, including:

having an information terminal receive first thumbnail images including second thumbnail images and third thumbnail images, each of the first thumbnail images including a sick portion, similar images each having predetermined similarity to a target medical image for reading, the similar images and the first thumbnail images being in a one-to-one relationship, each of the first thumbnail images being generated based on the corresponding similar image included in the similar images;

having a display show first images in a predetermined area, the first images and the second thumbnail images being in a one-to-one relationship, each of the first images being generated based on the corresponding thumbnail image included in the second thumbnail images;

receiving an instruction to increase a total number of images displayed in the predetermined area from a total number of the first images; and having the display show second images and third images in the predetermined area after receiving the instruction, in which the second images and the second thumbnail images are in a one-to-one relationship, and the third images and the third thumbnail images are in a one-to-one relationship, each of the second images is generated based on the corresponding thumbnail image included in the second thumbnail images, and each of the third images is generated based on the corresponding thumbnail image included in the third thumbnail images, and if a first image included in the first images and a second image included in the second images are generated based on a same thumbnail image included in the second thumbnail images, an area of the first image is bigger than an area of the second image, and an area of a sick portion included in the first image and an area of a sick portion included in the second image are identical.

Also, in the above aspect, for example, when the first images are displayed in the predetermined area, the predetermined area may be divided into areas, a total number of which is identical to the total number of the first images, and when the second images and the third images are displayed in the predetermined area, the predetermined area may be divided into areas, a total number of which is identical to a total number of the second images and the third images.

First Embodiment

An embodiment of the present disclosure is described below with reference to the drawings. In the drawings, the same reference sign is used for the same component.

FIG. 1 is a general configuration diagram of a hospital information system with an information terminal according to the embodiment applied. As shown in FIG. 1, the hospital information system includes an information terminal 100, a medical information management system 200, and a case retrieval system 300.

The information terminal 100, the medical information management system 200, and the case retrieval system 300 are connected to each other through a network 400 so that communication is allowed.

The medical information management system 200 and the case retrieval system 300 do not have to be arranged in a hospital, and may be software operable on, for example, a data center, a private cloud server, or a public cloud server outside the hospital. If the medical information management system 200 and the case retrieval system 300 are arranged in the hospital, the network 400 may employ a local area network. The local area network may employ wired LAN of IEEE802.3 series, wireless LAN of IEEE802.11 series, or a network with a combination of these. If the medical information management system 200 and the case retrieval system 300 are provided by using a server outside the hospital, the network 400 may employ the Internet.

The information terminal 100 may employ an information terminal, such as a personal computer or a tablet terminal. The medical information management system 200 may employ, for example, picture archiving and communication systems (PACS) or an electronic medical chart system.

Figure 2:
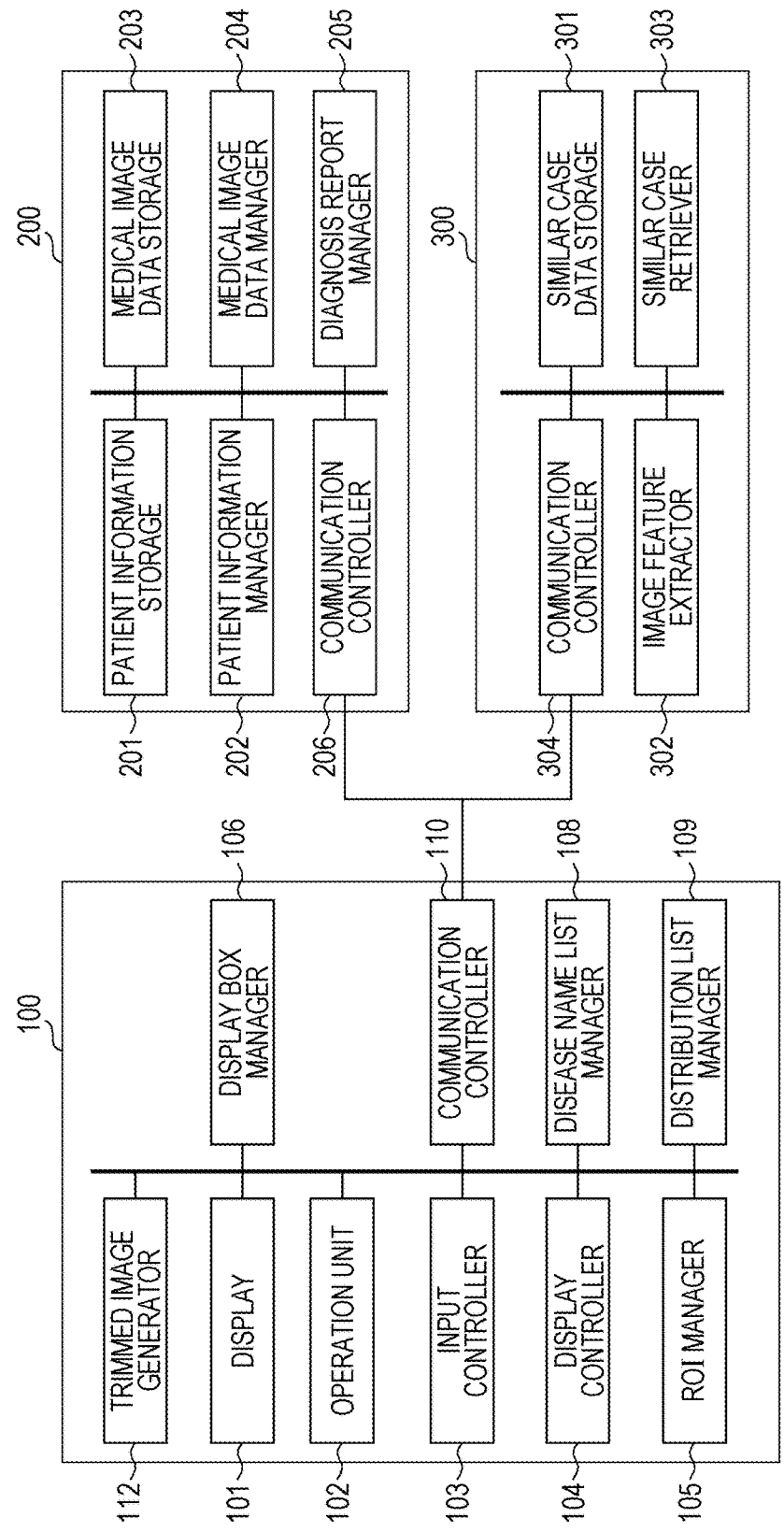
FIG. 2 is a block diagram showing configurations of the information terminal, a medical information management system, and a case retrieval system.

FIG. 2 is a block diagram showing configurations of the information terminal 100, the medical information management system 200, and the case retrieval system 300. As shown in FIG. 2, the information terminal 100 includes a display 101, an operation unit 102, an input controller 103, a display controller 104, a region of interest (ROI) manager 105, a display box manager 106, a disease name list manager 108, a distribution list manager 109, a communication controller 110, and a trimmed image generator 112.

The display 101 is formed of, for example, a liquid crystal monitor. The display 101 displays a medical image being a diagnosis target and a medical chart image, and a report input image for inputting a diagnosis result. At least one display 101 is required. In general, 2 to 3 displays 101 are used for image diagnosis. In this embodiment, 2 displays 101 are used. One of the displays 101 is called display 101a (an example of a second display) and the other display 101 is called display 101b (an example of a first display) (see FIG. 3).

Figure 3:
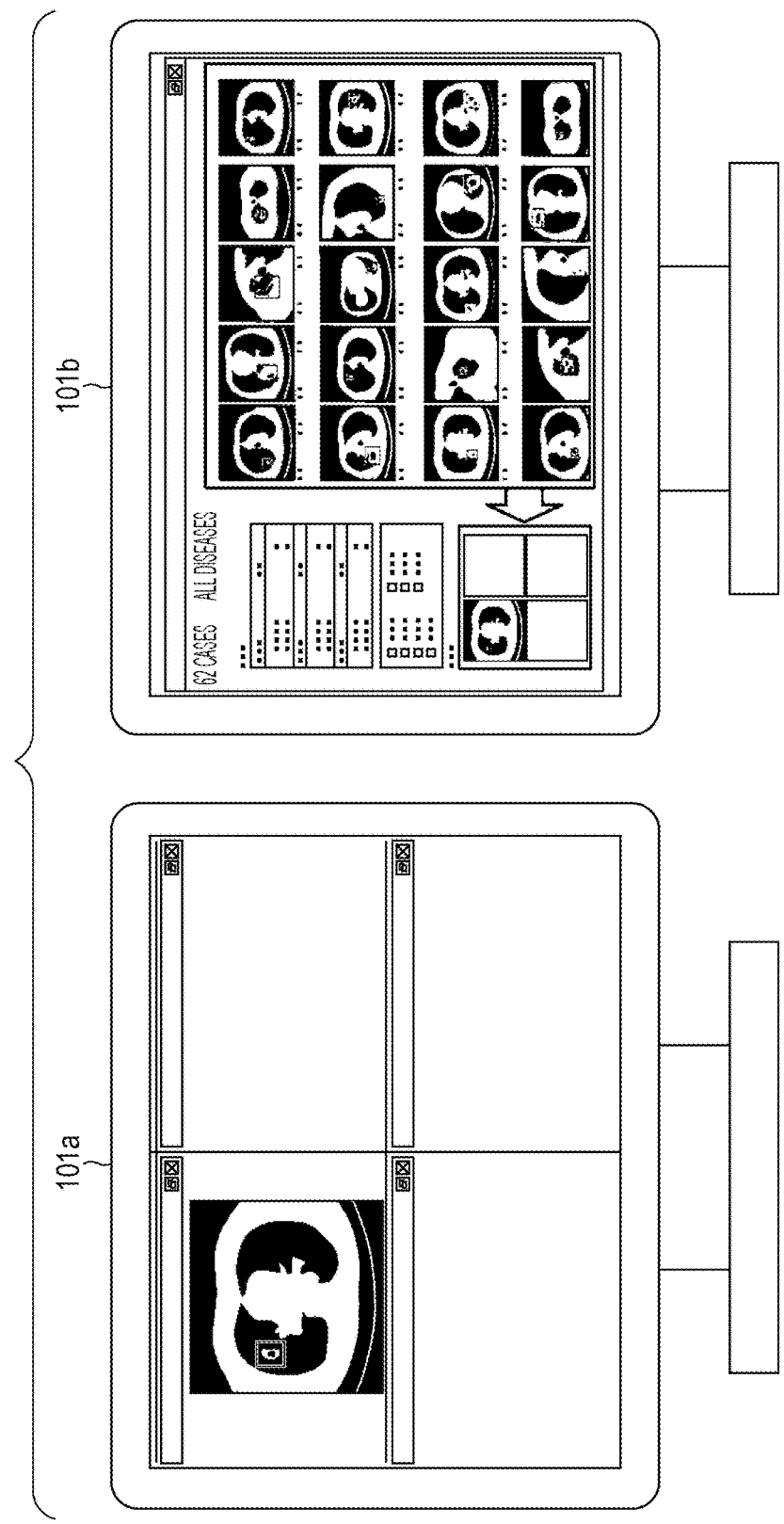
FIG. 3 illustrates external views of 2 displays.

Also, a display window of the display 101a is an example of a second display window, and a display window of the display 101b is an example of a first display window. FIG. 3 illustrates external views of the 2 displays 101a and 101b. In FIG. 3, the display 101a displays 4 medical image viewers in arrangement by 2 columns and 2 rows, and the display 101b displays a window of the case retrieval system 300. If a display 101 is used, the first display window and the second display window are displayed in divided areas in the display window of the display 101.

The operation unit 102 includes, for example, a keyboard and a mouse. The operation unit 102 receives various operations input to the information terminal 100 by a user. For example, the operation unit 102 receives an operation from the user to a medical image and a medical chart image and an operation to input a diagnosis result to the report input window displayed on the display 101.

When the input controller 103 detects an operation by the user to the operation unit 102, the input controller 103 interprets the content of the operation and notifies the other components about the operation content. For example, the input controller 103 detects the position of a mouse pointer on the display 101 from coordinate data output from the mouse serving as the operation unit 102, and causes the display 101 to display the mouse pointer. When the input controller 103 detects a click on the mouse, if a GUI part (for example, a GUI button) generated by the display controller 104 is displayed at the display position of the mouse pointer, the input controller 103 judges that the user selects the GUI and notifies the other components about that the user selects the GUI part.

The display controller 104 generates a graphical user interface (GUI) of the information terminal 100, and causes the display 101 to show the GUI. The display controller 104 may generate information to be displayed on the display 101. The display controller 104 may cause the display 101 to show the generated information.

The ROI manager 105 generates designation information indicative of a region of interest (ROI) that is set with respect to a retrieval query image (described later) when similar case retrieval is executed, stores the designation information in a memory, and manages the designation information.

The display box manager 106 stores display box management information 4410 (FIG. 35, described later) in the memory, and manages the display box management information 4410.

The disease name list manager 108 generates a disease name list (FIG. 29) of similar cases displayed in a case display area 710 (FIG. 6), stores the disease name list in the memory, and manages the disease name list.

The distribution list manager 109 generates a distribution list (FIG. 34) indicative of a sick distribution of the similar cases displayed in the case display area 710, stores the distribution list in the memory, and manages the distribution list.

The communication controller 110 includes, for example, a communication device for connecting the information terminal 100 with the network 400. The communication controller 110 controls communication between the information terminal 100 and the medical information management system 200, and communication between the information terminal 100 and the case retrieval system 300. Also, the communication controller 110 receives a transmission request for various data from another block, and transmits the transmission request to the medical information management system 200 or the case retrieval system 300. In addition, the communication controller 110 receives data transmitted from the medical information management system 200 or the case retrieval system 300, and transmits the data to the corresponding block.

The trimmed image generator 112 trims a similar medical image and generates a trimmed image. The trimmed image generator 112 receives similar case data 4000 (FIG. 20) from a similar case retriever 303, trims an area other than a region of interest (ROI) of a similar medical image displayed in the case display area 710 (FIG. 6) among similar medical images acquired by similar case retrieval, and causes the case display area 710 to display the similar medical image. In this case, the number of similar medical images to be displayed in the case display area 710 may be a value previously determined in accordance with a value indicated by thumbnail display change information (described later) acquired by the operation unit 102 according to an operation by the user.

As shown in FIG. 2, the medical information management system 200 includes a patient information storage 201, a patient information manager 202, a medical image data storage 203, a medical image data manager 204, a diagnosis report manager 205, and a communication controller 206.

The patient information storage 201 stores patient information 1000 (FIG. 16) having registered therein personal information, such as the sex and age of a patient; clinical information such as a medical history; and inspection information of, for example, a blood test.

The patient information manager 202 executes processing of registering data input by the user and updating the patient information 1000, processing of outputting the patient information 1000 to the display controller 104, and other processing on the patient information 1000 (FIG. 16) stored in the patient information storage 201. Thus the patient information manager 202 manages the patient information 1000.

The medical image data storage 203 stores medical image data being inspection images of the patient.

The medical image data manager 204 stores the medical image data in the medical image data storage 203, and manages the medical image data.

The diagnosis report manager 205 manages a diagnosis report 3000 (FIG. 19) indicative of a diagnosis result by the doctor for each inspection executed on the patient.

The communication controller 206 includes, for example, a communication device for connecting the medical information management system 200 with the network 400. The communication controller 206 receives a transmission request for various data from another block, and transmits the transmission request to the information terminal 100 or the case retrieval system 300. In addition, the communication controller 206 receives data transmitted from the information terminal 100 or the case retrieval system 300, and transmits the data to the corresponding block.

As shown in FIG. 2, the case retrieval system 300 includes a similar case data storage 301, an image feature extractor 302, a similar case retriever 303, and a communication controller 304.

The similar case data storage 301 stores in advance an image feature extracted from many similar cases selected as target data for similar case retrieval among similar cases managed by the medical information management system 200, and the similar case data 4000 (FIG. 20) having registered therein a generated thumbnail image etc.

The image feature extractor 302 extracts an image feature of a region of interest of a retrieval query image transmitted from the communication controller 110 of the information terminal 100. Region-of-interest information (ROI information) is an example of designation information indicative of a region of interest.

The similar case retriever 303 generates a similar case retrieval result by comparing the image feature extracted by the image feature extractor 302 with the image feature of at least one similar case stored in the similar case data storage 301.

The communication controller 304 includes, for example, a communication device for connecting the case retrieval system 300 with the network 400. The communication controller 304 receives a transmission request for various data from another block, and transmits the transmission request to the information terminal 100 or the medical information management system 200. In addition, the communication controller 206 receives data transmitted from the information terminal 100 or the medical information management system 200, and transmits the data to the corresponding block.

Figure 4:
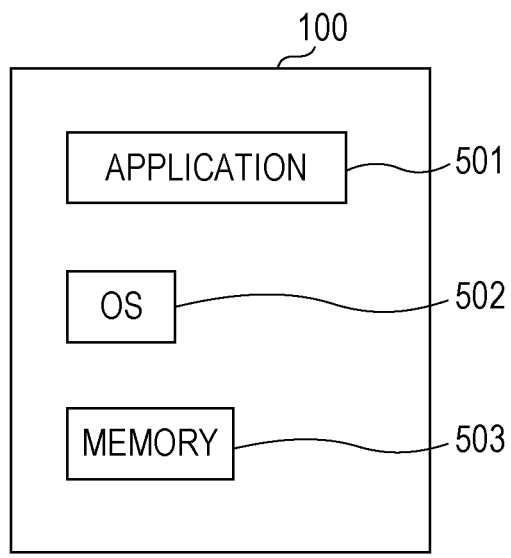
FIG. 4 illustrates a configuration example of a mounting form of the information terminal.

FIG. 4 illustrates a configuration example of a mounting form of the information terminal 100. As shown in FIG. 4, the information terminal 100 includes an application 501, an operating system (OS) 502, a memory 503, and not-illustrated other hardware.

The application 501 is application software to cause the personal computer or the tablet terminal to function as the information terminal 100, and is executed by a processor of the information terminal 100. The information terminal 100 may have mounted therein the application 501 by reading the application 501 from a computer-readable recording medium, or by downloading the application 501 from the network.

In this case, the application 501 includes a medical information management application and a similar case retrieval application. The medical information management application is an application for associating the information terminal 100 with the medical information management system 200. The similar case retrieval application is an application for associating the information terminal 100 with the case retrieval system 300. Both the applications transmit and receive data to and from each other, and integrate services provided by the medical information management system 200 and the case retrieval system 300 in the information terminal 100.

The OS 502 is basic software of the information terminal 100. The OS 502 is executed by the processor of the information terminal 100. The memory 503 is formed of a storage device, such as RAM or ROM, included in the information terminal 100. The memory 503 stores a data group included in the application 501.

The processor of the information terminal 100 executes the application 501, and hence the input controller 103, the display controller 104, the ROI manager 105, the display box manager 106, the disease name list manager 108, the distribution list manager 109, the communication controller 110, and the trimmed image generator 112 shown in FIG. 2 are provided.

However, according to this embodiment, in the information terminal 100, only the application 501 may be mounted, the application 501 and the OS 502 may be mounted, the application 501, the OS 502, and the memory 503 may be mounted, or the application 501, the OS 502, the memory 503, and another not-illustrated hardware may be mounted. In any of such embodiments, the information terminal 100 according to this embodiment can be provided.

Figure 5:
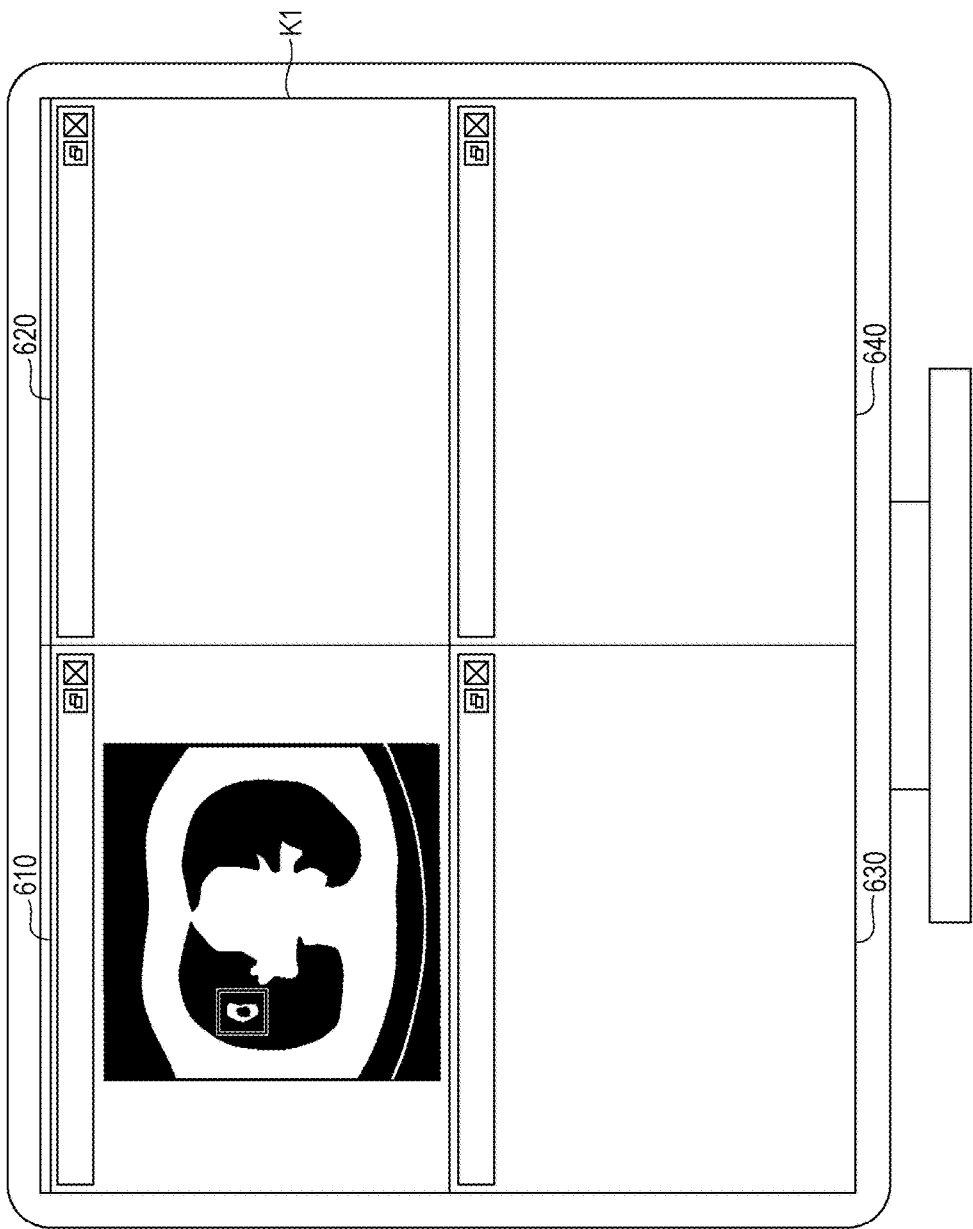
FIG. 5 illustrates an example of a basic window displayed on a display immediately after a similar case retrieval application is activated in the information terminal.

FIG. 5 illustrates an example of a basic window K1 displayed on the display 101 a immediately after the similar case retrieval application is activated in the information terminal 100. The basic window K1 shown in FIG. 5 includes 4 medical image viewers 610 to 640. A medical image is typically recorded in digital imaging and communication in medicine (DICOM) format. The medical image viewers 610 to 640 are viewers that can handle DICOM. It is assumed that a medical image handled in this embodiment is a chest CT image formed of multiple tomographic images (hereinafter, referred to as slice images) in DICOM format. However, this is merely an example, and a CT image of another portion (for example, a head, an abdominal portion, a leg, or an arm) may be used.

In the chest CT image displayed in any of the medical image viewers 610 to 640, the slice images are switched by an operation with the mouse or the keyboard. In this case, the slice images forming the chest CT image are arranged, for example, in the order from the neck side to the abdominal side.

For example, if the mouse pointer is positioned on the medical image viewer 610 and the input controller 103 detects rotation of the mouse wheel, the display controller 104 switches and displays the slice image displayed in the medical image viewer 610 in accordance with the detected rotation amount. In this case, for example, in the medical image viewer 610, if the mouse wheel is rotated by one click rearward of the mouse, the display controller 104 switches the slice image being displayed to a next slice image and displays the slice image. In contrast, for example, in the medical image viewer 610, if the mouse wheel is rotated by one click forward of the mouse, the display controller 104 switches the slice image being displayed to a previous slice image and displays the slice image. Accordingly, the user who is a doctor etc. switches the slice image to be displayed in the medical image viewer 610 while rotating the mouse wheel forward or rearward and searches a desirable slice image.

Instead of the chest CT image, the medical image may be a magnetic resonance imaging (MRI) image or a plain X-ray image. Also, in the example in FIG. 5, the number of medical image viewers is 4; however, this is merely an example, and another number of medical image viewers, such as 6 or 8 medical image viewers may be used. As the number of medical image viewers is increased, the number of images that can be simultaneously compared with each other is increased. However, the display area per image is reduced. Owing to this, a configuration may be used in which the number of medical image viewers can be properly changed in accordance with the display size of the display 101*a*. In this case, it is assumed that the user or manager can desirably change the number of medical image viewers.

Before the similar case retrieval application is activated, slice images of a chest CT image of a patient are displayed in the entire area of the display 101*a*. Then, in this state, if the similar case retrieval application is activated by the user such as a reader, the slice images displayed in the entire area of the display 101*a* are displayed in the medical image viewer 610.

That is, in the medical image viewer 610, when the user activates the similar case retrieval application, the retrieval query image displayed in the entire area of the display 101*a* is initially displayed. The display controller 104 may display a region of interest (ROI) of a target of similar case retrieval in a superposed manner on the retrieval query image. The retrieval query image is an example of a target medical image for reading.

In FIG. 5, no image is displayed in the other medical image viewers 620 to 640. However, if there are a plurality of target inspection images of a patient for reading and if the plurality of inspection images are displayed on the display 101*a* before the similar case retrieval application is activated, the display controller 104 may directly display the plurality of inspection images in the medical image viewers 620 to 640.

Figure 6:
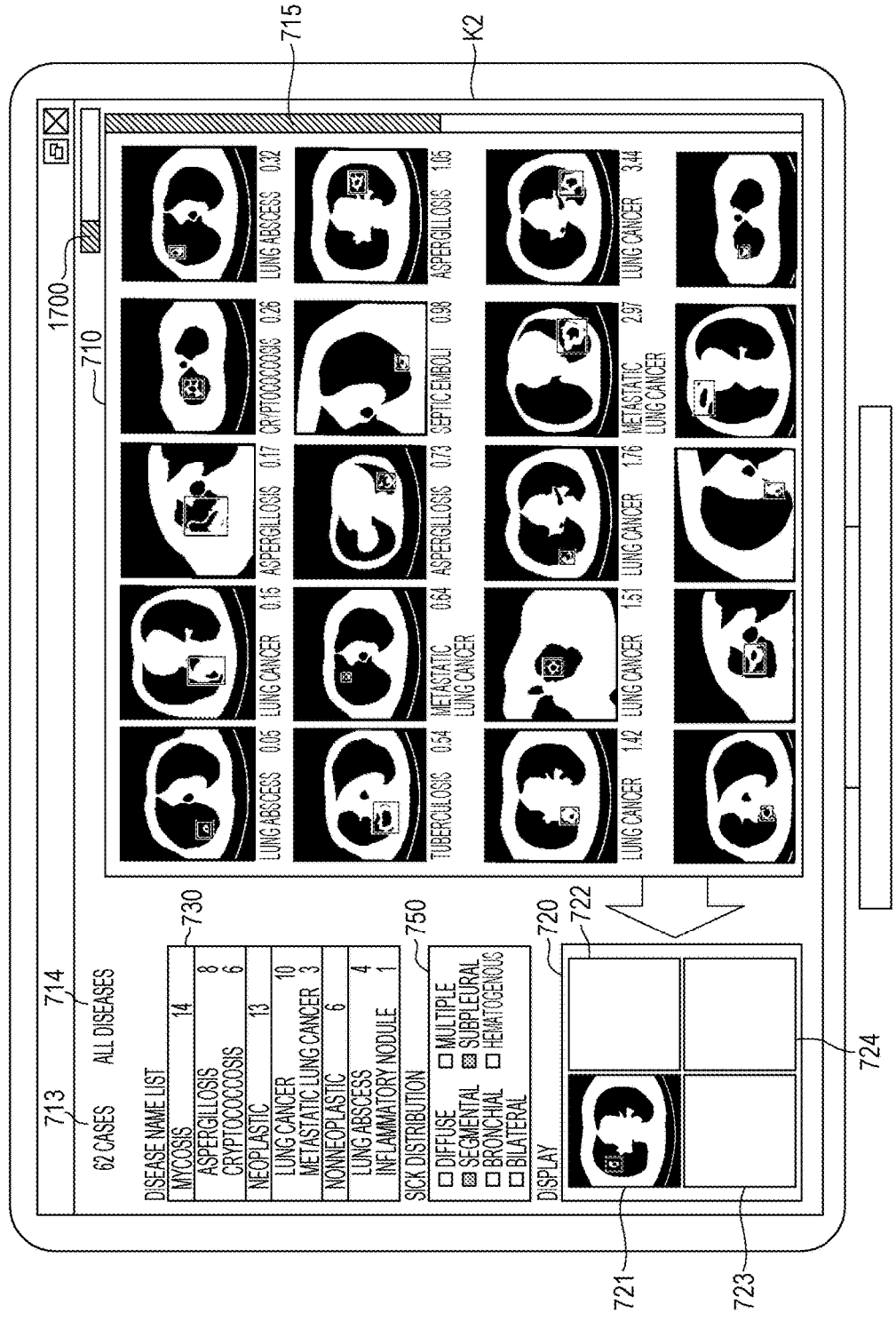
FIG. 6 illustrates an example of a basic window displayed on the display immediately after the similar case retrieval application is activated in the information terminal.

FIG. 6 illustrates an example of a basic window K2 displayed on the display 101*b* immediately after the similar case retrieval application is activated in the information terminal 100. The basic window K2 shown in FIG. 6 includes a case display area 710, a layout area 720, a disease name list display area 730, and a distribution list display area 750. The case display area 710 is an example of a first display area.

The case display area 710 is an area in which thumbnail images of similar cases similar to the retrieval query image are displayed in the order of similarity. In this case, the thumbnail images of the similar cases are each an example of a similar medical image.

Since multiple similar cases are displayed in the case display area 710, if the resolution and pixel value are converted in this situation, the processing may take a time. Hence, the thumbnail images are created from original slice images in advance, and are saved in the case retrieval system 300.

Supplemental description is given for the conversion of resolution and pixel value. An original slice image has a resolution of 512×512 pixels. A thumbnail image has a lower resolution than that of the original slice image, and hence the resolution has to be converted. Owing to this, the thumbnail image is generated by executing low resolution processing and gradation conversion processing on the original slice image.

For example, the gradation conversion processing is executed as described below. Each pixel value (CT value) of a slice image acquired by CT has a value of 2000 levels of gradation in a range from −1000 to +1000 (unit being Hounsfield unit, or HU). The slice image cannot be displayed on a typical display with 8-bit gradation unless the gradation is converted. Even if the slice image can be displayed without conversion, in 2000 levels of gradation, it is difficult for a person with the naked eyes to distinguish a pulmonary emphysema area (CT value: −1000 HU), a normal tissue in a lung field (CT value: about −900 HU), a ground glass area (CT value: −800 HU), a soft tissue (CT value: about −100 to −50 HU), water (CT value: 0 HU), and a bone (CT value: 1000 HU).

Therefore, in general, a window level and a window width are set for each pixel value of the slice image. The pixel value is hence reconfigured into an 8-bit pixel value. Then the reconfigured slice image is displayed on the display. The window level represents the CT value being the center of the window, and the window width represents the vertical width about the center of the window.

For example, if a DICOM image is reconfigured in a lung window, the window level is set in a range from −550 to −800, and the window width is set in a range from 1000 to 1600. Therefore, the thumbnail image is generated by decreasing the pixel value to 8 bits from the original slice image by the above-described processing.

The thumbnail image displayed in the case display area 710 is a thumbnail image representing a similar case at a distance being a predetermined threshold or smaller from a feature vector of a diagnosis target case. In this case, the distance may be, for example, Euclid distance. Alternatively, the distance may be another distance scale, such as city block distance. 2 images being comparison targets are similar to each other as the distance therebetween is smaller.

Also, the feature vector to be used is not obtained from the thumbnail image, but is obtained from the slice image being the original image.

Figure 7:
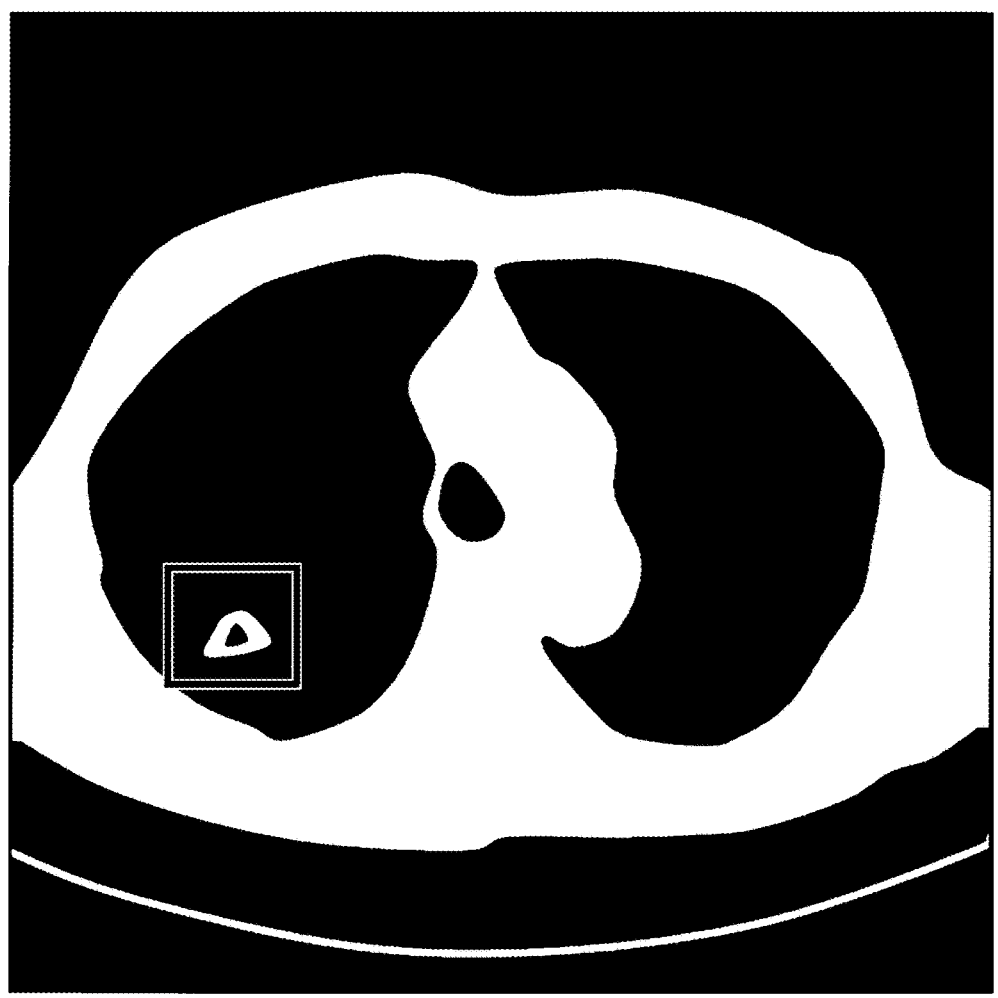
FIG. 7 illustrates a display area of a similar case displayed in a case display area.

FIG. 7 illustrates a display area of a similar case displayed in the case display area 710. A thumbnail image is displayed in the display area of the similar case. A definite diagnosis disease name display area 711 and a distance display area 712 are arranged below the thumbnail image. The definite diagnosis disease name of the target similar case is displayed in the definite diagnosis disease name display area 711. The definite diagnosis disease name represents a disease name with diagnosis determined for the similar case being the target. The distance between the feature vector of the slice image of the similar case to be the target and the feature vector of the retrieval query image is displayed in the distance display area 712. In the example in FIG. 7, since "nontuberculous mycobacteria" is displayed in the definite diagnosis disease name display area 711, the thumbnail image represents a thumbnail image of a similar case with definite diagnosis made as "nontuberculous mycobacteria." Also, since "0.05" is displayed in the distance display area 712, the numerical value represents the distance between the slice image of the similar case and the retrieval query image being "0.05."

Case Display Area 710: Window in Enlargement Operation

Figure 42:
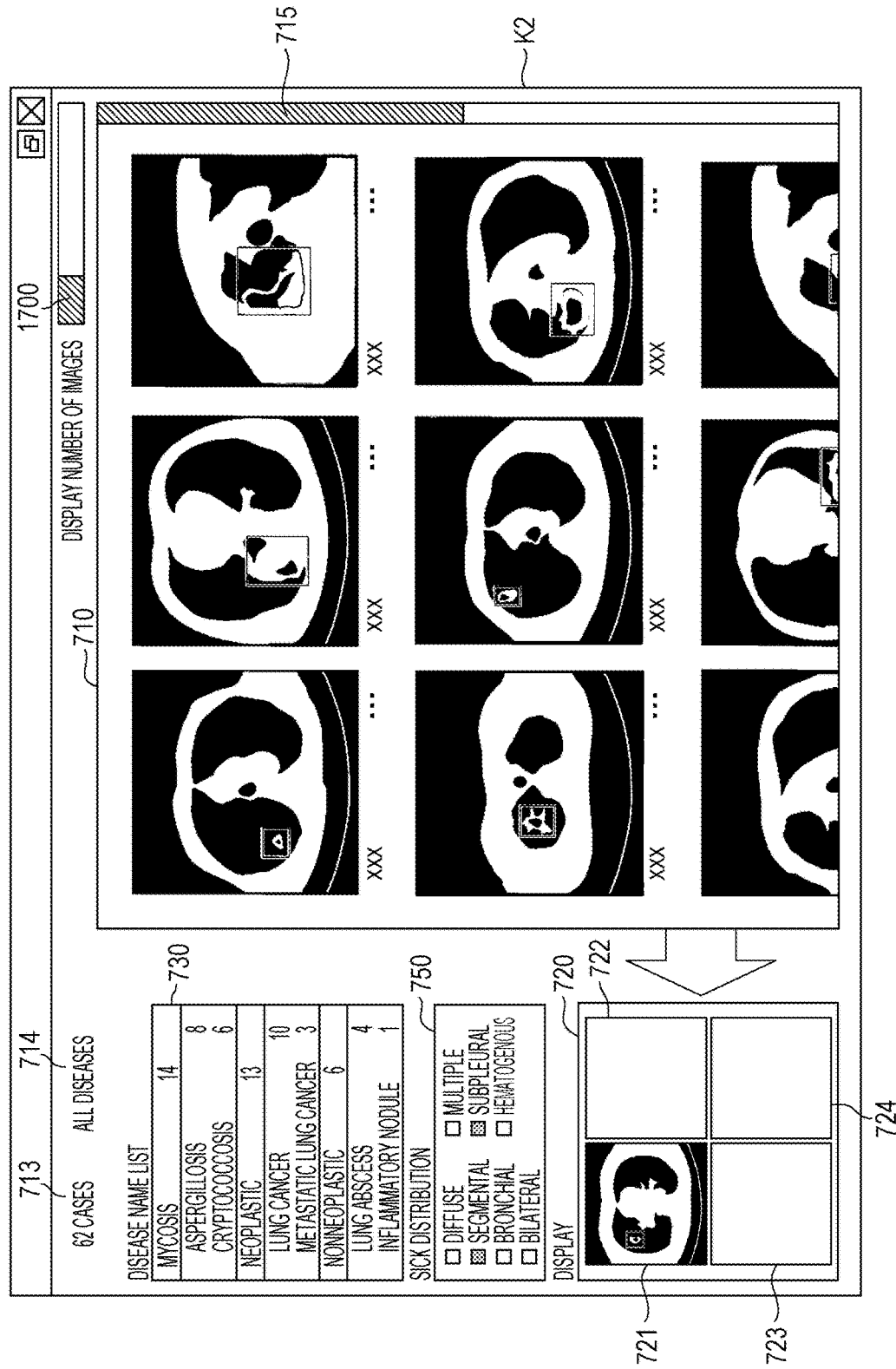
FIG. 42 illustrates an example of a basic window immediately after similar case retrieval.

In the case display area 710, similar medical images similar to the retrieval query are trimmed and displayed in accordance with the display number of thumbnail images designated by the user. FIG. 42 illustrates an example of a basic window K2 immediately after similar case retrieval. In the example in FIG. 42, thumbnail images of target similar cases for displaying are displayed in the case display area 710 in 2 rows by 3 columns. However, substantially lower half portions of the thumbnail images in the 3rd row are hidden. In the basic window K2, a scroll bar 1700 is arranged at the upper right of the case display area 710. The scroll bar 1700 is a GUI part for changing the display number of thumbnail images to be displayed in the case display area 710. In this case, the scroll bar 1700 is long in the horizontal direction; however, this is merely an example, and may be long in the vertical direction.

The user can make an instruction to change the display number of thumbnail images by sliding the scroll bar 1700 horizontally in the case display area 710.

In FIG. 42, the scroll bar 1700 is positioned at the left end of a sliding allowable range of the scroll bar 1700. Hence, in FIG. 42, the thumbnail images of the target similar cases for displaying are displayed with a default size.

A scroll bar 715 being long in the vertical direction is arranged at the right of the case display area 710. The doctor can display the thumbnail images of the hidden similar cases, by sliding the scroll bar 715 vertically. However, with this operation, if a plurality of thumbnail images with a focus of attention are separated in the case display area 710, the doctor has to repetitively input an operation of sliding the scroll bar 715 and compare the plurality of thumbnail images with attention with the retrieval query image. The load of operation of the doctor is increased.

Owing to this, in this embodiment, the scroll bar 1700 that can change the display number of thumbnail images is provided. Accordingly, the doctor can control the display number of thumbnail images that can be displayed at once in the case display area 710 by sliding the scroll bar 1700. Hence, even if the plurality of thumbnail images with attention are separated in the case display area 710, the plurality of thumbnail images with attention can be simultaneously displayed in the case display area 710. The doctor can smoothly compare the plurality of thumbnail images with attention with the retrieval query image.

Figure 43:
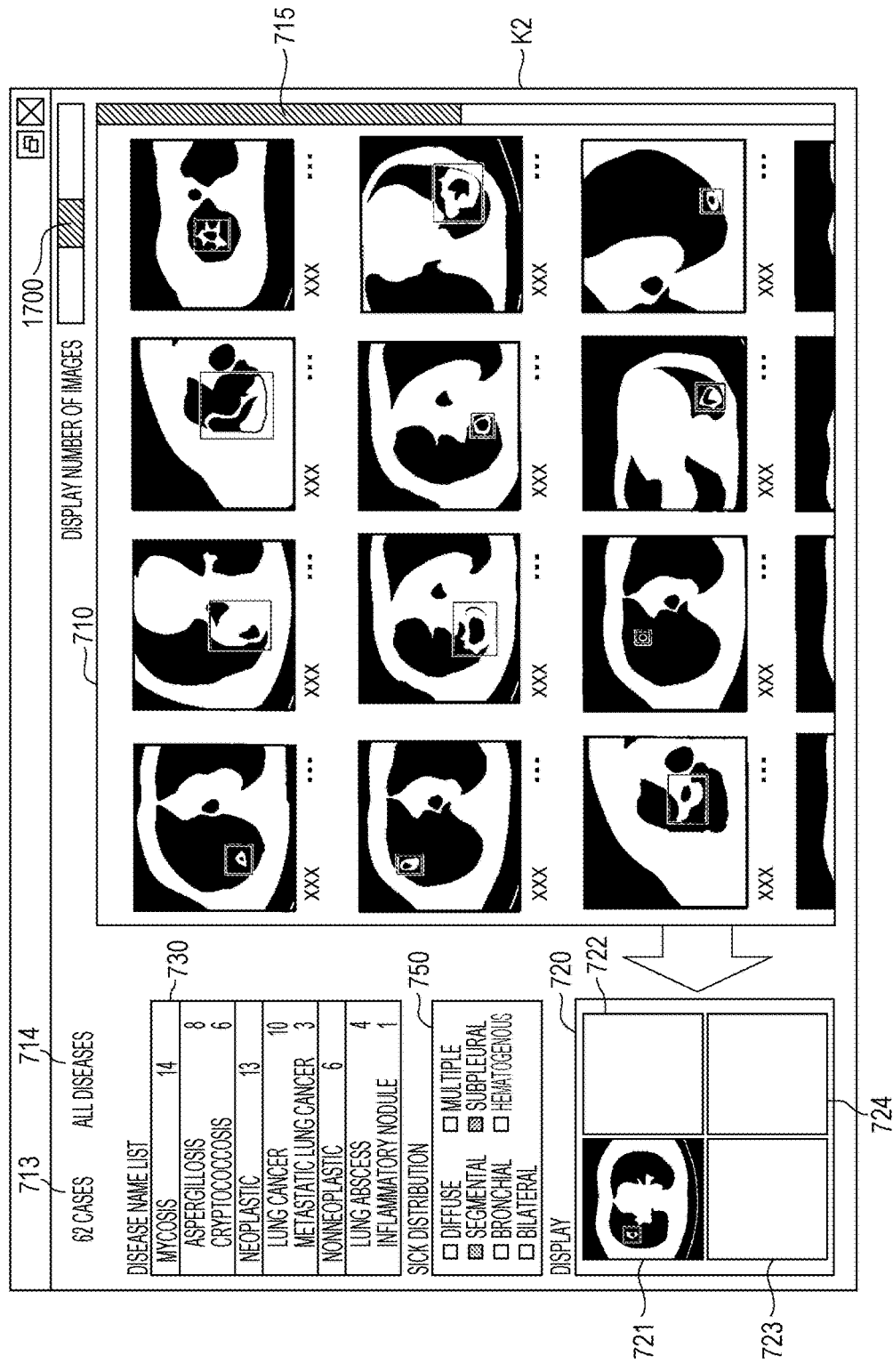
FIG. 43 illustrates an example of a basic window when the display number of thumbnail images displayed in a case display area in FIG. 42 is increased.

When the input controller 103 detects the instruction to change the display number of thumbnail images from the user, as shown in FIG. 43, the trimmed image generator 112 trims image areas other than ROIs of the thumbnail images of target similar cases for displaying among the thumbnail images of the similar cases similar to the retrieval query image while the areas of the ROIs are kept unchanged. Accordingly, since the sizes of the individual thumbnail images are reduced, the number of thumbnail images that can be displayed in the case display area 710 having a constant area can be increased. Then, the display controller 104 lists and displays the trimmed thumbnail images of the similar cases in the case display area 710 in the descending order of similarity. The details of the trimming processing on the thumbnail images are described later.

In FIG. 43, the scroll bar 1700 which is displayed at the left end of the sliding range in FIG. 42 is shifted rightward. Accordingly, in the example in FIG. 43, the thumbnail images displayed only by 9 in 3 rows by 3 columns in the case display area 710 in FIG. 42 are reduced in size by trimming, and hence the thumbnail images are displayed by 12 in 3 rows by 4 columns. It is found that 3 thumbnail images are increased.

To be specific, the thumbnail image displayed in the 2nd row and 1st column in FIG. 42 is displayed in the 1st row and 4th column in FIG. 43, and the thumbnail image in the 2nd row and 2nd column in FIG. 42 is displayed in the 2nd row and 1st column in FIG. 43. Thus, the respective thumbnail images are displayed so that an image moves over to a previous position.

Accordingly, the sizes of the thumbnail images can be reduced while the image sizes of the ROIs required in diagnosis are kept unchanged. The doctor can compare the retrieval query image with the image group of the retrieval results for similarity by one instruction. The operating time can be markedly decreased.

In the example in FIG. 43, in the case display area 710, the 4 thumbnail images of the similar cases having the first to fourth similarities are displayed in the descending order of similarity from the left to the right in the 1st row, and the 4 thumbnail images of the similar cases having the fifth to eighth similarities are displayed in the descending order of similarity from the left to the right in the 2nd row. In this way, the thumbnail images of the similar cases are displayed in the descending order of similarity in a meandering manner from the upper left to the lower right. Hence, the user can quickly recognize the ordinal number of each of the thumbnail images displayed in the case display area 710 with respect to the retrieval query image.

Figure 44:
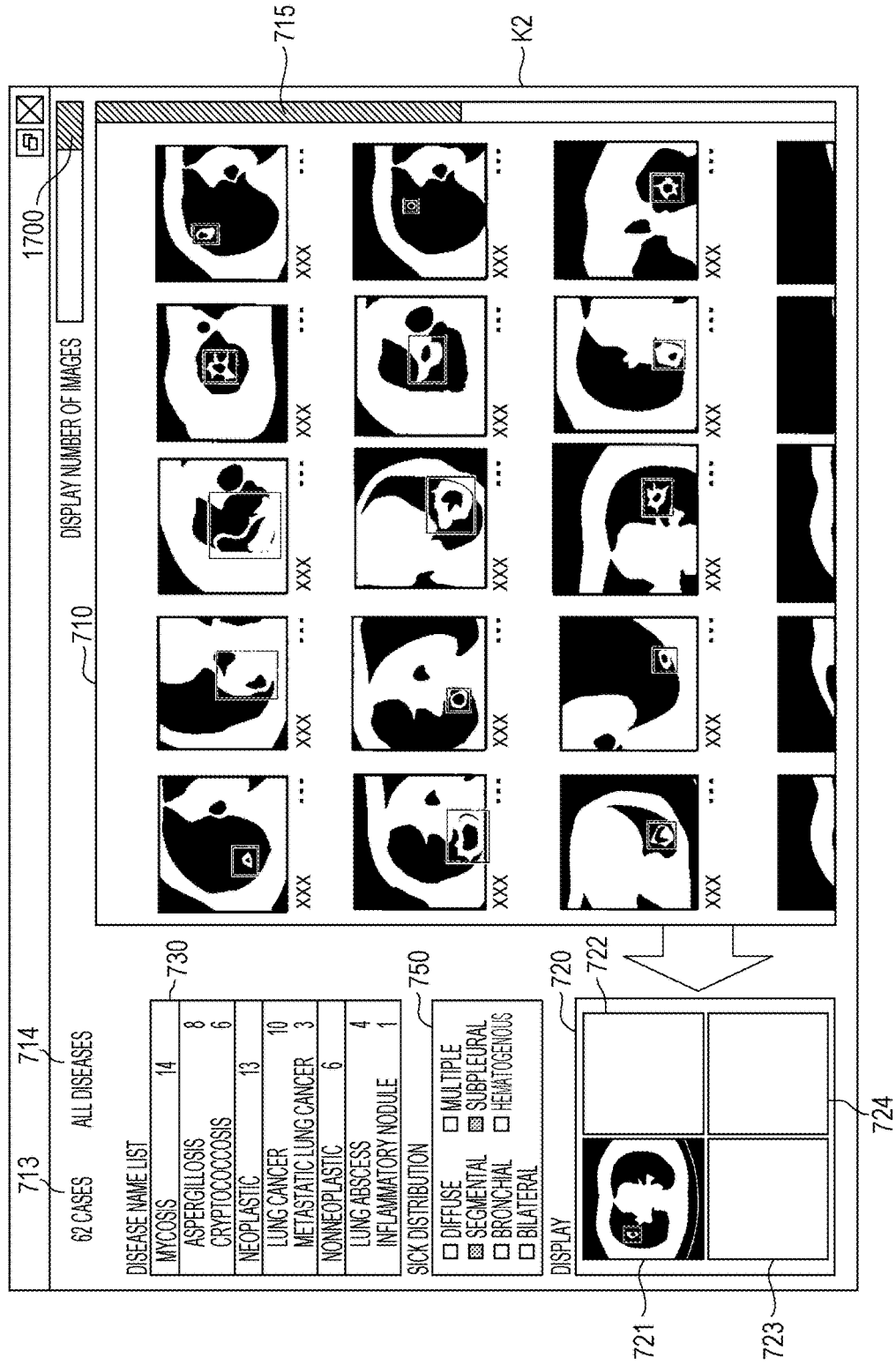
FIG. 44 illustrates an example of a basic window when the display number of thumbnail images displayed in a case display area in FIG. 43 is increased.

In FIG. 44, the scroll bar 1700 is further slid to the right, and the scroll bar 1700 is slid to the right end of the sliding allowable range. Accordingly, in the example in FIG. 44, the thumbnail images displayed by 12 in 3 rows by 4 columns in the case display area 710 are reduced in size by trimming, and hence the thumbnail images are displayed by 15 in 3 rows by 5 columns. It is found that 3 thumbnail images are increased as compared with FIG. 43.

Referring back to FIG. 6, a retrieval result number display area 713 is arranged, for example, in an upper left section of the basic window K2. The retrieval result number display area 713 displays the number of similar cases similar to the diagnosis target case, the similar cases being acquired from the case retrieval system 300 as the result of the retrieval processing.

If the number of similar cases is very large, the case display area 710 cannot display all the similar cases at once. Hence, for example, the scroll bar 715 being long in the vertical direction is provided at the right of the case display area 710. The display controller 104 displays the thumbnail images displayed in the case display area 710 in a scrolled manner in the vertical direction in accordance with the moving amount of the scroll bar 715. Accordingly, the user can cause the case display area 710 to display hidden similar cases and can observe the similar cases.

Alternatively, the scroll bar 715 may be long in the horizontal direction. In this case, the display controller 104 may display the thumbnail images displayed in the case display area 710 in a scrolled manner in the horizontal direction in accordance with the moving amount of the scroll bar 715. Alternatively, when a direction key of the keyboard is pressed while the mouse pointer is positioned in the case display area 710, the display controller 104 may display the thumbnail images in the case display area 710 in a scrolled manner in the direction indicated by the pressed key while the key is pressed.

In the above description, the information terminal 100 acquires the thumbnail images at the distances from the retrieval query image being equal to or smaller than the predetermined threshold, from the case retrieval system 300. However, this is merely an example. For example, the information terminal 100 may constantly acquire a predetermined number of thumbnail images in the descending order of similarity from the case retrieval system 300. Alternatively, the information terminal 100 may acquire thumbnail images from the case retrieval system 300 so that the thumbnail images constantly include a predetermined number of thumbnail images of a certain definite diagnosis disease name.

The method of displaying the thumbnail images in the case display area 710 may be a displaying method including displaying a thumbnail image at the smallest distance from the retrieval query image at the left end in the uppermost row, displaying thumbnail images so that the distances are sequentially increased to the right, and when a thumbnail image reaches the right end in the same row, displaying a thumbnail image at a next larger distance at the left end in the 2nd row. That is, there may be employed a method of displaying thumbnail images in the order from a small distance in a meandering manner from the upper left to the lower right in the case display area 710.

Of course, another displaying method may be employed in this embodiment. For example, there may be employed a displaying method including displaying a thumbnail image at the smallest distance at the upper end in the 1st column counted from the left, displaying thumbnail images so that the distances are sequentially increased to the lower side, and when a thumbnail image reaches the lower end in the same column, displaying a thumbnail image at a next larger distance at the upper end in the 2nd column counted from the left. Alternatively, a user may select one of these plural displaying methods.

Also, in the above-described example, the distance is employed for the similarity. However, any index may be employed as long as the index indicates the similarity between images, such as cosine similarity. If the cosine similarity is employed, the similarity between 2 images being comparison targets is increased as the value approaches 1.

Although the details are described later, the similar cases displayed in the case display area 710 can be narrowed down to the disease name displayed in the disease name list display area 730 or the sick distribution displayed in the distribution list display area 750. The currently set narrowing down condition for the similar cases is displayed in a display condition display area 714. The example in FIG. 6 is in a state immediately after the similar case retrieval, and narrowing down is not executed. Hence, the display condition display area 714 displays "all diseases."

The layout area 720 is arranged, for example, in a lower left section of the basic window K2 shown in FIG. 6. The layout area 720 is used for displaying images that the user wants to observe in detail among the thumbnail images of the similar cases displayed in the case display area 710, in the medical image viewers of the display 101a. As shown in FIG. 5, the 4 medical image viewers 610 to 640 are displayed in 2 rows by 2 columns in the display 101a. Also, 4 display boxes 721 to 724 are present in 2 rows by 2 columns in the layout area 720. In this way, the number and arrangement of the medical image viewers 610 to 640 displayed in the display 101a correspond to the number and arrangement of the display boxes 721 to 724 in the layout area 720. As shown in FIG. 5, the retrieval query image is displayed in the medical image viewer 610. To meet this, the thumbnail image of the retrieval query image is initially displayed in the display box 721.

In the other display boxes 722 to 724, thumbnail images of similar cases are displayed in association with the medical image viewers 620 to 640. That is, if the input controller 103 detects drag-and-drop of one of the thumbnail images displayed in the case display area 710 to any one of the display boxes 722 to 724, the display controller 104 causes the display box to display the one thumbnail image, and causes the medical image viewer corresponding to the display box to display a slice image corresponding to the thumbnail image. In this way, the medical image viewers 610 to 640 correspond to the display boxes 721 to 724 in a one-to-one relationship.

In the example in FIG. 6, since the display boxes 722 to 724 are blank, the medical image viewers 620 to 640 shown in FIG. 5 are also blank.

The user moves a thumbnail image that the user wants to observe in detail from the case display area 710 to the layout area 720 by drag-and-drop with the mouse. For example, if the user moves a thumbnail image to the display box 722, a slice image corresponding to the thumbnail image is displayed in the medical image viewer 620 corresponding to the display box 722. Similarly, if the user moves a thumbnail image to the display box 723, a slice image corresponding to the thumbnail image is displayed in the medical image viewer 630 corresponding to the display box 723. That is, if a thumbnail image is moved to any display box of the display boxes 721 to 724, a thumbnail image of a similar case is displayed next to the thumbnail image of the retrieval query image. Accordingly, the user can compare the diagnosis target case with the similar case in the level of thumbnail image, and the user can quickly determine the similarity between both the cases. That is, since a thumbnail image has an information amount smaller than that of a slice image, the similarity between the diagnosis target case and the similar case arranged next to each other in the layout area 720 can be roughly estimated. Hence, the user can efficiently narrow down final candidates of the similar cases required to be compared with the diagnosis target case in detail in the level of slice image among the many similar cases displayed in the case display area 710.

Similarly, the slice images of the retrieval query image and the similar cases are displayed in the display 101a with the same arrangement relationship as that of the layout area 720. Accordingly, when narrowing down the similar cases being the final candidates in the layout area 720 is ended, the diagnosis target case and the similar cases narrowed down as the final candidates are displayed in the level of slice image in the display 101a without input of any operation. Therefore, the user can smoothly shift to the next step of reading the diagnosis target case and the similar cases being the final candidates in detail.

In an upper left section of the basic window K2 shown in FIG. 6, the disease name list display area 730 with a heading of "disease name list" is arranged. In the disease name list display area 730, definite diagnosis disease names of all similar cases acquired as the retrieval results of the similar cases are displayed. After the diagnosis is ended and a definite diagnosis disease name is applied, the diagnosis target case is stored as a similar case in the case retrieval system 300. Therefore, each similar case is applied with a definite diagnosis disease name given by the diagnosis.

FIG. 8 is an enlarged view of the disease name list display area 730. In FIG. 8, the definite diagnosis disease names are classified into broad category disease names (731, 734, 737, 741, and 744) and detailed category disease names (732, 733, 735, 736, 738, 739, 740, 742, 743, and 745) and displayed. In the example in FIG. 8, as the broad category disease names, mycosis 731, neoplastic 734, nonneoplastic 737, mycobacteriosis 741, and others 744 are displayed.

Also, in the example in FIG. 8, as the detailed category disease names of the mycosis 731, aspergillosis 732 and cryptococcosis 733 are displayed. Also, as the detailed category disease names of the neoplastic 734, lung cancer 735 and metastatic lung cancer 736 are displayed. Also, as the detailed category disease names of the nonneoplastic 737, lung abscess 738, sarcoidosis 739, and septic emboli 740 are displayed. Also, as the detailed category disease names of the mycobacteriosis 741, nontuberculous mycobacteria (NTM) 742 and tuberculosis 743 are displayed. Also, as the detailed category disease name of others 744, bronchiectasis 745 is displayed.

Figure 9:
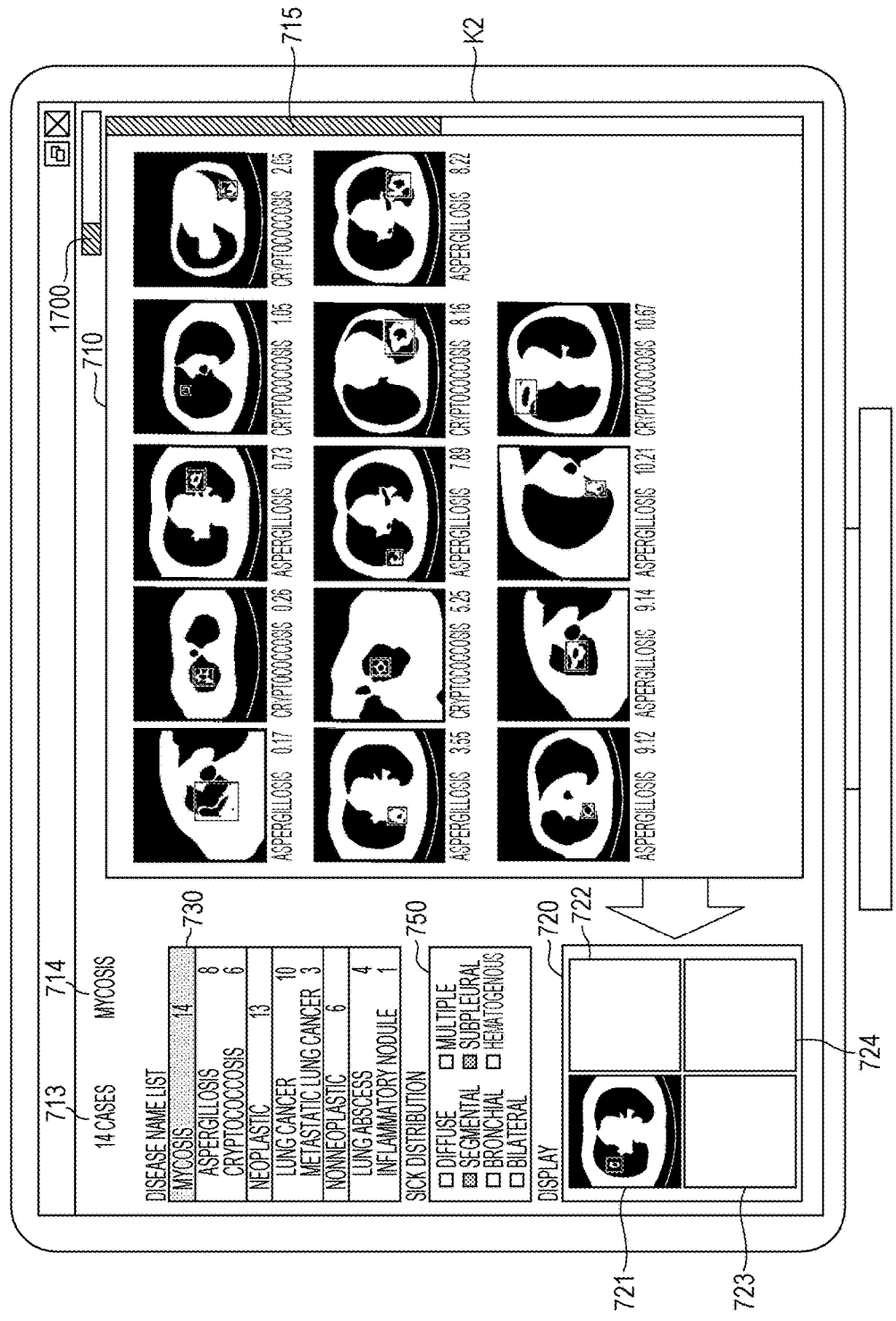
FIG. 9 illustrates a basic window when similar cases are narrowed down to "mycosis;"
Figure 10:
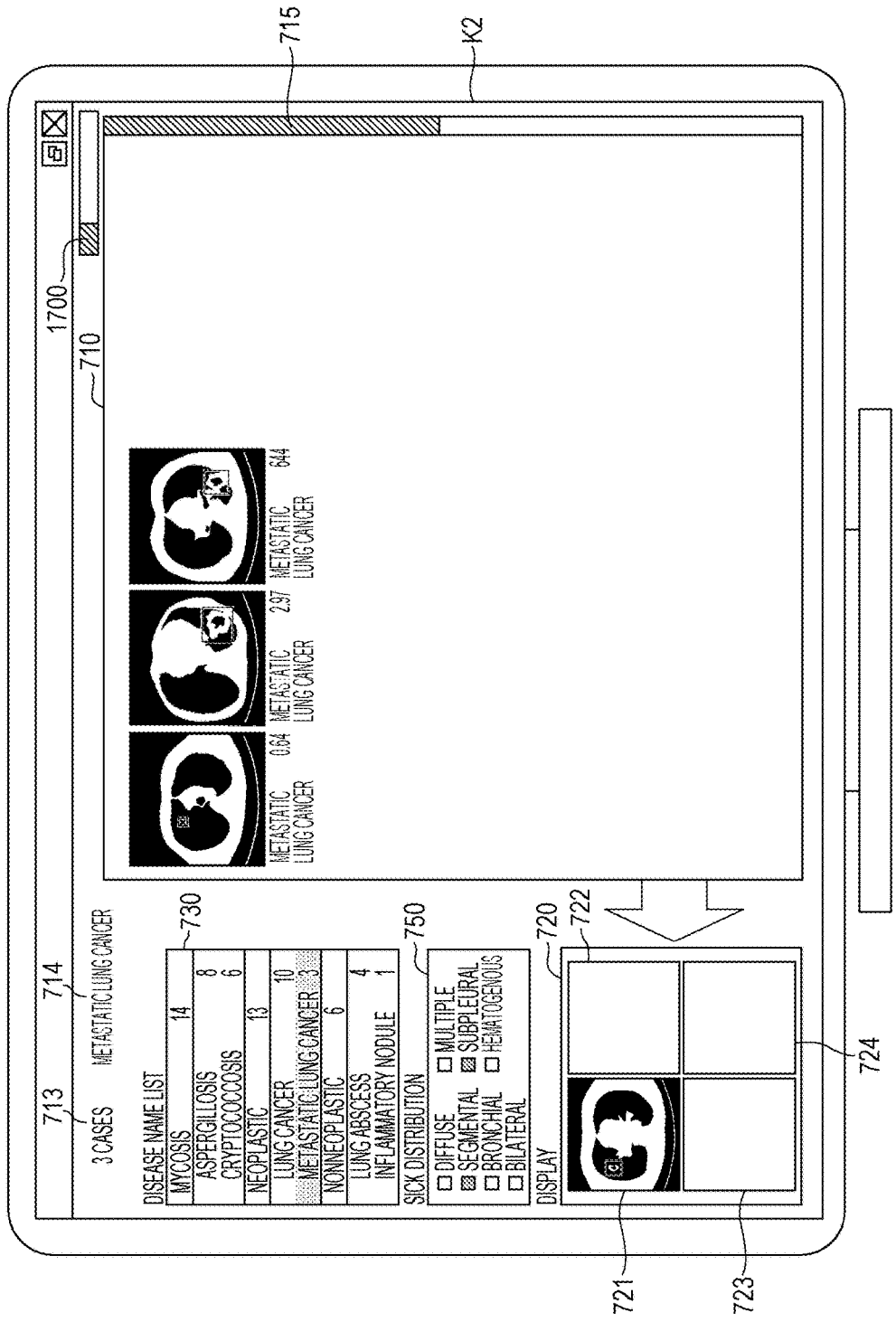
FIG. 10 illustrates a basic window when similar cases are narrowed down to "metastatic lung cancer;"

In addition, the number of cases of the disease is displayed next to each of the broad category disease names and each of the detailed category disease names. The user can narrow down the similar cases displayed in the case display area 710 by selecting a desirable row of the broad category disease names or the detailed category disease names in the disease name list display area 730. As shown in FIG. 6, immediately after the similar case retrieval, 62 similar cases including various diseases are target similar cases for displaying. However, if the row of the mycosis 731 in FIG. 8 is clicked with the mouse, the display controller 104 causes the case display area 710 to display similar cases of mycosis as shown in FIG. 9. Also, if the row of the metastatic lung cancer 736 in FIG. 8 is clicked with the mouse, the display controller 104 causes the case display area 710 to display similar cases of metastatic lung cancer as shown in FIG. 10.

At this time, the display controller 104 causes the display condition display area 714 to display the narrowed down disease name to clarify the narrowing down condition of the similar cases currently displayed in the case display area 710. FIG. 9 illustrates a basic window K2 when the similar cases are narrowed down to "mycosis." FIG. 10 illustrates a basic window K2 when the similar cases are narrowed down to "metastatic lung cancer."

In the example in FIG. 9, since the narrowing down is executed to "mycosis," "mycosis" is displayed in the display condition display area 714. In the example in FIG. 10, since the narrowing down is executed to "metastatic lung cancer," "metastatic lung cancer" is displayed in the display condition display area 714.

Also, at this time, the display controller 104 causes the retrieval result number display area 713 to display the number to clarify the number of similar cases currently displayed in the case display area 710. In the example in FIG. 9, since the similar cases corresponding to "mycosis" are 14 cases, an indication of 14 cases is displayed in the retrieval result number display area 713. In the example in FIG. 10, since the similar cases corresponding to "metastatic lung cancer" are 3 cases, an indication of 3 cases is displayed in the retrieval result number display area 713.

With this function, the similar cases of the disease name expected to be the target for image diagnosis by the doctor is displayed in the case display area 710, and hence the doctor can easily check whether or not the diagnosis target case is consistent with the expected disease name.

In a middle left section of the basic window K2 shown in FIG. 6, the distribution list display area 750 with a heading of "sick distribution" is arranged. In the distribution list display area 750, types of sick distributions of all the similar cases acquired from the case retrieval system 300 as the result of the similar case retrieval are displayed.

FIG. 11 is an enlarged view of the distribution list display area 750. In the example in FIG. 11, 7 sick distribution names are displayed, and checkboxes are arranged at the left of the sick distribution names. In the example in FIG. 11, as the sick distributions, diffuse 751, segmental 752, bronchial 753, bilateral 754, multiple 755, subpleural 756, and hematogenous 757 are displayed.

These sick distributions are previously defined. Each of the similar cases is applied with a distribution flag value (appropriate: 1, inappropriate: 0) indicative of whether or not the similar case is appropriate to any of the diffuse 751 to the hematogenous 757 in advance. There may be a case in which all the distribution flag values are set at inappropriate (: 0) or a case in which a plurality of distribution flag values are set at appropriate (: 1) depending on the similar case.

The case retrieval system 300 according to this embodiment retrieves a similar case having a region of interest similar to a region of interest set in a slice image of a diagnosis target case by the user. A sick portion may be present in an image other than the slice image with the region of interest set by the user. Then, after the user retrieves a similar case with the slice image having set therein the region of interest, in some cases, the user may want to compare a slice image other than the slice image with the retrieved similar case. In this case, the user inputs an operation of slice-by-slice advance in the medical image viewer 610 to display other slice images, and compares the slice image with the retrieved similar case. In this case, if a similar case relating to the sick portion with attention among all the retrieved similar cases is displayed in the case display area 710, a slice image having a desirable sick portion can be smoothly extracted from slice images other than the slice image having set therein the region of interest. Hence, in this embodiment, a function of narrowing down the retrieved similar cases to a desirable sick distribution is provided to further smoothly execute the extraction.

In this embodiment, the sick distributions in the lung field area employ sick distributions indicated by the diffuse 751 to the hematogenous 757 in FIG. 11. Also, as shown in FIG. 11, regarding the checkboxes and the disease distribution names, the display controller 104 causes sick distributions that can be narrowed down to be displayed in an active state, and sick distributions that cannot be narrowed down to be displayed in an inactive state. In this case, the active state is a state with a higher brightness than that in the inactive state, and the inactive state is a state with a lower brightness than that in the active state.

In the example in FIG. 11, the diffuse 751, the bronchial 753 to the multiple 755, and the hematogenous 757 are displayed in the active state, and the segmental 752 and the subpleural 756 are displayed in the inactive state. This is because the distribution flag values of the diffuse 751, the bronchial 753 to the multiple 755, and the hematogenous 757 are set at 1 (appropriate) in at least one of all the similar cases currently acquired by similar case retrieval, and the distribution flag values of the segmental 752 and the subpleural 756 are set at 0 (inappropriate) in any of all the acquired similar cases.

If the input controller 103 detects that a checkmark is input in at least one of the checkboxes in the active state, the display controller 104 causes the case display area 710 to display only similar cases corresponding to the sick condition with the checkmark input.

The distribution flag values of the segmental 752 and the subpleural 756 are set at 0 (inappropriate) for any of the similar cases acquired as the retrieval result. Owing to this, if a configuration in which checkmarks can be input to the segmental 752 and the subpleural 756, and if the checkmarks are input to these sick distributions, no similar case is displayed in the case display area 710, and inputting the checkmarks may be meaningless. Hence, in this embodiment, to avoid such a situation, the sick distribution whose distribution flag value is 0 (inappropriate) in any of the similar cases acquired as the retrieval result, the sick distribution is displayed in the inactive state.

Figure 13:
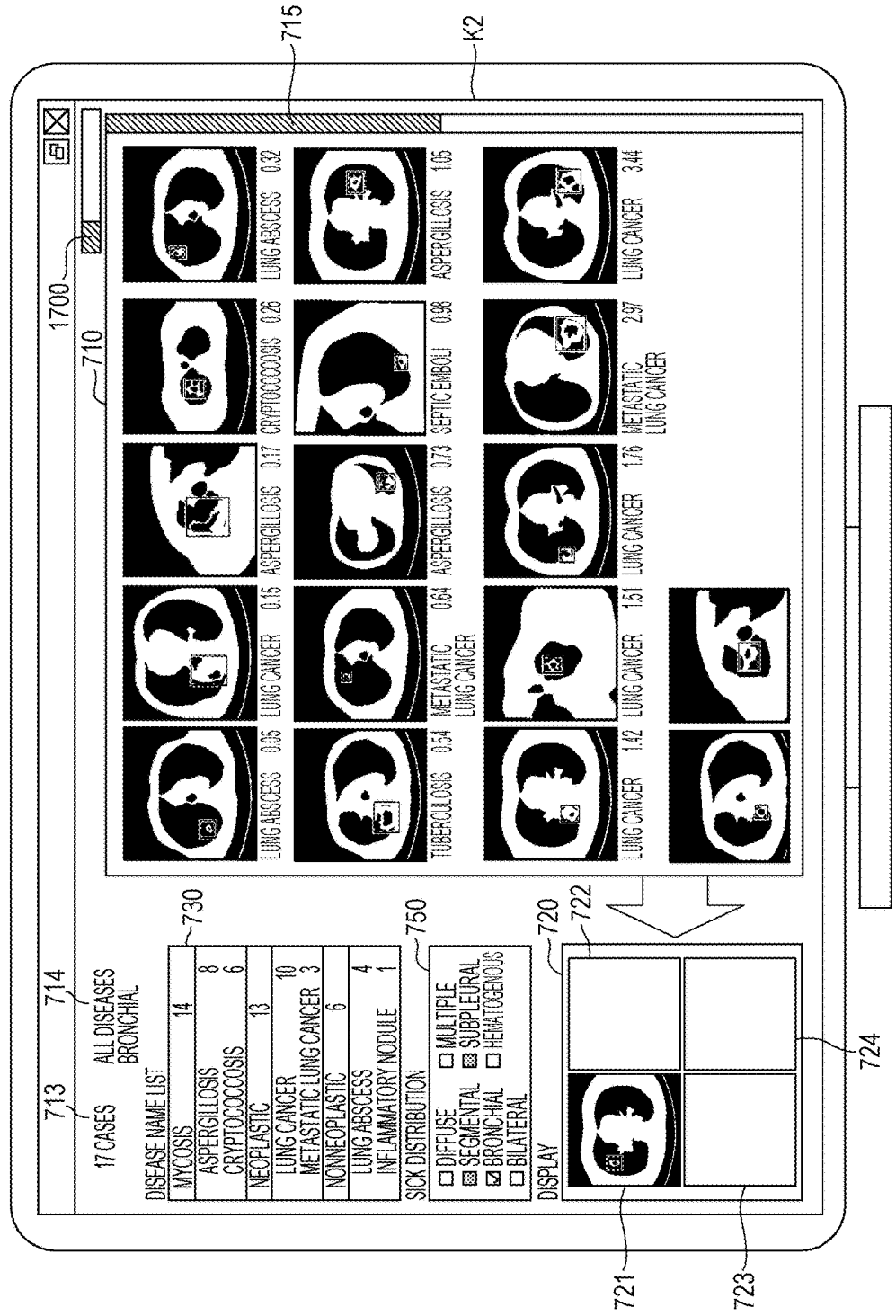
FIG. 13 illustrates the basic window after narrowing down to a bronchial sick distribution.

FIG. 12 illustrates the distribution list display area 750 with a checkmark input. FIG. 13 illustrates the basic window K2 after narrowing down to a bronchial sick distribution. As shown in FIG. 12, when a checkmark is input to the checkbox of the bronchial 753, the display controller 104 causes the case display area 710 to display similar cases having bronchial sick distribution as shown in FIG. 13. In this example, the similar cases having the bronchial sick distribution are 17 cases. Owing to this, the display controller 104 causes the retrieval result number display area 713 to display "17 cases." Also, the display controller 104 causes the display condition display area 714 to display the target disease name for displaying, and "bronchial" being the name of the sick distribution. In the example in FIG. 13, since narrowing down to a disease name listed in the disease name list display area 730 is not executed, the display condition display area 714 displays "all diseases."

Figure 15:
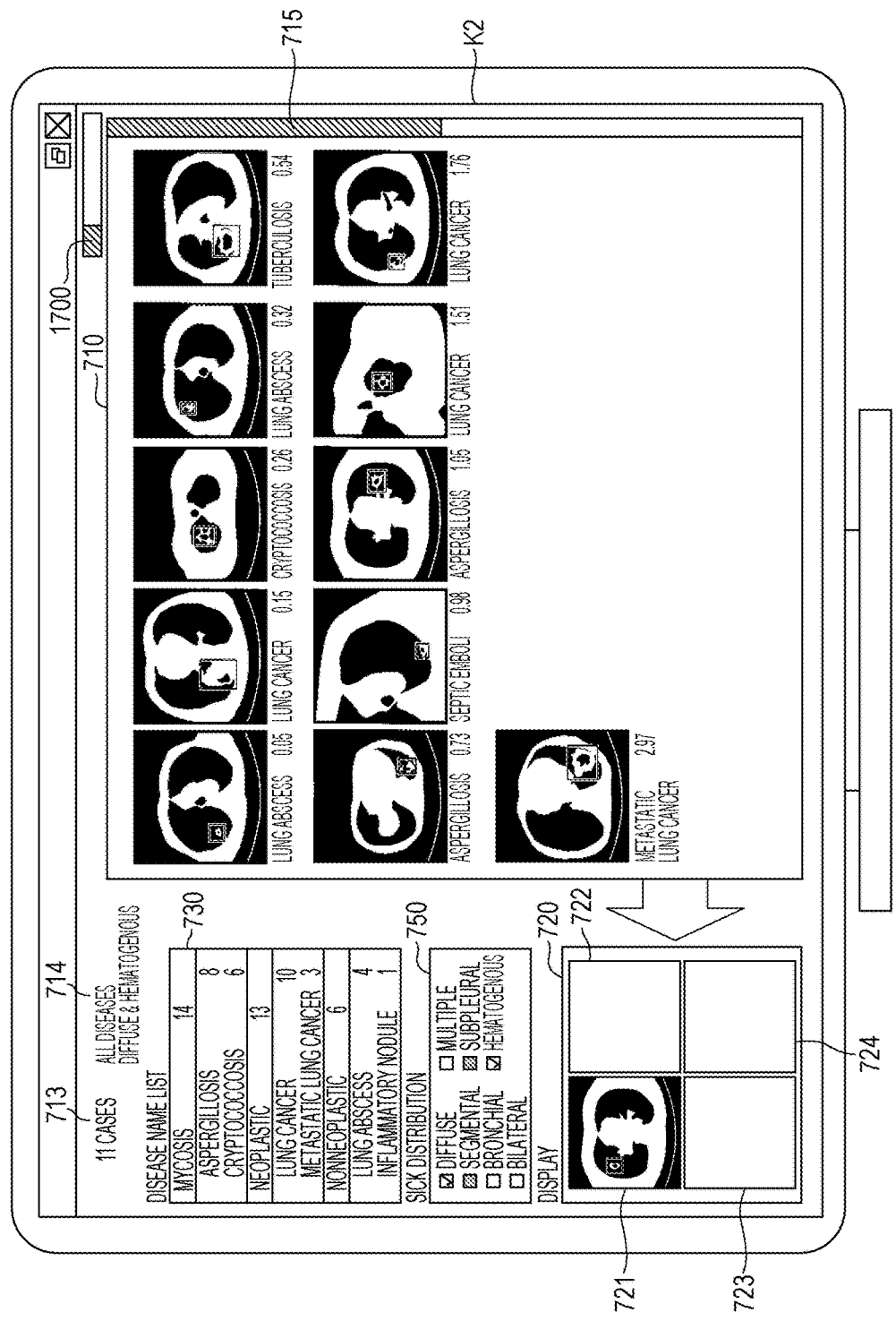
FIG. 15 illustrates the basic window after narrowing down to a plurality of sick distributions.

FIG. 14 illustrates the distribution list display area 750 when a plurality of checkmarks are input. FIG. 15 illustrates the basic window K2 after narrowing down to plural sick distributions. In the example in FIG. 14, checkmarks are input to the diffuse 751 and the hematogenous 757. Owing to this, as shown in FIG. 15, the display controller 104 causes the case display area 710 to display similar cases having sick distributions of the diffuse and hematogenous. In this example, the similar cases having the diffuse and hematogenous sick distributions are 11 cases. Owing to this, the display controller 104 causes the retrieval result number display area 713 to display "11 cases." Also, the display controller 104 causes the display condition display area 714 to display a target disease name for displaying (in this case, since narrowing down to a disease name is not executed, "all diseases") and diffuse and hematogenous" being the names of sick distributions.

FIG. 16 illustrates a data configuration of the patient information 1000. The patient information 1000 is stored in the patient information storage 201 of the medical information management system 200 on a patient basis, and managed by the patient information manager 202 of the medical information management system 200. The patient information 1000 has registered therein personal information, such as the sex and age of a patient; clinical information such as a medical history; and inspection information of, for example, a blood test. As shown in FIG. 16, the patient information 1000 includes patient ID 1100, name 1200, age 1300, sex 1400, medical history 1500, family medical history 1600, chief complaint 17001, inspection information 1800, and definite diagnosis 1900.

The patient ID 1100 is an identifier unique to a patient. The name 1200, the age 1300, the sex 1400, the medical history 1500, the family medical history 1600, and the chief complaint 17001 are the name, age, sex, medical history, family medical history, and chief complaint of the patient with the patient ID 1100. The inspection information 1800 represents information relating to at least one inspection performed on the patient in the past as shown in FIG. 17.

FIG. 17 illustrates a data configuration of the inspection information 1800 registered in the patient information 1000 shown in FIG. 16. The inspection information 1800 is information relating to an inspection performed on a patient. A piece of inspection information 1800 is created for an inspection. The inspection information 1800 includes inspection ID 1810, inspection date 1820, inspection type 1830, and inspection result 1840. The inspection ID 1810 is an identifier unique to an inspection. The inspection date 1820 is the date and time that the inspection is performed. The inspection type 1830 is the type of the inspection. The type of the inspection is, for example, a blood test, a respiratory function inspection, an endoscopic inspection, plain X-ray imaging, CT imaging, and other inspection.

The inspection result 1840 corresponds to a value of any of various indices, such as the number of white blood cells, LDH, and GPT, in case of the blood test. Also, the inspection result 1840 corresponds to determination made by a doctor based on the various indices. Also, in case of an image inspection, such as plain X-ray imaging or CT imaging, the inspection result 1840 includes pointer information to a captured image and pointer information to a report of an image diagnosis result. An image captured by an inspection is stored in the medical image data storage 203 of the medical information management system 200, in the format of DICOM.

Also, if the inspection type 1830 is an image inspection, such as plain X-ray, CT, MRI, or PET, medical image data of the image inspection is stored in a medical image database 2000 stored by the medical image data storage 203 of the medical information management system 200.

Figure 18:
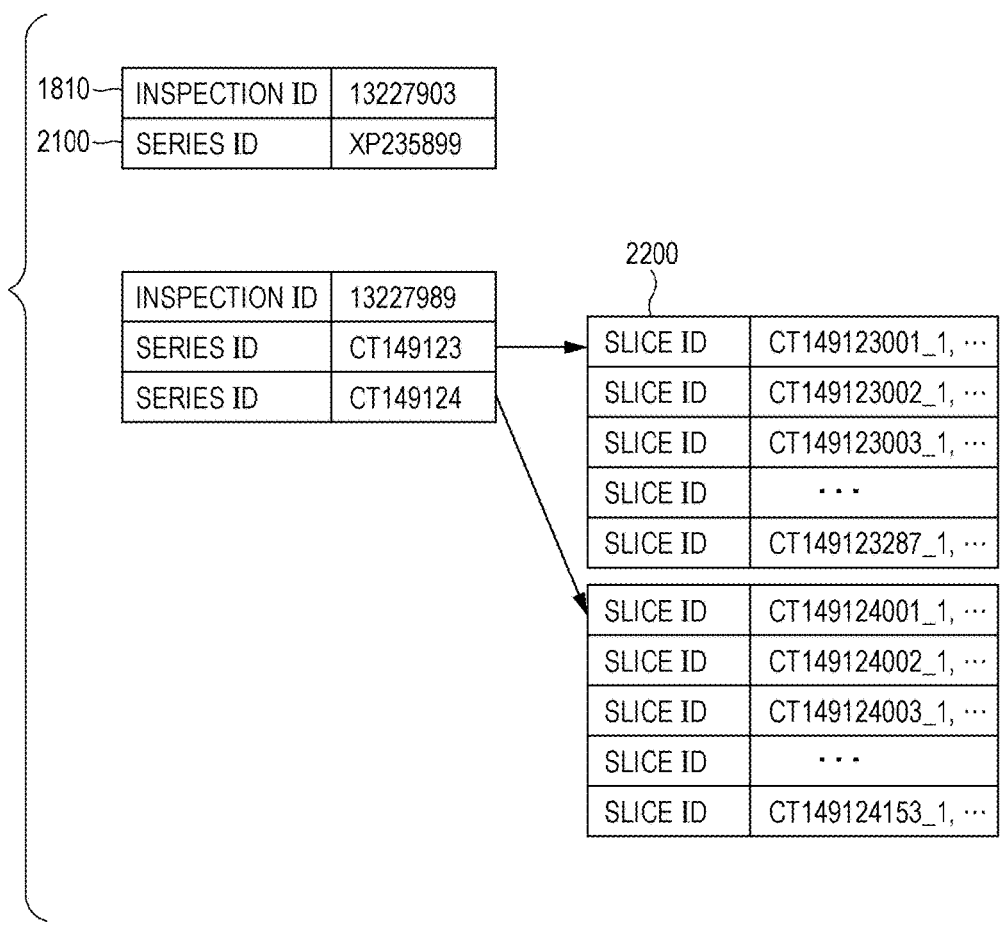
FIG. 18 illustrates a data configuration of a medical image database.

FIG. 18 illustrates a data configuration of the medical image database 2000. The medical image database 2000 includes inspection ID 1810 and series ID 2100. A plurality of types of imaging (for example, plain CT and contrast CT) may be performed in an inspection, and hence one inspection ID 1810 may be associated with a plurality of series IDs 2100. That is, series can be obtained by a number corresponding to the types of imaging.

Also, a series is obtained every condition for reconfiguring a captured image, in addition to the type of imaging. For example, if a captured image is reconfigured for a lung window and a mediastinal window, a series is obtained every condition. An image reconfigured for the lung window is displayed in a manner that blood vessels, a bronchus, alveoli, etc. are, enhanced. Also, an image reconfigured for the mediastinal window is displayed in a manner that mediastinum, such as blood vessels and lymph nodes are enhanced. The lung window and the mediastinal window can be obtained by reconfiguring an image obtained by one-time imaging. Hence, if imaging is performed 2 times for plain CT and contrast CT, and images are reconfigured for the lung window and the mediastinal window for each of two-time imaging, 2 series of the lung window and 2 series of the mediastinal window are obtained.

In case of an image inspection of CT and MRI, a plurality of slice images are acquired by one-time imaging. Hence, a series ID 2100 is associated with a plurality of slice IDs 2200. Since an inspection ID "13227989" in FIG. 18 is associated with 2 series IDs "CT149123" and "CT149124," it can be found that the 2 series of CT images are obtained from this inspection. Also, it is found that each of the series IDs "CT149123" and "CT149124" is associated with a plurality of slice IDs 2200.

In this case, branch numbers are added to the slice ID 2200, after underbars, such as CT149123001_1, CT149123001_2, etc. The branch numbers are associated with imaging conditions of slice images (described later) in advance. For example, "1" represents plain CT, "2" represents contrast CT, "3" represents T1-weighted, and "4" represents T2-weighted. The medical image database 2000 includes image data (not shown) of each imaging condition indicated by the slice ID 2200. Hence, by referencing the branch number, the display controller 104 can obtain a slice image captured under the imaging condition corresponding to the branch number.

If the inspection type 1830 is an image inspection, such as plain X-ray, CT, MRI, or PET, the diagnosis report 3000 as shown in FIG. 19 is stored in the diagnosis report manager 205 of the medical information management system 200. The diagnosis report 3000 has registered therein a diagnosis result of each inspection by a doctor. FIG. 19 illustrates a data configuration of the diagnosis report 3000.

The diagnosis report 3000 includes inspection ID 1810, remark 3100, and diagnosis 3200. The inspection ID 1810 is similar to the inspection ID 1810 shown in FIG. 17. Accordingly, the diagnosis report 3000 is associated with the inspection information 1800. The remark 3100 has registered therein wording indicative of a remark of a doctor on an inspection. The diagnosis 3200 has registered therein wording indicative of diagnosis by the doctor on the inspection.

Figure 20:
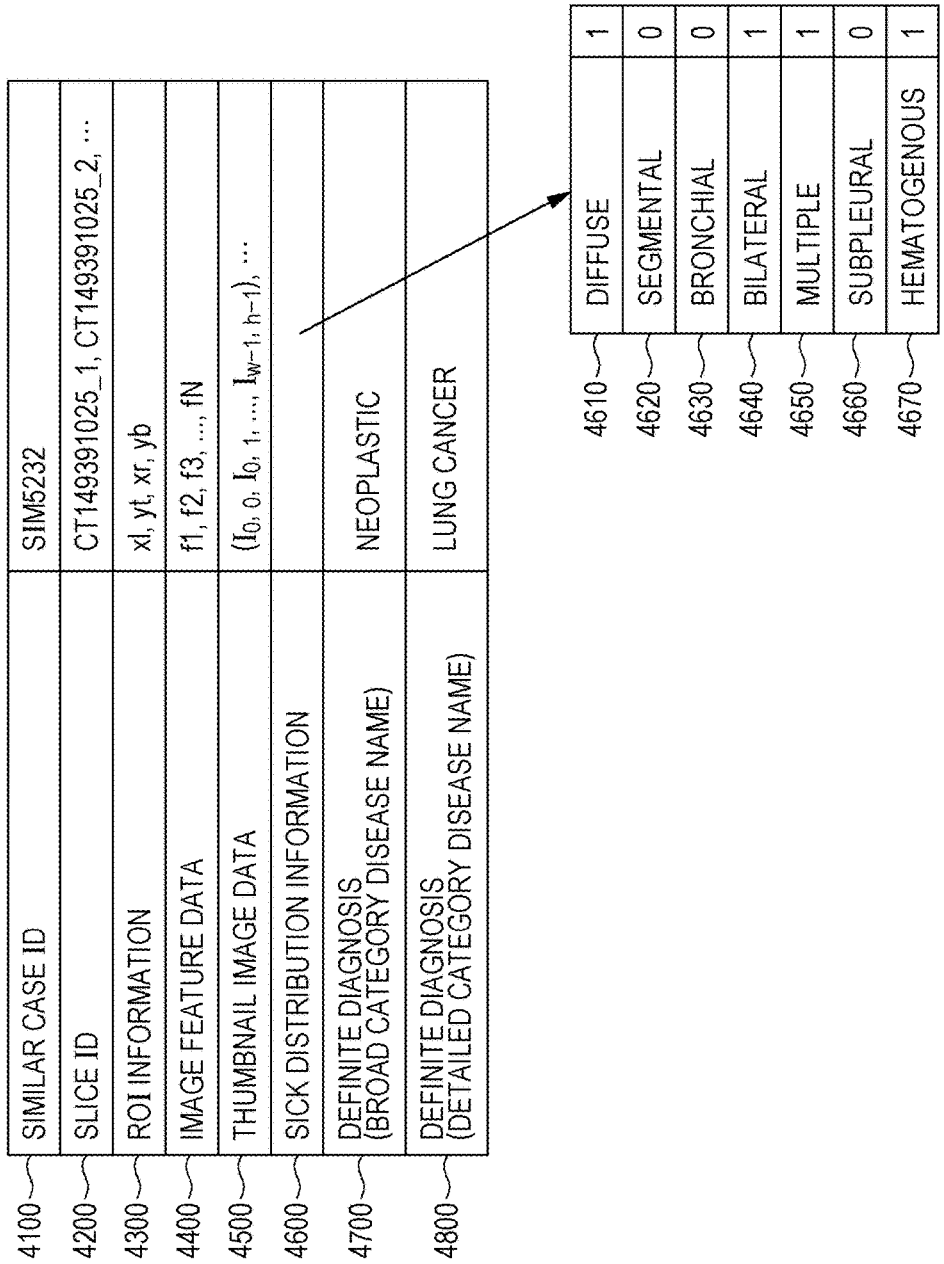
FIG. 20 illustrates a data configuration of similar case data.

FIG. 20 illustrates a data configuration of the similar case data 4000. The similar case data 4000 is data referenced when similar cases similar to a diagnosis target case are retrieved. A piece of similar case data 4000 is created for a similar case in a one-to-one relationship.

The similar case data 4000 is stored in the similar case data storage 301 of the case retrieval system 300 for each similar case. As shown in FIG. 20, the similar case data 4000 includes similar case ID 4100, slice ID 4200, ROI information 4300, image feature data 4400, thumbnail image data 4500, sick distribution information 4600, definite diagnosis (broad category disease name) 4700, and definite diagnosis (detailed category disease name) 4800.

The similar case ID 4100 is an identifier of the similar case data 4000. In this case, since a piece of similar case data is generated every region of interest set in a slice image of a similar case, the similar case ID 4100 can be also called identifier of a region of interest. In the example in FIG. 20, the similar case ID 4100 has a character string including "SIM" and a subsequent number.

The slice ID 4200 is an identifier of the slice image with the region of interest set, and is identical to the slice ID 2200 shown in FIG. 18. The ROI information 4300 is information indicative of the position of the region of interest set in the slice image. The ROI information 4300 is an example of sick portion information indicative of a sick portion in a similar medical image.

Figure 21:
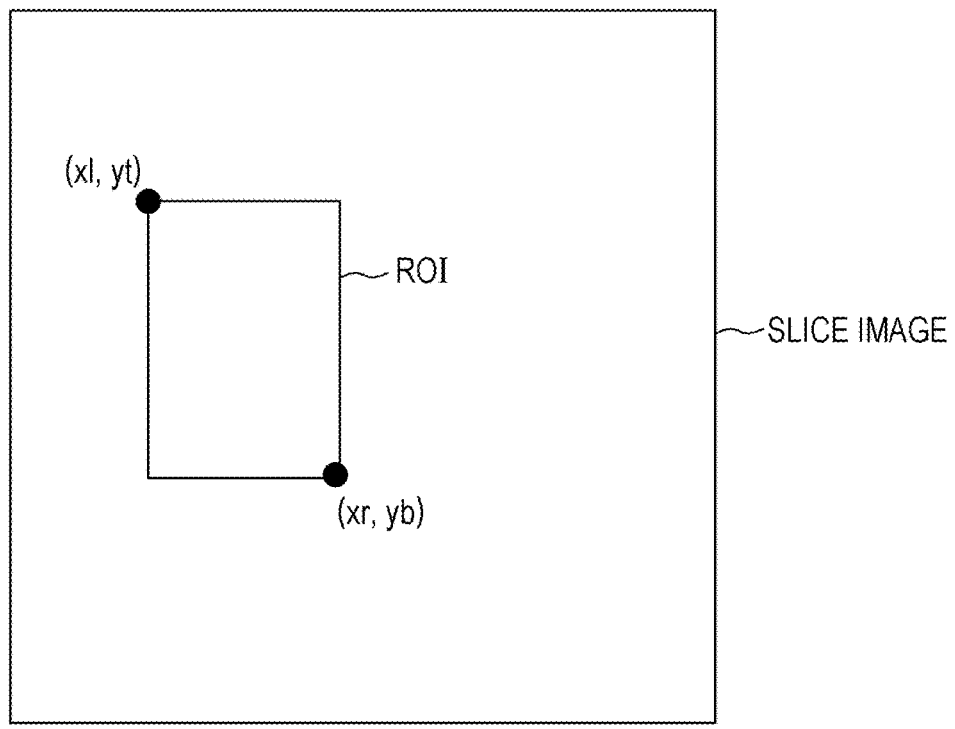
FIG. 21 schematically illustrates a region of interest set in a slice image.

FIG. 21 schematically illustrates a region of interest set in a slice image. In the example in FIG. 21, the region of interest is set in a rectangular shape. Hence, the ROI information 4300 includes 4 values of coordinates (xl, yt) at the upper left apex of the region of interest and coordinates (xr, yb) at the lower right apex of the region of interest. Of course, the region of interest may have a shape other than the rectangular shape. In such a case, a parameter that can uniquely specify the region is employed as ROI information 4300. For example, if the region of interest is a circle, the center coordinates and radius of the circle are employed as the ROI information 4300.

The image feature data 4400 is a feature value with a predetermined dimension (in this case, N-th dimension) extracted from the region of interest defined by the ROI information 4300. The thumbnail image data 4500 is image data of a thumbnail image generated to be displayed in the case display area 710 based on a slice image in DICOM format specified by a slice ID. In this case, in the thumbnail image data 4500, pixel values of a thumbnail image are arranged in the order of raster scanning directed from the upper left apex to the lower right apex of the thumbnail image. Although described above, a DICOM image obtained by CT inspection is an 11-bit image with 512×512 pixels (pixel values: −1000 to +1000). Owing to this, in this embodiment, to increase the speed of displaying a thumbnail image, a thumbnail image with 8-bit pixel values is created in advance by executing low resolution processing and gradation conversion processing on a DICOM image being an original of the thumbnail image, and the thumbnail image is registered in the similar case data 4000. The thumbnail image may be created by the medical information management system 200 and may be transmitted to the case retrieval system 300. Alternatively, the case retrieval system 300 may acquire the DICOM image from the medical information management system 200 and may create the thumbnail image. The thumbnail image data 4500 includes thumbnail image data for each imaging condition indicated by the slice ID 4200.

The sick distribution information 4600 is a distribution flag value (1: appropriate, 0: inappropriate) indicative of whether or not a target similar case is appropriate to one of the sick distributions expressed by the diffuse 4610 to hematogenous 4670.

The definite diagnosis (broad category disease name) 4700 is a broad category disease name determined on the target similar case. The definite diagnosis (broad category disease name) 4700 is used when similar cases are narrowed down to a broad category disease name.

The definite diagnosis (detailed category disease name) 4800 is a detailed category disease name determined on the target similar case. The definite diagnosis (detailed category disease name) 4800 is used when similar cases are narrowed down to a detailed category disease name.

The definite diagnosis (broad category disease name) 4700 includes a broad category disease name defined to uniquely correspond to the definite diagnosis (detailed category disease name) 4800, and is stored in the similar case data 4000 by using the correspondence.

In the definite diagnosis (detailed category disease name) 4800, the series ID 2100 is specified from the slice ID 2200 shown in FIG. 18 in the medical image data storage 203. Then, the inspection ID 1810 is specified from the specified series ID in the patient information storage 201, the corresponding patient information 1000 (FIG. 18) is specified from the inspection ID 1810, and the definite diagnosis 1900 of the corresponding patient is specified from the specified patient information 1000.

Image Selection to Similar Case Retrieval

A flow from start of reading by the information terminal 100 in association with the medical information management system 200 and the case retrieval system 300 to start of similar case retrieval is described.

Figure 22:
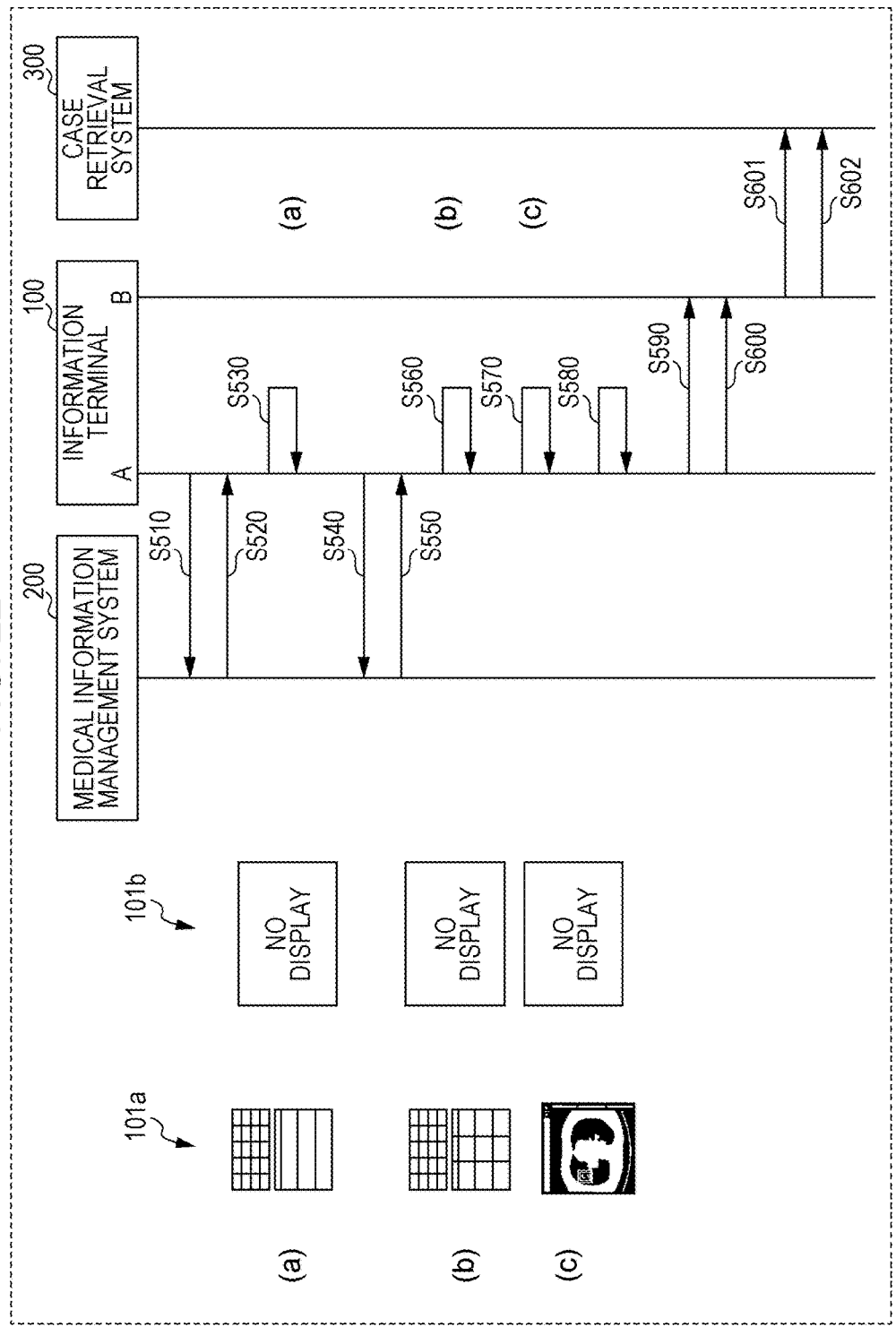
FIG. 22 is a sequence diagram showing processing after the information terminal acquires a diagnosis target case from the medical information management system until the information terminal makes a request for similar case retrieval to the case retrieval system and the case retrieval system receives the request for similar case retrieval.

FIG. 22 is a sequence diagram showing processing after the information terminal 100 acquires a diagnosis target case from the medical information management system 200 until the information terminal 100 makes a request for similar case retrieval to the case retrieval system 300 and the case retrieval system 300 receives the request for similar case retrieval. In FIG. 22, rectangles in 2 columns at the left of the sequence diagram indicate windows displayed on the displays 101a and 101b by processing of corresponding steps. Also, in FIG. 22, "A" of the information terminal indicates the medical information management application, and "B" indicates the similar case retrieval application. It is assumed that the medical information management application is activated in advance before this sequence is started.

The information terminal 100 receives a display request for a target inspection list for reading by a user (a doctor who executes reading) through the operation unit 102, and transmits the display request for the inspection list to the communication controller 206 of the medical information management system 200 through the input controller 103 and the communication controller 110 (S510).

The patient information manager 202 of the medical information management system 200 lists inspections on which image inspections have been executed but reading has not been ended, and hence generates the target inspection list for reading. The patient information manager 202 transmits the generated inspection list to the communication controller 110 of the information terminal 100 through the communication controller 206 (S520). The inspection list includes the patient information 1000 and the inspection information 1800 of the corresponding patient.

The display controller 104 of the information terminal 100 causes the display 101 to display the inspection list received by the communication controller 110 (S530).

In this case, the display 101a displays the inspection list, but the display 101b displays nothing.

FIG. 23 is a window view of the inspection list. The inspection list includes an area 800 that displays inspections on which reading has not been ended, and an area 810 that displays information relating to series included in the inspections. The area 800 includes columns of "patient ID," "patient name," "inspection date," "inspection ID," and "inspection type." The columns of "patient ID" and "patient name" indicate the patient ID 1100 and the name 1200 registered in the patient information 1000. The columns of "inspection date," "inspection ID," and "inspection type" indicate the inspection date 1820, the inspection ID 1810, and the inspection type 1830 registered in the inspection information 1800. The area 810 is an area for displaying the details of the inspection selected by the user in the area 800. The area 810 includes "series ID," "definition," and "image." In this case, since an inspection (corresponding to a row) is not selected in the area 800 by the user, the area 810 displays nothing.

The user selects an inspection for reading from the inspections displayed in the area 800. If the input controller 103 detects this selection, as shown in FIG. 22, the communication controller 110 transmits a display request for all series included in the inspection ID of the selected inspection, to the medical information management system 200 (S540).

If the communication controller 206 of the medical information management system 200 receives this display request, the patient information manager 202 references the medical image database 2000 shown in FIG. 18, acquires all slice images of all series included in the inspection ID designated in the display request, and transmits all slice images of all series to the information terminal 100 through the communication controller 206 (S550). For example, in the example in FIG. 18, if the inspection with the inspection ID "13227989" is selected by the user, all slice images included in series with the series IDs "CT149123" and "CT149124" are transmitted in S550.

If the communication controller 110 of the information terminal 100 acquires images of all series, the display controller 104 causes the area 810 to display a series list of listing information relating to all series included in the designated inspection ID (S560).

In this case, the area 810 of the inspection list displayed on the display 101a includes a series list of series corresponding to the inspection selected in the area 800, and the display 101b displays nothing.

FIG. 24 is a window view of the inspection list after an inspection is selected. In the area 800 in FIG. 24, the background of the selected row is highlighted. In the example in FIG. 24, an inspection of "PANA Taro" in the 2nd row is selected in the area 800. Owing to this, the area 810 displays "series ID," "definition," and "image" of the selected inspection. In the column of "series ID," a series ID associated with the inspection ID of the selected inspection in the medical image database 2000 is displayed, and in the column of "image," a thumbnail image of a slice image representing the displayed series ID is displayed. The slice image representing the series ID may employ an image at a predetermined slice position. The predetermined slice position may be a leading slice position or a center slice position. "Definition" indicates an imaging condition and a reconfiguration condition for the corresponding series. This "definition" is registered in association with the series ID in the medical image database 2000 in FIG. 18.

Figure 41:
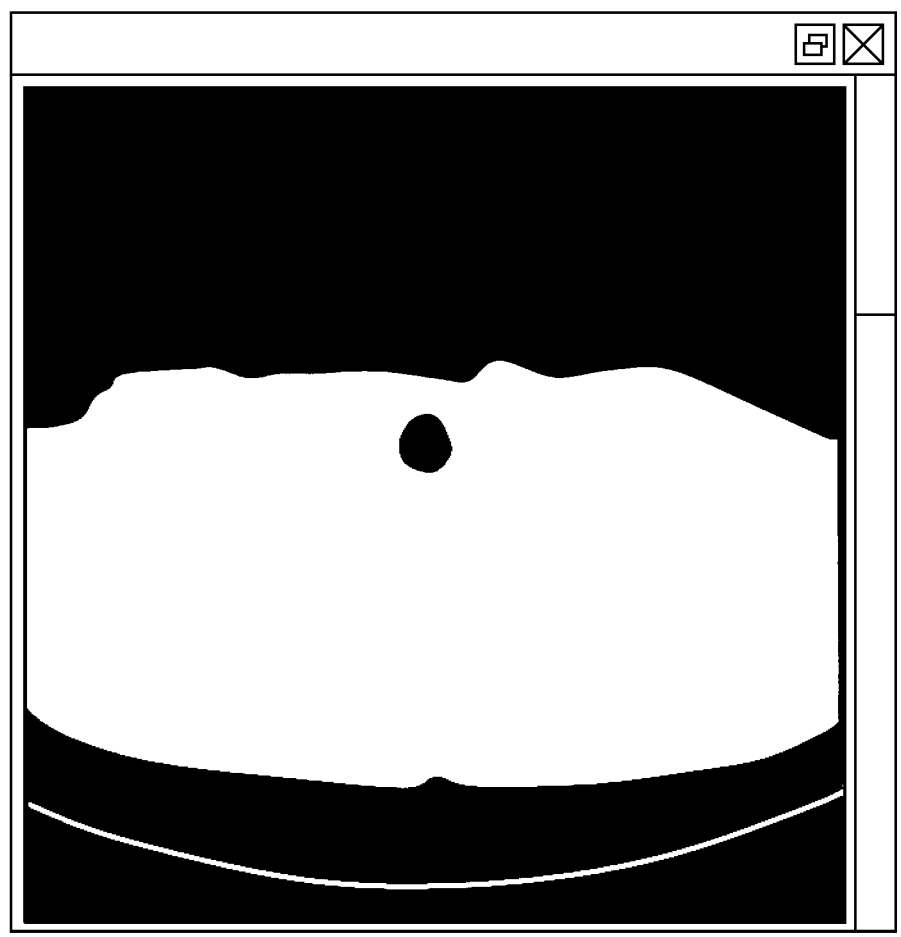
FIG. 41 illustrates a slice image displayed on the display when a user selects a series.

In the area 810, if the user selects a target series for reading and the input controller 103 detects the selection, the display controller 104 causes the display 101a to display a leading slice image of the selected series as shown in FIG. 41 (S570). FIG. 41 illustrates a slice image displayed on the display 101a when the user selects a series. FIG. 41 illustrates a leading slice in chest CT imaging, the slice image being at a shoulder position closer to the head as compared with the apex portion of a lung. The display controller 104 causes the display 101a to display all slice images of the selected series in a manner available for series-by-series advance. The display 101b displays nothing. For example, if the user positions the mouse pointer on the display 101a and inputs an operation of slice-by-slice advance by rotating the mouse wheel, the input controller 103 detects the operation. Then, the display controller 104 switches the slice image displayed on the display 101a to a slice image at another slice position in accordance with the rotation amount of the mouse wheel. The user executes image diagnosis while inputting the operation of slice-by-slice advance. If the user cannot make a decision on image diagnosis, the user activates the similar case retrieval application.

The similar case retrieval application may be activated if a predetermined shortcut key at the keyboard of the operation unit 102 is input. Alternatively, a menu of the medical image viewer may be displayed by a right-click with the mouse and a similar case retrieval menu in the menu may be designated. Thus, the similar case retrieval application may be activated. If the activation of the similar case retrieval application is instructed, the management of the information terminal 100 is handed over to the ROI manager 105. The information terminal 100 waits for reception of a region of interest (ROI).

Figure 25:
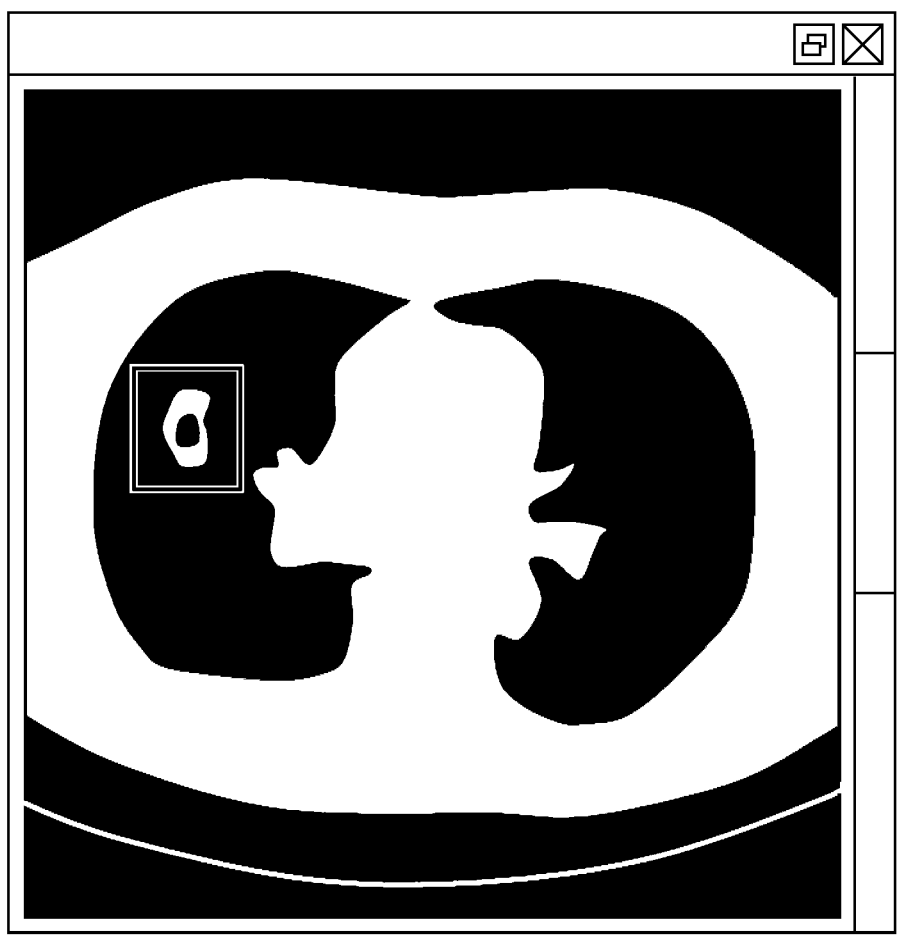
FIG. 25 illustrates an example of a window after a region of interest is set for a sick portion.

The user sets a region of interest (ROI) at a sick portion in the slice image displayed on the display 101a through the operation unit 102 (S580). As shown in FIG. 21, the user inputs coordinates at the upper left apex of the region of interest by a left click with the mouse. The user drags the mouse toward the lower right while holding the left click and then releases the left click. Thus, the user may input the lower right apex of the region of interest. FIG. 25 illustrates an example of a window after the region of interest is set for the sick portion.

When the input controller 103 detects the operation of setting the region of interest, the ROI manager 105 receives the coordinate data at the upper left apex and the lower right apex of the region of interest from the input controller 103, and generates ROI information from the received coordinate data. Then, the ROI manager 105 transmits the generated ROI information to the communication controller 110 (S590).

At the same time, the ROI manager 105 transmits a slice image of a diagnosis target case to the communication controller 110 (S600). In this case, a slice image (a retrieval query image) with a region of interest set by the user in the series selected by the user is transmitted among the slice images of all series received by the information terminal 100 from the medical information management system 200 in S550.

Then, the communication controller 110 receives the ROI information transmitted form the ROI manager 105, and transmits the ROI information to the communication controller 304 of the case retrieval system 300 (S601).

At the same time, the communication controller 110 receives the slice image transmitted form the ROI manager 105, and transmits the slice image to the communication controller 304 of the case retrieval system 300 (S602).

The slice image itself is transmitted in S600 and S601; however, the slice ID of the slice image may be transmitted. In this case, the case retrieval system 300, which has received the slice ID, may designate the slice ID and acquire the slice image from the medical information management system 200.

Similar Case Retrieval to Initial Display

Processing from when the case retrieval system 300 executes similar case retrieval to when the information terminal 100 initially displays a similar case retrieval result is described.

Figure 26:
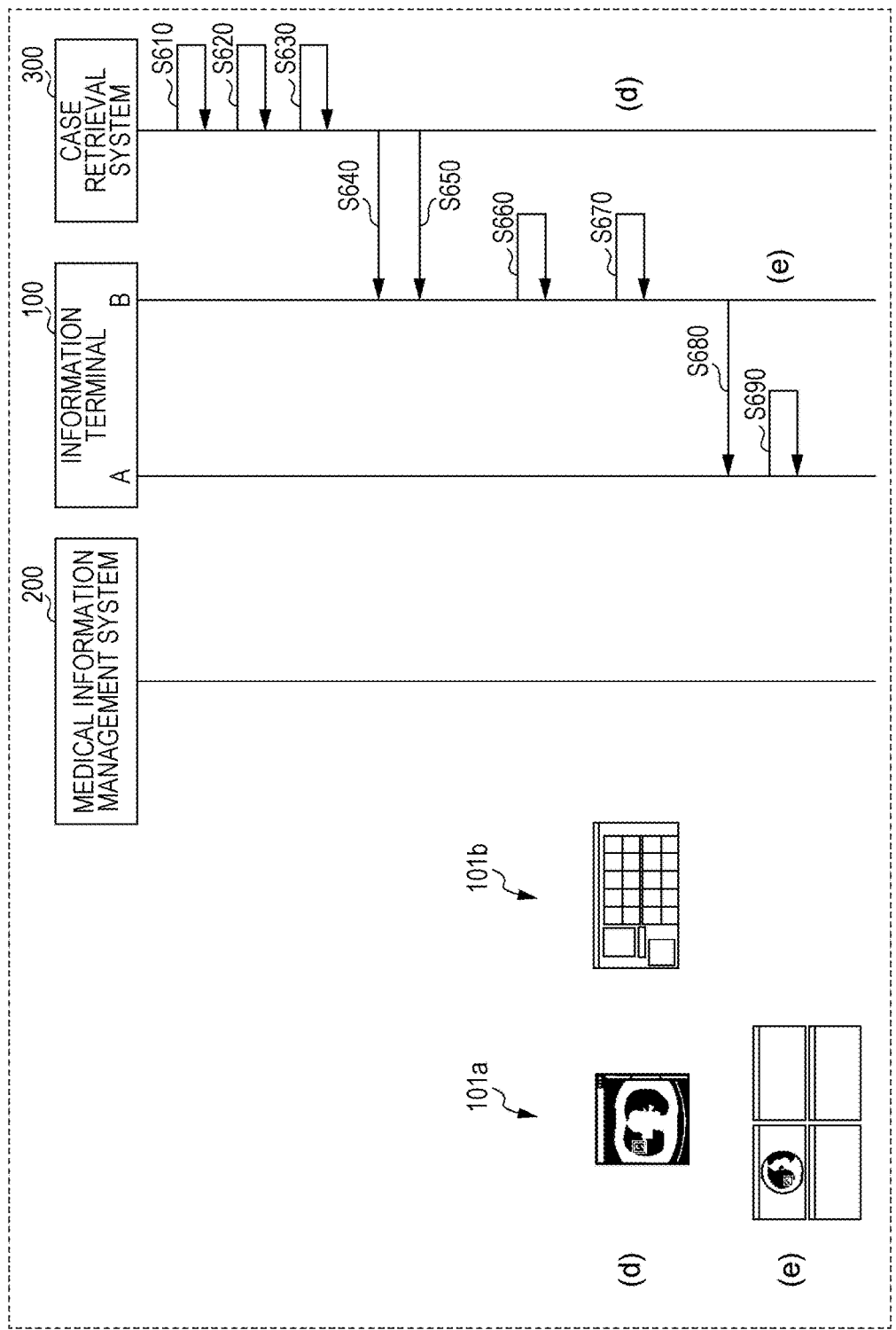
FIG. 26 is a sequence diagram showing processing after the case retrieval system receives the request for similar case retrieval until the case retrieval system returns a similar case retrieval result to the information terminal.

FIG. 26 is a sequence diagram showing processing after the case retrieval system 300 receives a request for similar case retrieval until the case retrieval system 300 returns a similar case retrieval result to the information terminal 100.

The image feature extractor 302 of the case retrieval system 300 extracts an image feature with a plurality of predetermined dimensions from the region of interest set in the retrieval query image (S610).

The "image feature" may be an image feature relating to an organ or the shape of a sick portion in a medical image, or an image feature relating to a brightness distribution. For example, 'NEMOTO Mitsutaka, SHIMIZU Akinobu, HAGIHARA Yoshihiro, KOBATAKE Hidefumi, and NAWANO Shigeru, "Improvement of Tumor Detection Performance in Mammograms by Feature Selection from a Large Number of Features and Proposal of Feature Selection Method," IEICE TRANSACTIONS on Information and Systems D-II, Vol. J88-D-II, No. 2, pp. 416 to 426, February, 2005' describes using image features with 490 dimensional parameters. This embodiment, for example, employs the image features described in the aforementioned document. However, this is merely an example, and other image features may be used.

The similar case retriever 303 compares the image feature extracted by the image feature extractor 302 with an image feature of each of similar cases stored in the similar case data storage 301 (S620). In this case, the similar case retriever 303 compares both image features by calculating the distance between image feature data extracted from the retrieval query image and the image feature data 4400 registered in the similar case data 4000 (FIG. 20) stored for each similar case in the similar case data storage 301.

Then, the similar case retriever 303 sorts similar cases at distances equal to or smaller than a predetermined threshold in the ascending order of distance, and determines a target similar case for transmission (S630). Then, the communication controller 304 transmits the similar case ID 4100, slice ID 4200, ROI information 4300, thumbnail image data 4500, sick distribution information 4600, definite diagnosis (broad category disease name) 4700, and definite diagnosis (detailed category disease name) 4800 of the similar case determined as the target similar case for transmission among the similar case data 4000 stored in the similar case data storage 301, and the distance calculated by the similar case retriever 303 to the information terminal 100 (S640).

Hereinafter, processing of generating the initial basic window K2 (FIG. 6) displaying the similar case retrieval result is executed. Described first is management information that is used when the layout area 720 is generated in the initial basic window K2.

The communication controller 304 of the case retrieval system 300 transmits layout information to the information terminal 100 (S650). The layout information is information for designating the number of rows and the number of columns of display boxes forming the layout area 720.

Then, if the communication controller 110 of the information terminal 100 receives the layout information, the display box manager 106 registers the number of rows and the number of columns of the display boxes designated by the transmitted layout information in the display box management information 4410 (FIG. 35), and registers the slice ID of the retrieval query image in the display box management information 4410 (FIG. 35) (S660).

FIG. 35 illustrates a data configuration of the display box management information 4410. The display box management information 4410 includes a table 4411 having registered therein the number of rows and the number of columns, and a table 4412 having registered therein a slice ID of a slice image displayed in each display box. The display box manager 106 registers the number of rows and the number of columns designated by the layout information transmitted from the case retrieval system 300 in the column of the number of rows and the number of columns in the table 4411. Also, in this embodiment, the thumbnail image of the retrieval query image is displayed in the upper left display box 721 among the 4 display boxes 721 to 724. Hence, the display box manager 106 registers the slice ID of the retrieval query image transmitted from the medical information management system 200 in the item in the 1st row and 1st column of the table 4412.

A default value of the number of rows and the number of columns of the display boxes forming the layout area 720 is previously determined by the case retrieval system 300. The default value of the number of rows and the number of columns is, for example, 2 rows by 2 columns. Hence, "2 rows by 2 columns" are registered in the display box management information 4410 shown in FIG. 35.

Then, referring back to FIG. 26, the display controller 104 generate the initial basic window K2 in which the similar case retrieval result is displayed, by using the similar case data transmitted in S640 and the display box management information 4410 saved in S660 (S670).

In this case, the display 101b displays the basic window K2 shown in FIG. 6. Also, the display 101a displays the retrieval query image.

Figure 27:
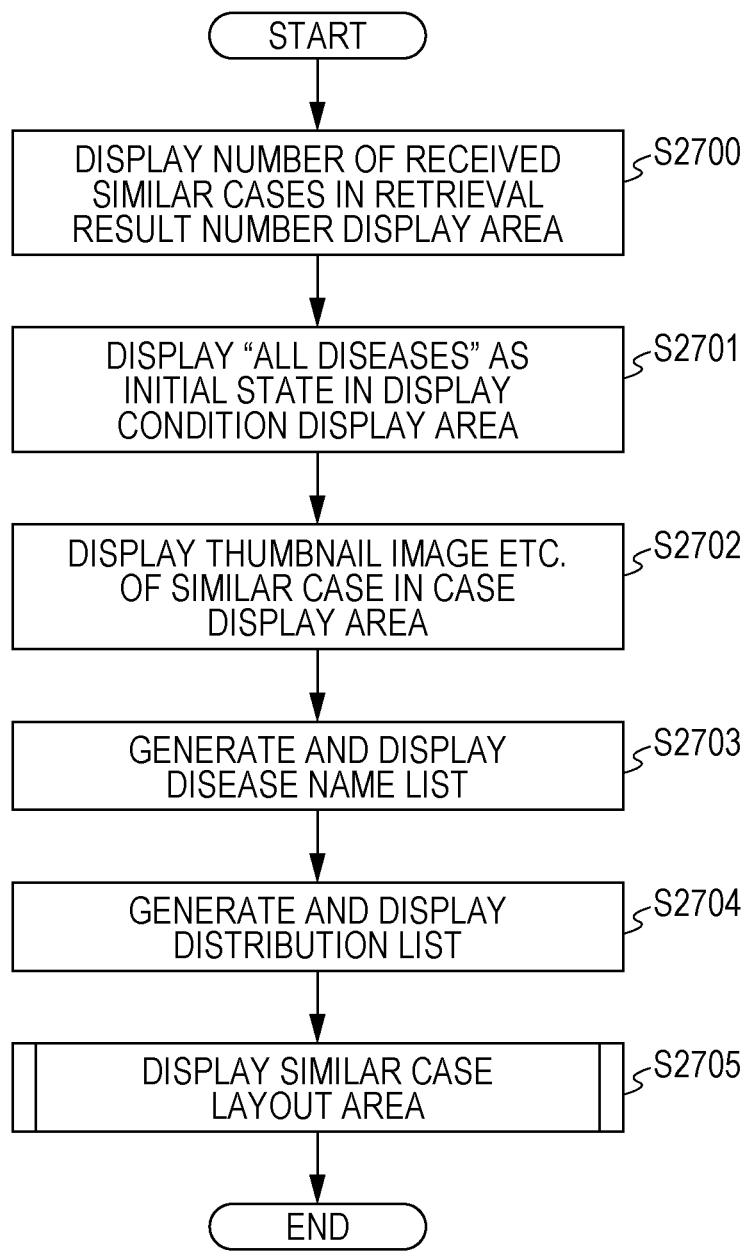
FIG. 27 is a flowchart showing the details of processing of generating an initial basic window shown in S670 in FIG. 26.

FIG. 27 is a flowchart showing the details of processing of generating the initial basic window K2 shown in S670 in FIG. 26.

In S2700, the display controller 104 counts the number of similar cases received in S640 in FIG. 26, and causes the retrieval result number display area 713 to display the count value.

Then, in S2701, the display controller 104 causes the display condition display area 714 to display "all diseases." In this case, the display condition display area 714 displays "all diseases" because the user does not execute narrowing down to disease name or sick distribution in the initial basic window K2.

Then, in S2702, the display controller 104 displays thumbnail images of similar cases in the case display area 710 by a number of similar cases whose thumbnail images can be displayed in the case display area 710 among the similar cases received in S640 in FIG. 26, and displays the definite diagnosis and similarity in association with each of the thumbnail images.

The maximum value of the number of similar cases that can be displayed in the case display area 710 is 20 in the example in FIG. 6. The maximum value is previously determined. Also, the maximum value may be desirably changed by the user. If the number of similar cases received in S640 in FIG. 26 is larger than the maximum value, the display controller 104 causes the scroll bar 715 being long in the vertical direction to be displayed at the right end of the case display area 710. Accordingly, the user can browse the thumbnail images of the similar cases hidden in the initial basic window K2 by moving the scroll bar 715.

Then, in S2703, a disease name list is generated and displayed. The disease name list is generated from the similar cases received in S640 in FIG. 26. The disease name list is a list in which the similar cases received in S640 are classified by definite diagnosis disease name.

In this case, it is assumed that the number of similar cases received in S640 is NC cases. The disease name list manager 108 generates the disease name list by using the definite diagnosis (broad category disease name) 4700 and the definite diagnosis (detailed category disease name) 4800 registered in the similar case data 4000 of each of the NC cases. The disease name list manager 108 manages the generated disease name list as table-form data shown in FIG. 29.

FIG. 29 illustrates a data configuration of the disease name list generated in S2703 in FIG. 27. The disease name list includes columns of "disease name ID," "broad category disease name," "detailed category disease name," "number of cases," and "similar case ID," "Disease name ID" is an identifier applied to each definite diagnosis disease name. In this case, a disease name ID is applied to a combination of a broad category disease name and a detailed category disease name.

"Broad category disease name" is a definite diagnosis disease name indicated by the definite diagnosis (broad category disease name) 4700 registered in the similar case data 4000. "Detailed category disease name" is a definite diagnosis disease name indicated by the detailed diagnosis (detailed category disease name) 4800 registered in the similar case data 4000. The "number of cases" is the number of similar cases corresponding to the definite diagnosis disease name indicated by "disease name ID." "Similar case ID" is a similar case ID indicative of a similar case corresponding to the disease name indicated by "disease name ID."

The disease name list manager 108 extracts the definite diagnosis (broad category disease name) 4700 and the definite diagnosis (detailed category disease name) 4800 for all the similar case data 4000 received in S640, and the similar case data 4000 having the same definite diagnosis (broad category disease name) 4700 and the same definite diagnosis (detailed category disease name) 4800 is classified as similar cases having the same definite diagnosis disease name. Then, the disease name list manager 108 counts the number of the similar cases having the same definite diagnosis disease name, and registers the number in "number of cases" in the record of the corresponding definite diagnosis disease name. Also, the disease name list manager 108 registers the similar case IDs of the similar cases having the same definite diagnosis disease name in "similar case ID" in the record of the corresponding definite diagnosis disease name.

In the example in FIG. 29, a disease ID "DIS528" is given to a definite diagnosis disease name having a broad category disease name being "neoplastic" and a detailed category disease name being "lung cancer." Since the number of similar cases corresponding to the definite diagnosis disease name is 10 cases, 10 is registered in the column of "number of cases" in the corresponding record, and similar case IDs "SIM258," "SIM551," "SIM1209," "SIM2341," and so forth being similar cases corresponding to the definite diagnosis disease name are registered in the column of "similar case ID" in the corresponding record.

The display controller 104 generates the disease name list display area 730 by using the generated disease name list, and causes the display 101 to display the disease name list display area 730.

FIGS. 30, 31, and 32 respectively illustrate a first display example, a second display example, and a third display example of the disease name list display area 730. As shown in FIG. 30, in the first display example, similar cases obtained as the result of similar case retrieval are listed in association with the numbers of cases in the descending order of the numbers of cases of the detailed category disease names.

As shown in FIG. 31, in the second display example, similar cases obtained as the result of similar case retrieval are listed in association with the numbers of cases in the descending order of the numbers of cases of the broad category disease names.

As shown in FIG. 32, in the third display example, similar cases obtained as the result of similar case retrieval are listed in association with the numbers of cases in the descending order of the numbers of cases of the broad category disease names, and listed in association with the numbers of cases in the descending order of the numbers of cases of the detailed category disease names included in each of the broad category disease names. In this case, the definite diagnosis disease names are expressed in a hierarchical structure of the broad category disease names and the detailed category disease names.

Figure 33:
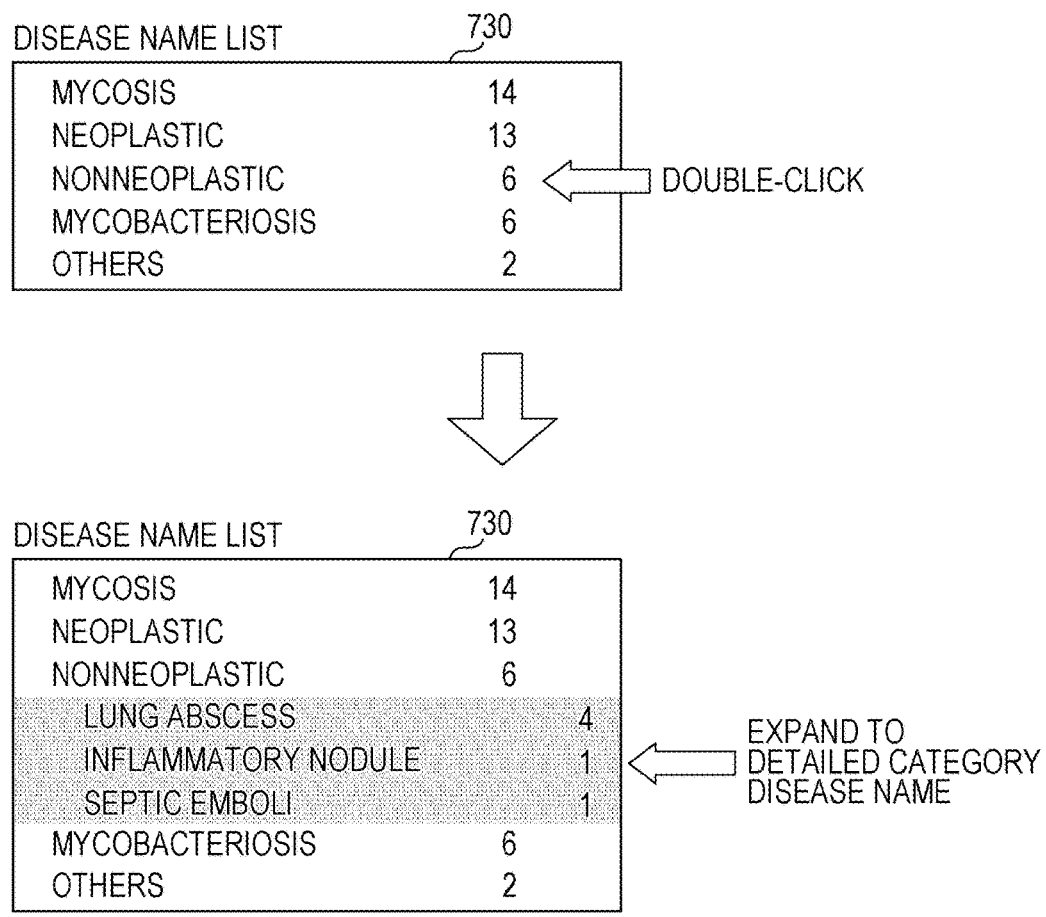
FIG. 33 illustrates a window transition of the disease name list display area shown in FIG. 31.

FIG. 33 illustrates a window transition of the disease name list display area 730 shown in FIG. 31. As shown in the upper section in FIG. 33, if the input controller 103 detects an operation of selecting one broad category disease name from the listed broad category disease names by the user, the display controller 104 displays detailed category disease names belonging to the selected broad category disease name in the descending order of the number of cases in association with the number of cases as shown in the lower section in FIG. 33. The user may select desirable one broad category disease name by double-clicking or single-clicking the desirable one broad category disease name included in the listed broad category disease names in the disease name list display area 730. In the example in FIG. 33, since nonneoplastic is double-clicked, detailed category disease names belonging to nonneoplastic are listed.

In the lower section in FIG. 33, if the area in which the detailed category disease names are listed is double-clicked or single-clicked by the user, the display controller 104 may hide the detailed category disease names displayed in the corresponding area.

The display controller 104 may judge the detailed category disease names belonging to the broad category disease name by referencing the disease name list (FIG. 29). For example, in the example in FIG. 29, since aspergillosis and cryptococcosis are associated with mycosis, the display controller 104 may determine that aspergillosis and cryptococcosis belong to mycosis.

Referring back to FIG. 27, in S2704, a distribution list is generated and displayed. The distribution list is generated from the similar cases received in S640. The distribution list is a list in which the similar cases received in S640 are classified by sick distribution.

The disease name list manager 108 generates the distribution list by using the sick distribution information 4600 registered in the similar case data 4000 of each of the NC cases. The distribution list manager 109 manages the generated distribution list as table-form data shown in FIG. 34.

FIG. 34 illustrates a data configuration of the distribution list generated in S2704 in FIG. 27. The distribution list includes columns of "distribution name," "number of cases," and "similar case ID." "Distribution name" includes names of a plurality of predetermined sick distributions, such as diffuse and segmental. The "number of cases" is the number of similar cases corresponding to a sick distribution. "Similar case ID" is a similar case ID indicative of a similar case corresponding to a sick distribution.

The distribution list manager 109 extracts the sick distribution information 4600 for all the similar case data 4000 received in S640, counts the number of sick distributions with the distribution flag values being 1 (appropriate), and registers the count value in the column of "number of cases" in the record of the corresponding sick distribution. Also, the distribution list manager 109 registers the similar case IDs of the similar cases with the distribution flag values being 1 in the column of "similar case ID" in the record of the corresponding sick distribution.

In the example in FIG. 34, since the number of similar cases corresponding to diffuse is 3 cases, and hence, 3 is registered in the column of "number of cases" in the record of diffuse. Also, similar case IDs "SIM2521," "SIM4123," and "SIM5225" are registered in the column of "similar case ID" in the record of diffuse.

The display controller 104 generates the distribution list display area 750 by using thus generated distribution list, and causes the display 101 to display the distribution list display area 750.

The distribution list display area 750 generated by using the distribution list shown in FIG. 34 is illustrated in FIG. 11. In FIG. 34, since the numbers of cases of segmental and subpleural are 0, in FIG. 11, the segmental 752 and the subpleural 756 are displayed in the inactive state, and sick distributions other than segmental and subpleural are displayed in the active state because the numbers of similar cases are each 1 or larger.

Referring back to FIG. 27, in S2705, the layout area 720 is displayed. The display controller 104 executes this processing.

Figure 28:
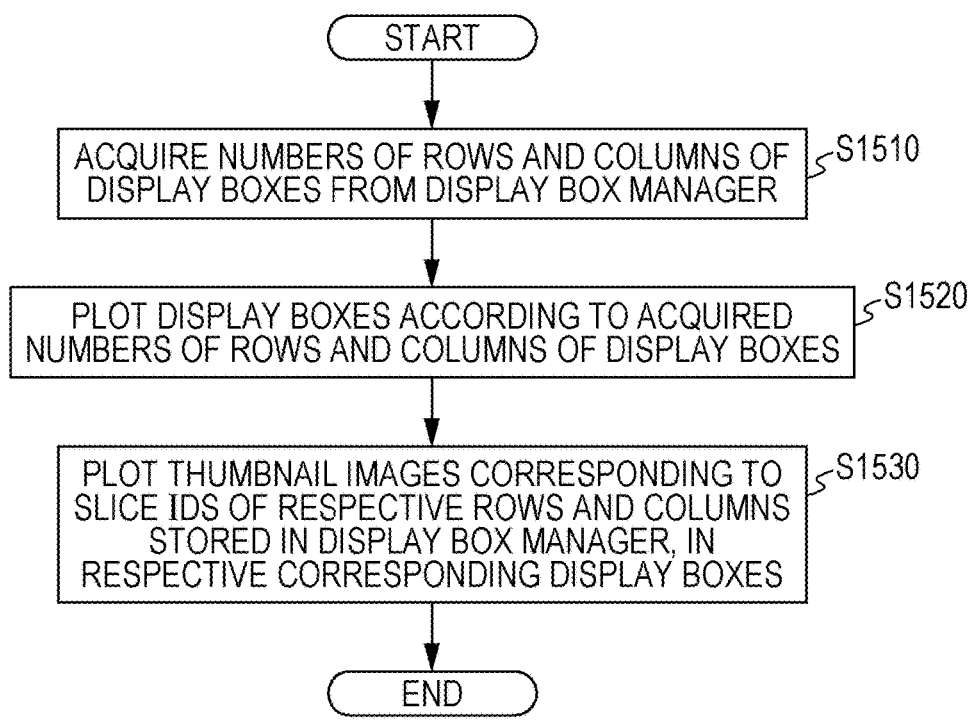
FIG. 28 is a flowchart showing processing in S2705 in FIG. 27.

FIG. 28 is a flowchart showing the processing in S2705 in FIG. 27. In S1510, the display controller 104 acquires the number of rows and the number of columns of the display boxes forming the layout area 720 from the display box management information 4410 set in S660. In the example of the display box management information 4410 in FIG. 35, 2 rows by 2 columns are set as the number of rows and the number of columns. Accordingly, information "2 rows by 2 columns" is acquired.

In S1520, the display controller 104 causes the display boxes to be plotted to meet the number of rows and the number of columns of the display boxes acquired in S1510.

In S1530, the display controller 104 specifies the slice IDs of respective display boxes from the display box management information 4410, and causes thumbnail images corresponding to the specified slice IDs to be plotted in the respective corresponding display boxes.

In the example in FIG. 35, the slice ID of a diagnosis target case is stored in the display box in the 1st row and 1st column. Hence, the display controller 104 generates a thumbnail image from the slice image of the diagnosis target case transmitted in S600 in FIG. 22, and causes the generated thumbnail image to be plotted in the display box 721.

In this state, since the residual display boxes (the display boxes 722, 723, and 724 in the 1st row and 2nd column, the 2nd row and 1st column, and the 2nd row and 2nd column) store no slice ID, the display controller 104 causes the display boxes to display nothing. In the display boxes, thumbnail images of similar cases are displayed by processing described later.

Referring back to FIG. 26, the communication controller 110 transmits the display box management information 4410 stored in the display box manager 106 to the display controller 104 (S680).

Then, the display controller 104 activates the medical image viewers in the same display state and layout as the display state and layout of the layout area 720 (S690).

Figure 36:
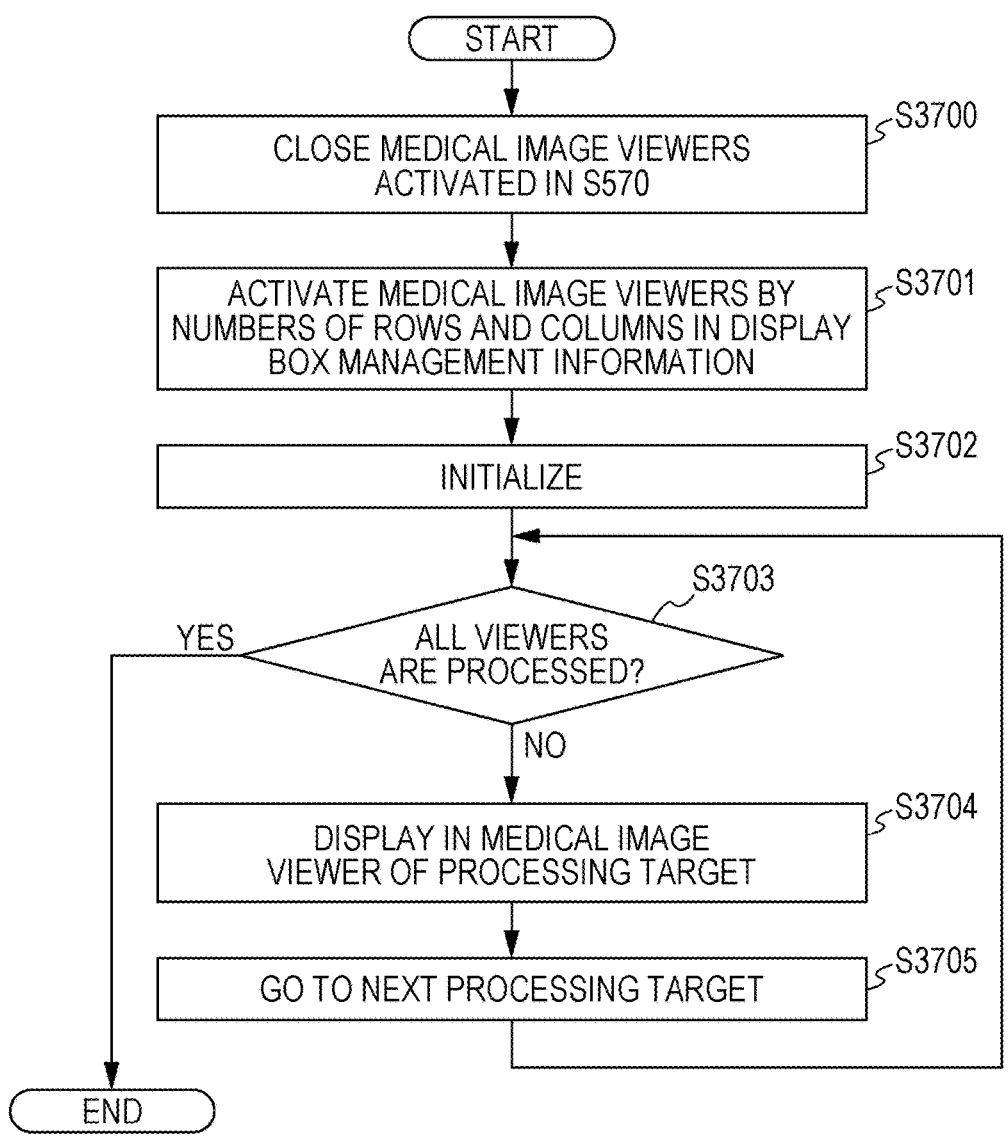
FIG. 36 is a flowchart showing processing of activating a medical image viewer.

FIG. 36 is a flowchart showing processing of activating the medical image viewers.

In S3700, the display controller 104 closes the medical image viewers activated in S570 in FIG. 22.

In S3701, the display controller 104 activates medical image viewers by the amount corresponding to the display boxes registered in the display box management information

4410, in the layout with the number of rows and the number of columns registered in the display box management information 4410. In the display box management information 4410 in FIG. 35, 4 display boxes in 2 rows by 2 columns are registered. Hence, as shown in FIG. 5, the display controller 104 activates the 4 medical image viewers 610 to 640 in 2 rows by 2 columns.

In S3702, the display controller 104 initializes a variable for specifying a medical image viewer to be a processing target. Since the medical image viewer in the 1st row and 1st column is a processing target, the variable is set in 1 row and 1 column.

In S3703, the display controller 104 checks whether or not processing on all (in this case, 4) medical image viewers is completed. If all processing is completed (YES in S3703), the processing is ended. If an unprocessed medical image viewer is left (NO in S3703), the processing goes to S3704.

In S3704, the display controller 104 causes the medical image viewer being the processing target to display a slice image having a slice ID associated with the row number and the column number set as the variable, and associates a series including the slice ID with the medical image viewer.

For example, in the example of the display box management information 4410 shown in FIG. 35, the slice ID "CT12353515_1" is registered in the 1st row and 1st column. Hence, the slice ID "CT12353515_1" is displayed in the medical image viewer 610. Also, the display controller 104 plots a rectangle indicating a region of interest set in an initially displayed slice image to overlap the slice image. The series including the slice ID registered in the 1st row and 1st column is already acquired in S550 in FIG. 22. Also, the region of interest is already set in S580 in FIG. 22.

Referring back to FIG. 36, in S3705, the next medical image viewer is set as a medical image viewer of a processing target. Next to the 1st row and 1st column, for example, a processing target is set in the 1st row and 2nd column, the 2nd row and 1st column, and then the 2nd row and 2nd column.

In S3704 in the second loop, the medical image viewer 620 in the 1st row and 2nd column is a processing target. However, no slice ID is associated in the display box management information 4410 in FIG. 35 except the 1st row and 1st column. Owing to this, the display controller 104 executes no processing on the medical image viewer in the 1st row and 2nd column, and leaves that medical image viewer blank. This can be applied to the medical image viewers 630 and 640 in the 2nd row and 1st column and the 2nd row and 2nd column.

When the flowchart is ended, the display 101a displays the basic window K1 in the initial state shown in FIG. 5. In the medical image viewer 610 in the 1st row and 1st column (upper left), the retrieval query image is displayed, and the rectangle indicative of the region of interest is plotted on the retrieval query image in an overlap manner.

Figure 37:
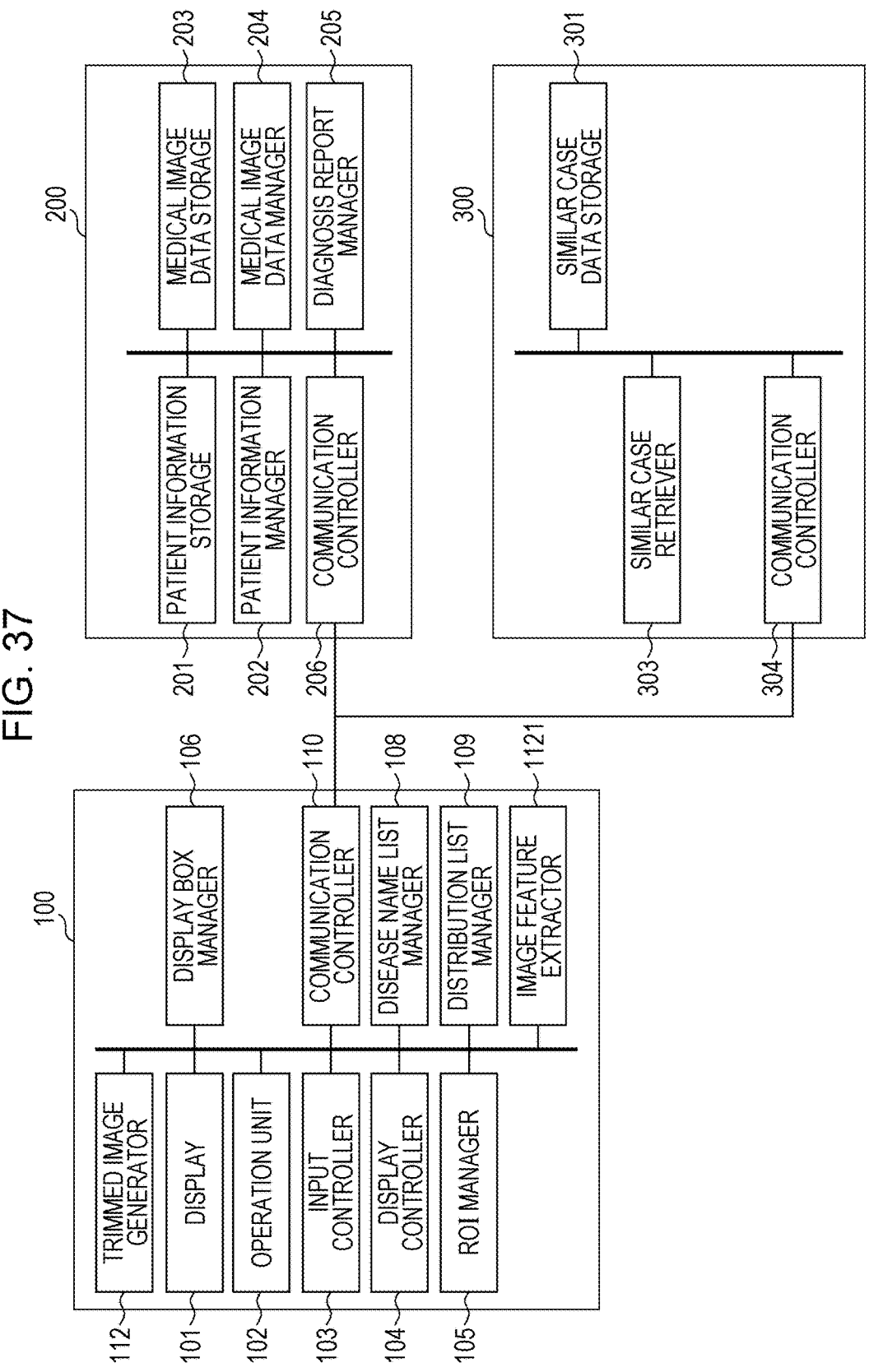
FIG. 37 is a block diagram of an information terminal, a medical information management system, and a case retrieval system when an embodiment in which the case retrieval system extracts an image feature is employed.

In this case, the example in which the case retrieval system 300 extracts an image feature is described. However, the information terminal 100 may extract the image feature. FIG. 37 is a block diagram of the information terminal 100, the medical information management system 200, and the case retrieval system 300 when an embodiment in which the case retrieval system 300 extracts an image feature is employed.

This embodiment differs from FIG. 2 in that an image feature extractor 1121 is added to the information terminal 100, and the image feature extractor 302 is omitted from the case retrieval system 300.

Figure 38:
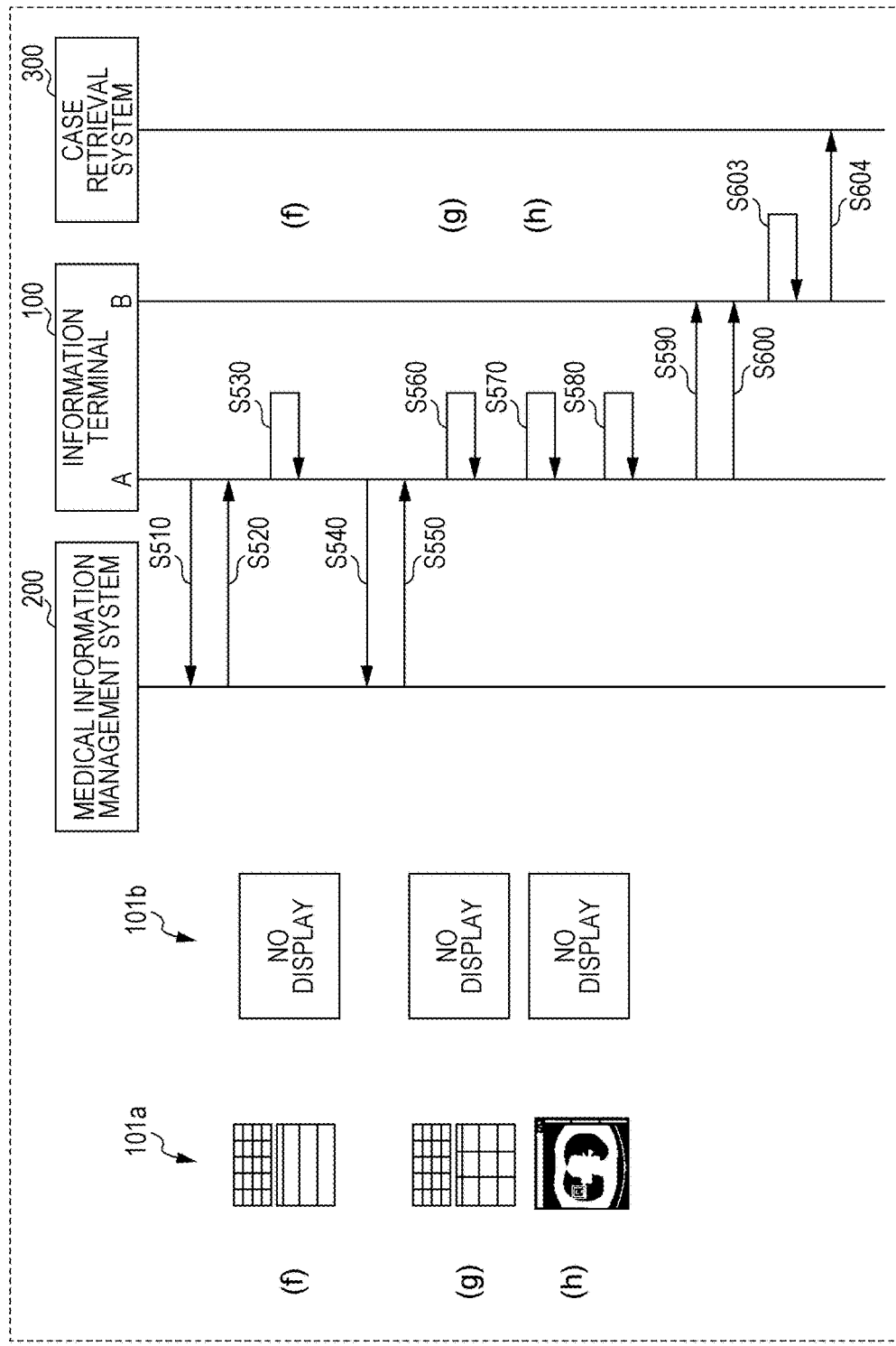
FIG. 38 is a sequence diagram showing processing after the information terminal acquires a diagnosis target case from the medical information management system until the case retrieval system receives a request for similar case retrieval.

FIG. 38 is a sequence diagram showing processing after the information terminal 100 acquires a diagnosis target case from the medical information management system 200 until the case retrieval system 300 receives a request for similar case retrieval.

In FIG. 38, the sequence differs from FIG. 22 in that, after the ROI manager 105 executes the processing of transmitting the slice image being the diagnosis target case to the communication controller 110 (S600), the information terminal 100 extracts an image feature (S603), and the information terminal 100 transmits the extracted image feature to the case retrieval system 300 (S604). The processing content of executing the image feature (S604) is similar to the case in which the case retrieval system 300 extracts the image feature.

Figure 39:
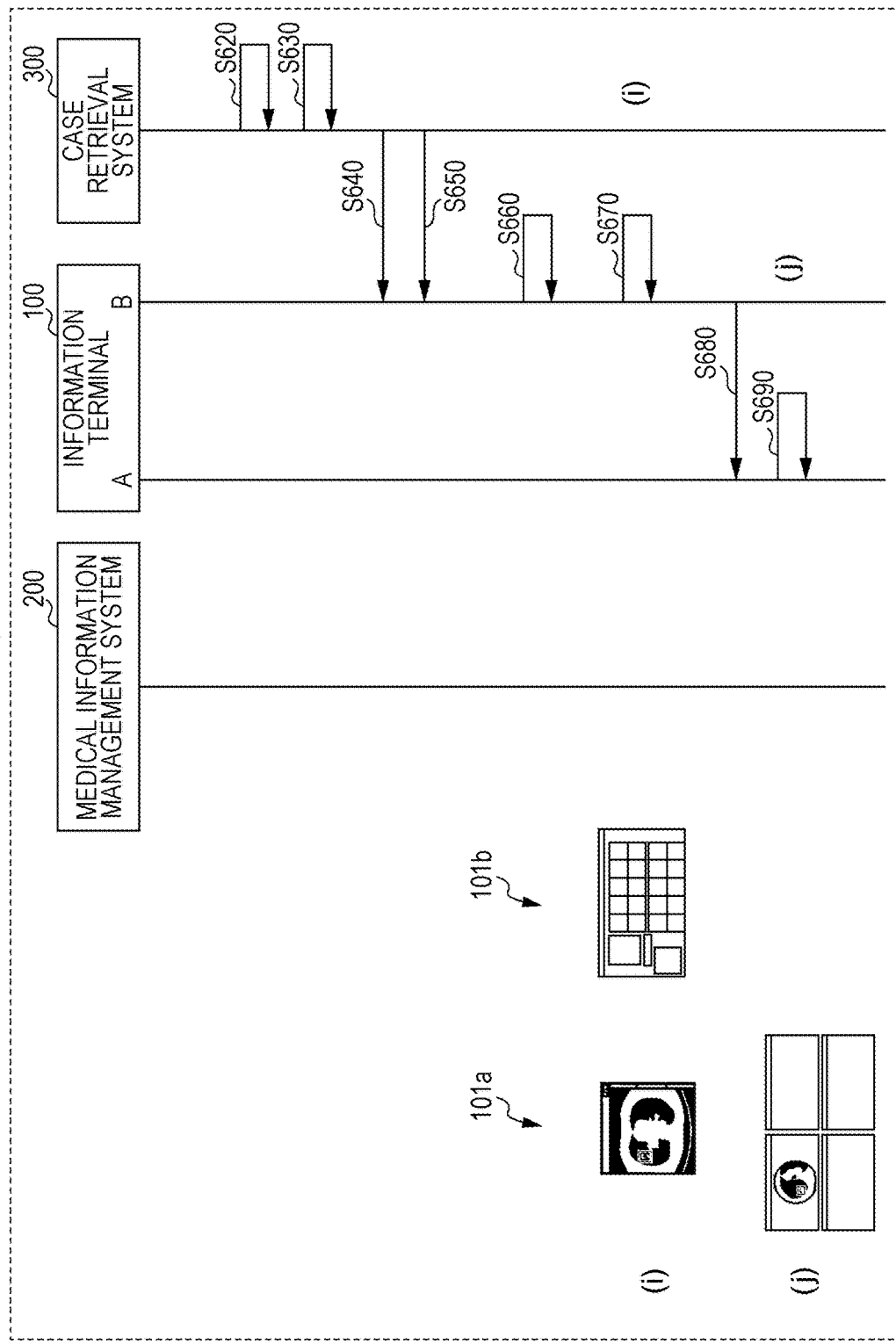
FIG. 39 is a sequence diagram showing processing after the case retrieval system receives the request for similar case retrieval until the case retrieval system returns a similar case retrieval result to the information terminal.

FIG. 39 is a sequence diagram showing processing after the case retrieval system 300 receives the request for similar case retrieval until the case retrieval system 300 returns a similar case retrieval result to the information terminal 100. The sequence differs from FIG. 26 in that, since the information terminal 100 extracts the image feature, the extraction of the image feature (S610) in FIG. 26 is omitted in FIG. 39.

Figure 40:
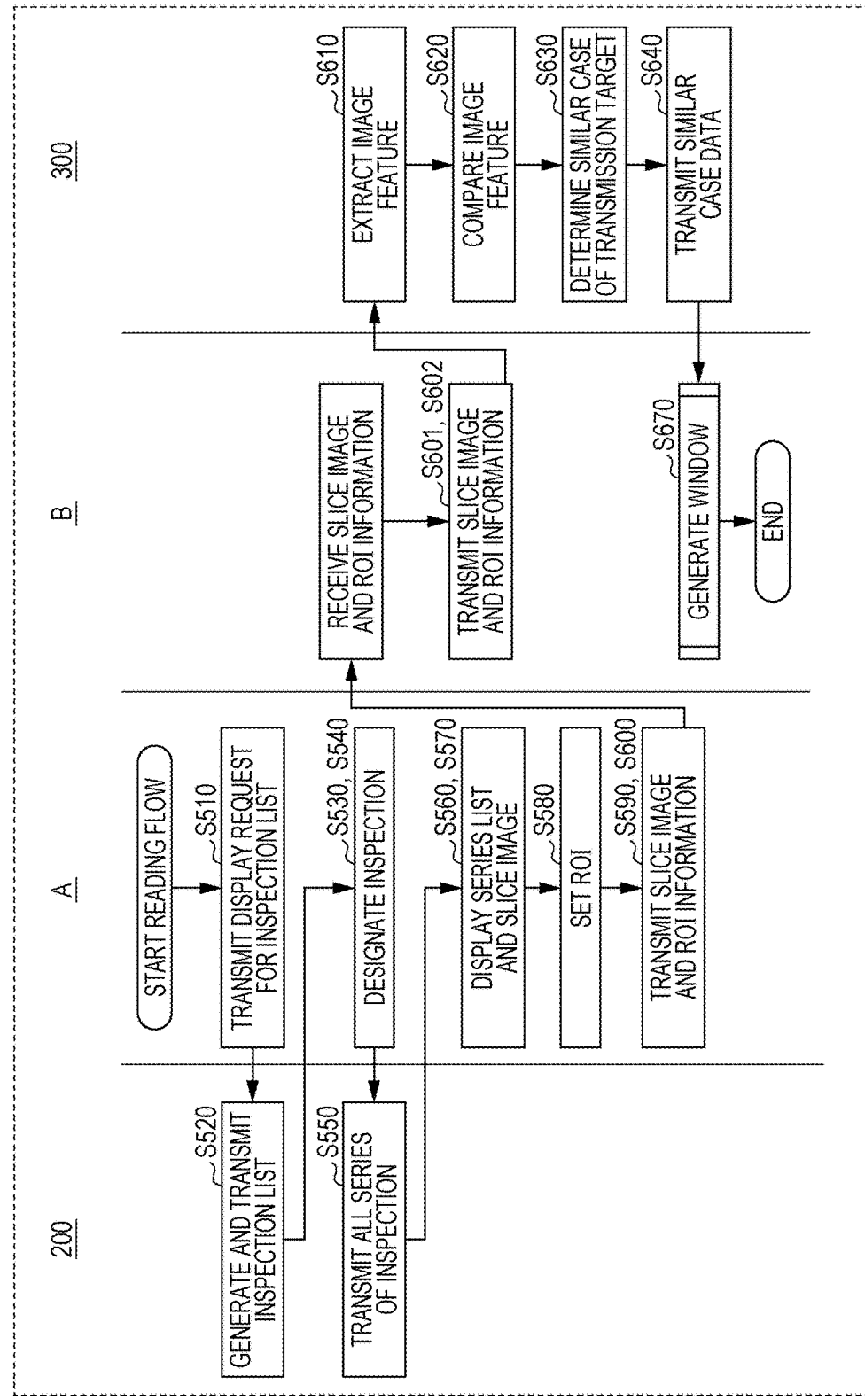
FIG. 40 is a sequence diagram when the sequence diagrams in FIGS. 22 and 26 are focused in the level of application.

Described next are the processing of the information terminal 100, the processing of the medical information management system 200, and the processing of the case retrieval system 300 when the sequence diagrams in FIG. 22 and FIG. 26 are focused in the level of application. FIG. 40 is a sequence diagram when the sequence diagrams in FIGS. 22 and 26 are focused in the level of application. In FIG. 40, the same reference sign is applied to the same processing in FIG. 22.

In FIG. 40, "A" indicates a medical information management application executed by the information terminal 100, and "B" indicates a similar case retrieval application executed by the information terminal 100. Hereinafter, the medical information management application is referred to as "application A" and the similar case retrieval application is referred to as "application B."

The application A receives a display request for a target inspection list for reading from a user, and transmits the display request to the medical information management system 200 (S510). When the medical information management system 200 receives the display request for the inspection list, the medical information management system 200 lists inspections on which image inspections have been executed but reading has not been ended, generates the target inspection list for reading, and transmits the inspection list to the application A (S520).

The application A which has received the inspection list displays the inspection list on the display 101 as shown in FIG. 23. When the user selects one inspection from the inspection list (S530), the application A transmits a display request for the selected inspection to the medical information management system 200 (S540).

The medical information management system 200 which has received the inspection request transmits all slice images in all series included in inspection IDs designated by the display request (S550).

Then, the application A displays a series list listing information relating to all series included in the designated inspection ID as shown in FIG. 24 (S560).

Then, when the user selects a target series for reading from the series list, the application A causes a slice image at a first slice position in the selected series to be displayed in the medical image viewer 610 (S570). At this time, the user inputs an operation of slice-by-slice advance to display a desirable slice image in the medical image 610.

Then, the application A receives an operation of setting a region of interest from the user in the slice image displayed in the medical image viewer 610 (S580).

Then, the application A generates ROI information indicative of the region of interest set by the user, and transmits the ROI information and the slice image with the region of interest set (the slice image of the diagnosis target case) to the application B (S590, S600).

Then, when the application B receives the slice image of the diagnosis target case and the ROI information, transmits the slice image and the ROI information to the case retrieval system (S601, S602).

When the case retrieval system 300 receives the slice image and the ROI information, the case retrieval system 300 executes the processing from S610 to S640 similarly to FIG. 26.

Then, the application B generates an initial basic window by using the similar case data transmitted in S640 and the display box management information 4410 (S670). Then, the application B executes the processing in S670 the details of which are shown in FIG. 27.

Initial Display to Change in Display Number of Images

Described next is a flow after the information terminal 100 initially displays the similar case retrieval result until the user inputs an operation of changing the display number of thumbnail images with the information terminal 100 and the information terminal 100 displays a trimmed thumbnail image again.

Figure 53:
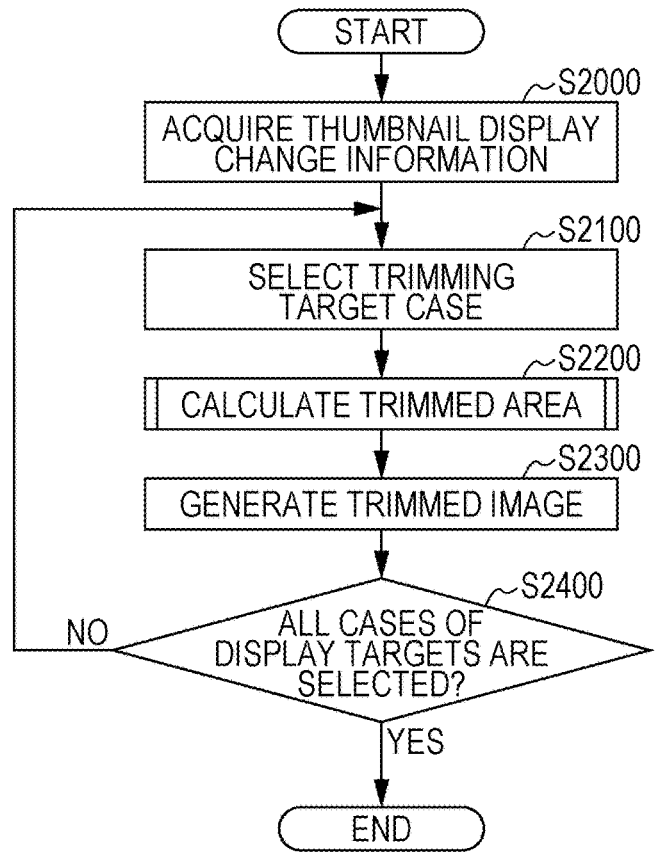
FIG. 53 is a flowchart showing a flow of processing after a similar case retrieval result is initially displayed in the information terminal until thumbnail images being the similar case retrieval result are trimmed.

FIG. 53 is a flowchart showing a flow of processing after the information terminal 100 initially displays the similar case retrieval results until thumbnail images being the similar case retrieval results are trimmed and displayed. All the processing is entirely executed in the information terminal 100.

Acquire Operation Information: S2000

In S2000, the operation unit 102 receives an operation of changing the display number of thumbnail images to be displayed in the case display area 710, and the input controller 103 of the information terminal 100 acquires thumbnail display change information according to the received operation. In this embodiment, the display number of thumbnail images to be displayed in the case display area 710 is determined by the operation amount of the scroll bar 1700 shown in FIG. 42. Hence, the thumbnail display change information is determined by the operation amount of the scroll bar 1700 in FIG. 42. To be specific, as shown in an upper section in FIG. 55, a moving distance d of the scroll bar 1700 may be employed as thumbnail display change information.

Select and Acquire Trimming Target Case: S2100

In S2100, the trimmed image generator 112 selects desirable one similar case as a trimming target case from the similar cases acquired by similar case retrieval, and acquires the similar case ID 4100 of the selected similar case. The trimmed image generator 112 selects a similar case with the highest similarity to the retrieval query image, and then a similar case with next similarity to the retrieval query image. In this way, the trimmed image generator 112 may select trimming target cases one by one in the descending order of similarity.

Calculate Trimmed Area: S2200

Figure 54:
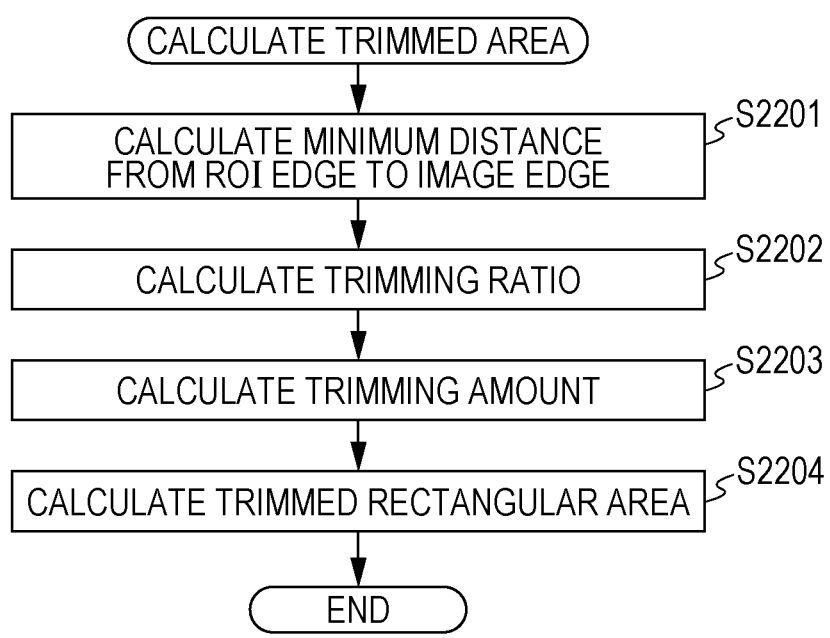
FIG. 54 is a flowchart showing processing of calculating a trimmed area shown in S2200 in FIG. 53.
Figure 55:
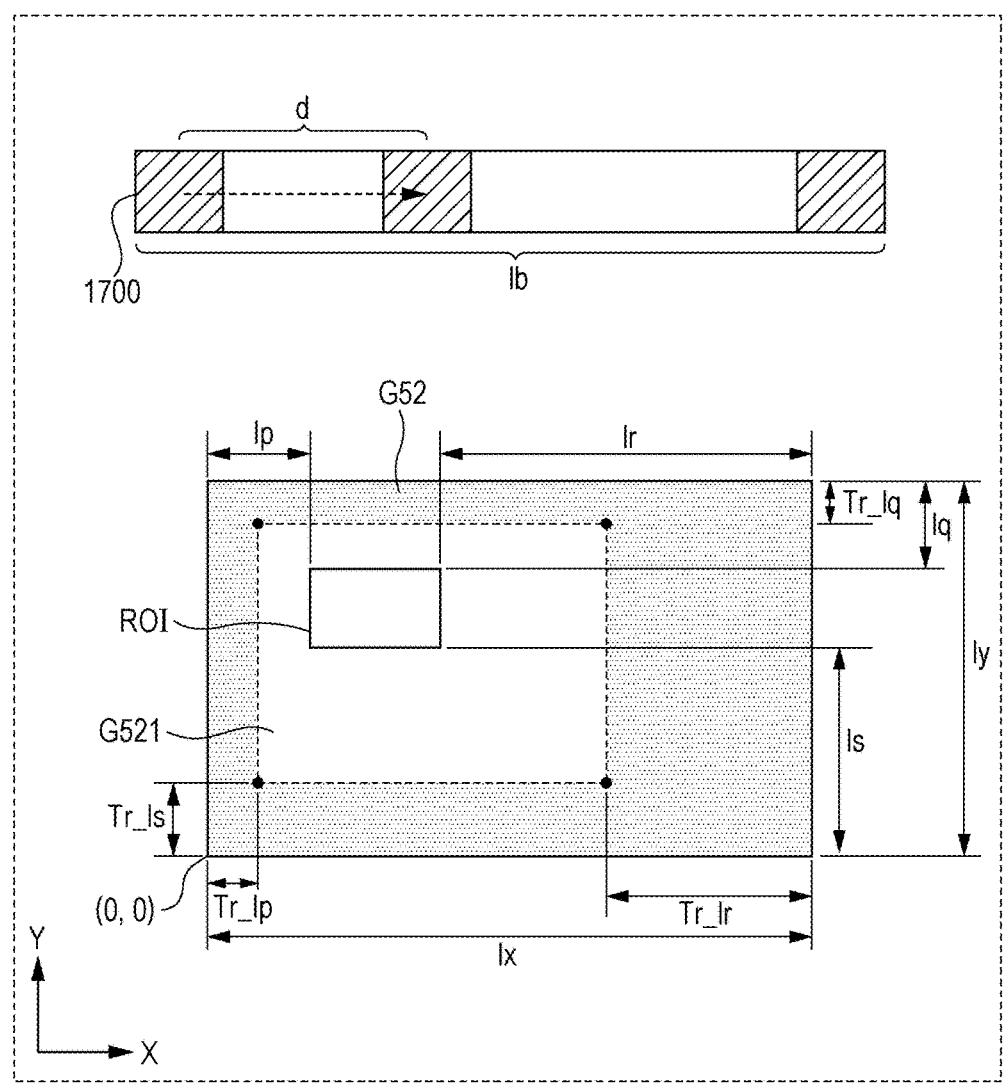
FIG. 55 illustrates the processing of calculating the trimmed area.

Then, in S2200, a trimmed area is calculated for the thumbnail image being the one trimming target case selected in S2100. FIG. 54 is a flowchart showing processing of calculating the trimmed area in S2200 in FIG. 53. FIG. 55 illustrates the processing of calculating the trimmed area. The processing of calculating the trimmed area is described below with reference to FIG. 54 and FIG. 55. In FIG. 55, the upper section indicates the scroll bar 1700 shown in FIG. 42, and the lower section indicates a thumbnail image G52.

In S2201, the trimmed image generator 112 calculates distances between respective edges of ROI and respective edges of the thumbnail image G52 in the thumbnail image being the trimming target case selected in S2100 in FIG. 53. To be specific, as shown in FIG. 55, the trimmed image generator 112 calculates distances lp, lr, lq, and ls between the left edge, right edge, upper edge, and lower edge of the ROI and the left edge, right edge, upper edge, and lower edge of the thumbnail image.

Then, in S2202, the trimmed image generator 112 calculates a trimming ratio by using the thumbnail display change information acquired in S2000 shown in FIG. 53. In this example, the thumbnail display change information corresponds to the moving distance d of the scroll bar 1700. The trimming ratio is a ratio calculated in S2201 for trimming the respective distances lp, lr, lq, and ls. As shown in the upper section in FIG. 55, when Ib denotes the total length of the scroll bar 1700 and d denotes the moving distance of the scroll bar 1700, the trimmed image generator 112 calculates a trimming ratio Rt by using, for example, the following expression:

$Rt=d/Ib$.

Then, in S2203, the trimmed image generator 112 calculates trimming amounts for the respective edges of the thumbnail image. The trimming amount is a distance by which the thumbnail image is trimmed from each edge. The trimmed image generator 112 calculates trimming amounts Tr for the respective edges by multiplying the distances (lp, lr, lq, and ls) between the respective edges of the ROI and the respective edges of the thumbnail image calculated in S2201 by the trimming ratio Rt. Referring to FIG. 55, the trimmed image generator 112 calculates a trimming amount Tr_ls by the distance ls between the lower edge of the ROI and the lower edge of the thumbnail image G52 by using, for example, the following expression:

$Tr\_ls=ls*Rt$.

The trimmed image generator 112 similarly calculates trimming amounts Tr_lq, Tr_lp, and Tr_lr for the distance lq between the upper edges of the ROI and the thumbnail image G52, the distance lp between the left edges of the ROI and the thumbnail image G52, and the distance lr between the right edges of the ROI and the thumbnail image G52 by using the following expressions:

$Tr\_lq=lq*Rt$, $Tr\_lp=lp*Rt$, and $Tr\_lr=lr*Rt$.

In S2204, the trimmed image generator 112 calculates a trimmed area G521 by using the trimming amount Tr calculated in S2203. The trimmed area G521 indicates a rectangular trimmed image area in the thumbnail image G52.

Then, the trimmed image generator 112 trims the respective edges of the thumbnail image G52 by the trimming amount Tr calculated in S2203, generates the residual area as the trimmed area G521, and calculates the coordinates of the generated trimmed area G521.

As shown in FIG. 55, it is assumed that the origin (0, 0) of the thumbnail image G52 is set at the lower left apex, the Y axis thereof is set to increase its value upward in the vertical direction, and the X axis thereof is set to increase its value rightward in the horizontal direction.

The trimmed image generator 112 sets the upper edge of the trimmed area G521 at a position defined by shifting the upper edge of the thumbnail image G52 in the −Y direction by the trimming amount Tr_lq, the left edge of the trimmed area G521 at a position defined by shifting the left edge of the thumbnail image G52 in the X direction by the trimming amount Tr_lp, the right edge of the trimmed area G521 at a position defined by shifting the right edge of the thumbnail image G52 in the −X direction by the trimming amount Tr_lr, and the lower edge of the trimmed area G521 at a position defined by shifting the lower edge of the thumbnail image G52 in the Y direction by the trimming amount Tr_ls. Then, the trimmed image generator 112 generates the trimmed area G521 by removing an area (an area indicated with gray color in FIG. 55) other than the set trimmed area G521 from the thumbnail image G52.

Then, the trimmed image generator 112 may calculate coordinates of the 4 apexes of the trimmed area G521 as the coordinates of the trimmed area G521.

In the example in FIG. 55, since the lower left apex of the thumbnail image G52 is set at the origin, for example, the coordinates of the upper left apex of the trimmed area G521 is expressed as (lp*Rt, Iy−lq*Rt), that is, (Tr_lp, Iy−Tr_lq).

The above-described processing from S2201 to S2204 is executed on the thumbnail image G52 of each trimming target case, and the thumbnail image G52 of each trimming target case is sequentially trimmed.

Generate Trimmed Image: S2300

Referring back to FIG. 53, in S2300, the trimmed image generator 112 extracts the trimmed area G521 calculated in S2200 from the thumbnail image G52, and generates the trimmed area G521. To be specific, the trimmed area G521 calculated in S2200 is cut out from the thumbnail image G52 being the trimming target case selected in S2100, and hence the trimmed image G521 is generated.

Judge all Selection: S2400

In S2400, the trimmed image generator 112 judges whether or not all target similar cases for displaying are selected as trimming target cases among all similar cases acquired by similar case retrieval in S2100. If not all target similar cases for displaying are selected as trimming target cases (NO in S2400), the trimmed image generator 112 returns the processing to S2100. Then, the trimmed image generator 112 selects the next trimming target case in S2100, and acquires the similar case ID of the selected trimming target case. In contrast, if all target similar cases for displaying are selected as trimming target cases (YES in S2400), the processing is ended.

Then, the display controller 104 arranges the trimmed similar medical images in the case display area 710 in the descending order of similarity, and displays the trimmed similar medical images on the display 101.

In the example in FIG. 43, the display controller 104 arranges the trimmed similar medical images in the case display area 710 in the descending order of similarity in a matrix form with a predetermined interval. Accordingly, the number of similar medical images that can be displayed at once in the case display area 710 is increased.

All target similar cases for displaying represent similar cases by the number of images that can be displayed at once in the case display area 710. If the thumbnail display change information is figured out, the trimming ratio Rt is figured out. Hence, a rough display size of a thumbnail image after trimming is figured out. Then, if the rough display size of the thumbnail image after trimming is figured out, the number of similar cases that can be displayed at once in the case display area 710 is figured out. Owing to this, the trimmed image generator 112 may hold a table in which the thumbnail display change information is associated in advance with the number of similar cases that can be displayed at once in the case display area 710, and the number of similar cases that can be displayed at once in the case display area 710 may be determined by using the table. The trimmed image generator 112 may specify similar cases obtained by similar case retrieval in the descending order of similarity, and may trim the similar cases sequentially.

When the scroll bar 715 provided at the right of the case display area 710 is slid downward, the display controller 104 scrolls the case display area 710 upward in accordance with the sliding amount. Accordingly, a hidden similar case image is displayed on the display 101. In this case, the trimmed image generator 112 specifies a similar medical image to be hidden and a similar medical image to be newly displayed by using the sliding amount of the scroll bar 715 and the similarity, and may trim the similar medical image to be newly displayed. The display controller 104 may display the newly trimmed similar medical image in the case display area 710, and may delete the similar medical image specified to be hidden from the case display area 710.

The information terminal 100 of the present disclosure receives thumbnail images of a number NC of similar cases in the descending order of similarity to a retrieval query image from the case retrieval system 300, and displays thumbnail images of a number M of similar cases that can be displayed at once in the case display area 710 on the display 101 among the number NC of the received similar cases. Accordingly, a similar medical image, which is referenced when a disease name of a sick portion appearing in the retrieval query image is studied, can be efficiently extracted from a large number of medical images registered in the medical image database and can be presented to a doctor.

Also, in the present disclosure, the display number of similar medical images included in the number M of the similar medical images displayed in the case display area 710 can be changed. At this time, the display sizes of individual areas for displaying the similar medical images are changed while the display sizes of sick portions in respective similar medical images, that is, the display sizes of ROIs of thumbnail images of the respective similar cases are kept the same size. Accordingly, the display number of similar medical images included in the number M of the similar medical images displayed in the case display area 710 is changed. That is, the doctor can desirably change the display number of similar medical images displayed in the case display area 710. Consequently, viewability in a retrieval result window of the case retrieval system can be improved. This can make contribute to improvement in diagnosis accuracy.

Also, in the present disclosure, the display size of the sick portion (ROI) is kept the same size because the area that the doctor is interested in similar case retrieval is a sick portion of each similar medical image. That is, the doctor makes diagnosis on whether or not a similar medical image is similar to a target medical image (retrieval query image) mainly for a sick portion of the similar medical image. Owing to this, to keep the display size of the sick portion of each similar medical image the same size is to keep information required for diagnosis without deteriorated.

Further, to keep the display size of the sick portion the same size may be advantageous in view of diagnosis as compared with a case in which the display size of the sick portion is increased. That is, since the display size of the sick portion is kept the same size, even after the display size of each individual area is changed, the doctor can easily recognize the area of the sick portion of each similar medical image. If the display size of the sick portion is increased, the area of the sick portion of each similar medical image may not be easily recognized merely by watching the similar medical image displayed in the case display area 710. Then, when the doctor compares the target medical image with each similar medical image, the doctor may not easily determine whether or not the area of the sick portion is identical. Therefore, in this embodiment, the display size of the sick portion is kept the same size. The reason why the display size of the individual area is changed, that is, the reason why an area other than the sick portion is trimmed is that the area deleted by trimming is less important as information required for diagnosis as compared with the sick portion.

Hence, with this embodiment, information required for diagnosis can be properly presented to the doctor while viewability of the display window for displaying a retrieval result of similar case retrieval is improved. Consequently, this can contribute to improvement in diagnosis accuracy by a doctor.

Also, reducing the display sizes of the number M of individual areas for displaying the number M of the similar medical images while keeping the display sizes of the sick portions in the respective similar medical images the same size corresponds to that the area other than the sick portion of each similar medical image is deleted by trimming. In other words, the display size of each individual area is reduced by the amount of the area deleted by trimming. Then, since the display size of each individual area is reduced, the display number of similar medical images that are included in the number M of the similar medical images and that can be displayed in the case display area 710 is increased. Consequently, a similar medical image hidden from the case display area 710 when the display size of each individual area is the original size can be displayed in the case display area 710.

With this embodiment, since a similar medical image hidden from the case display area 710 when the image has the original size can be displayed, viewability of the display window that displays retrieval results of similar case retrieval by the case retrieval system 300 is improved.

Also, with this embodiment, the display number of similar medical images included in the number M of the similar medical images displayed in the case display area 710 is changed in accordance with the movement of the scroll bar 1700. Accordingly, the doctor can change the display number of similar medical images included in the number M of the similar medical images displayed in the case display area 710 by an easy operation. Accordingly, the load of operation of the doctor is decreased, the doctor can concentrate on specialized diagnosis by the amount of decreased load, and hence diagnosis accuracy can be increased.

Further, with this embodiment, the display number of similar medical images included in the number M of the similar medical images displayed in the first display area is increased in accordance with the moving distance of the scroll bar 1700. That is, the doctor can control the display number of similar medical images included in the number M of the similar medical images displayed in the case display area 710, by a simple operation of adjusting the moving distance of the scroll bar 1700. Accordingly, the load of operation of the doctor is decreased, the doctor can concentrate on specialized diagnosis by the amount of decreased load, and hence diagnosis accuracy can be increased.

First Modification

Also, in the above-described embodiment, for example, the display sizes of the respective individual areas in which thumbnail images of similar cases are displayed may be the same size in the case display area 710 as shown in FIGS. 42 and 43.

Figure 45:
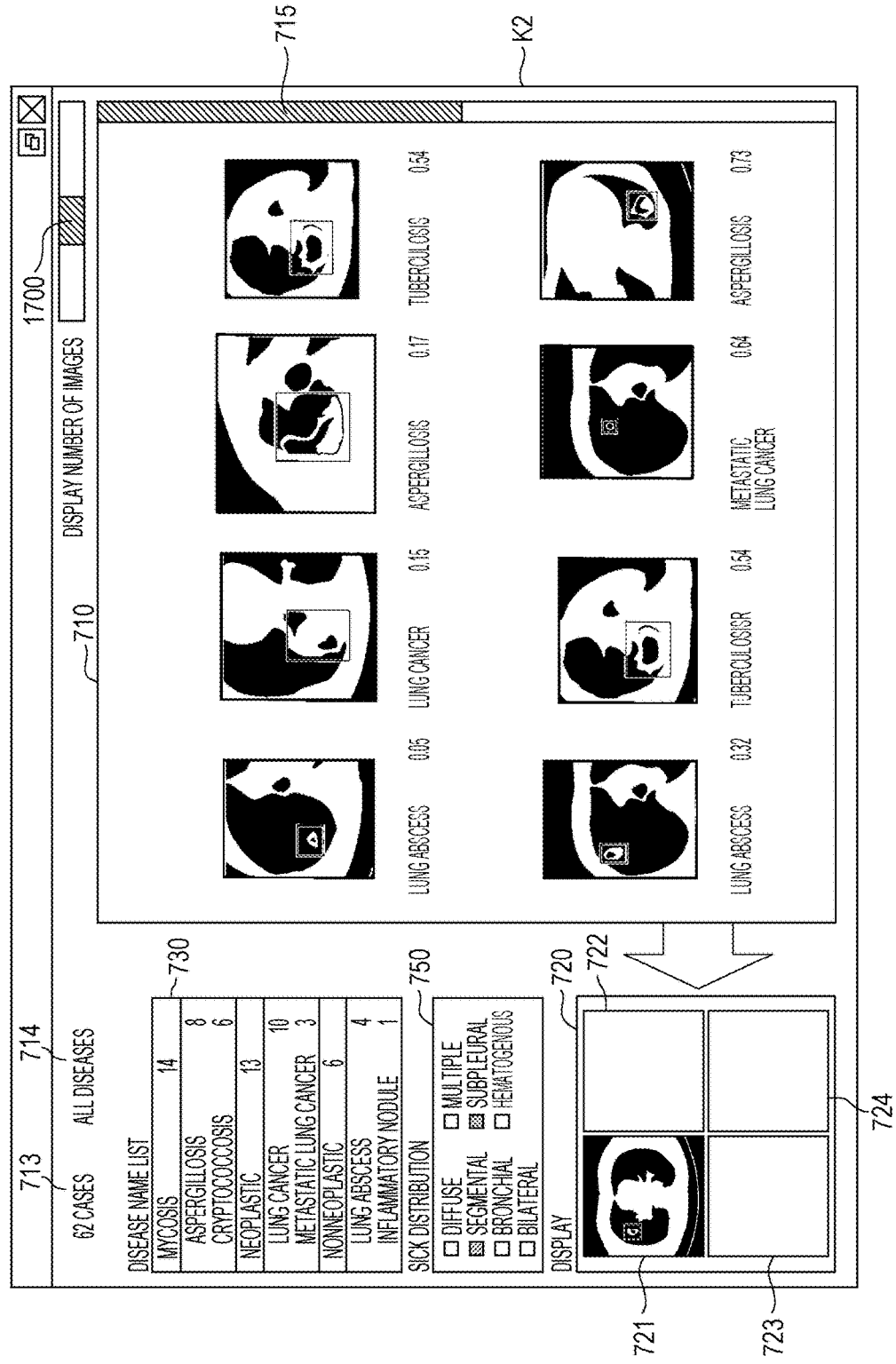
FIG. 45 illustrates an example of a basic window when similar medical images with different sizes are displayed in the case display area.

With this embodiment, in the case display area 710, since the display sizes of the respective individual areas for displaying the similar medical images are the same in the case display area 710, viewability is improved as compared with a case in which the display sizes of respective individual areas are not uniform as shown in FIG. 45.

Figure 49:
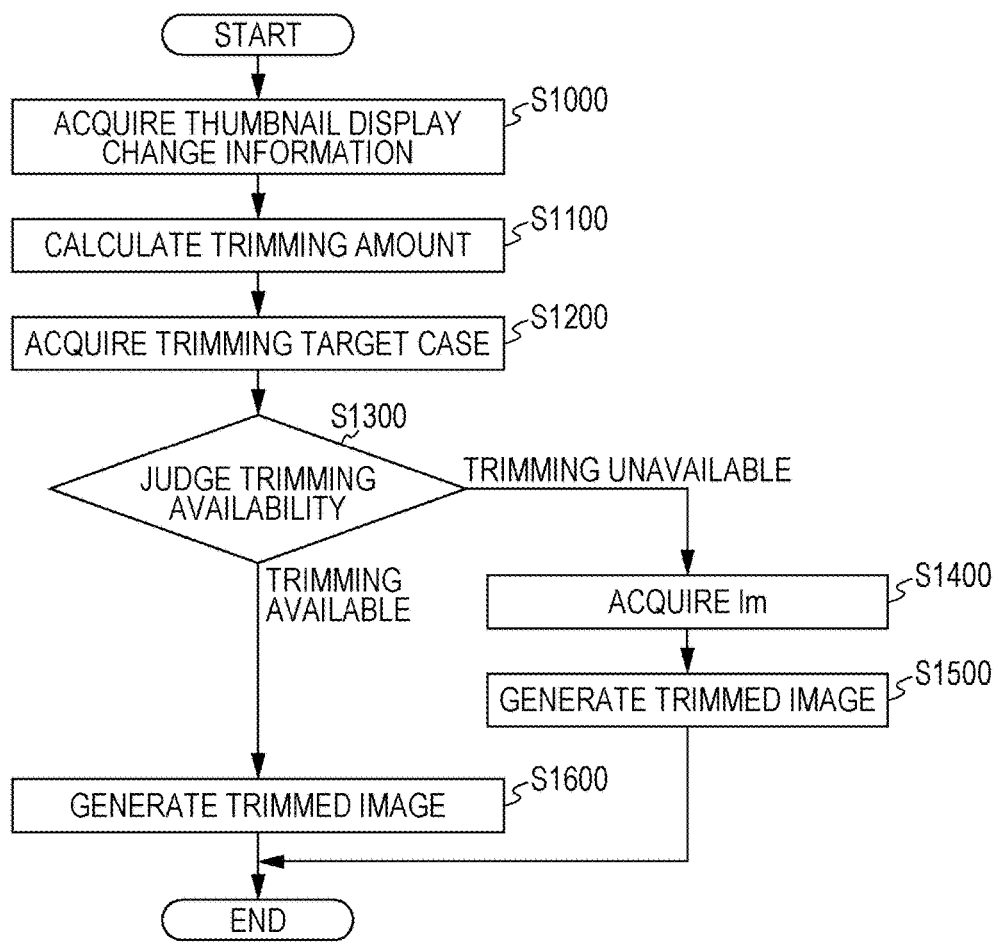
FIG. 49 is a flowchart showing a flow of processing after a similar case retrieval result is initially displayed in the information terminal until thumbnail images being the similar case retrieval result are trimmed into the same size.

FIG. 49 is a flowchart showing a flow of processing after a similar case retrieval result is initially displayed in the information terminal 100 until thumbnail images obtained by similar case retrieval are trimmed into the same size. This processing is entirely executed in the information terminal 100.

Acquire Thumbnail Display Change Information: S1000

In S1000, thumbnail display change information input by a user is acquired. The details of this processing are similar to S2000 in FIG. 53.

Acquire Enlargement Change Operation Amount: S1100

Then, in S1100, the trimmed image generator 112 calculates a trimming amount Tr of a thumbnail image in accordance with the thumbnail display change information acquired in S1000.

Figure 50:
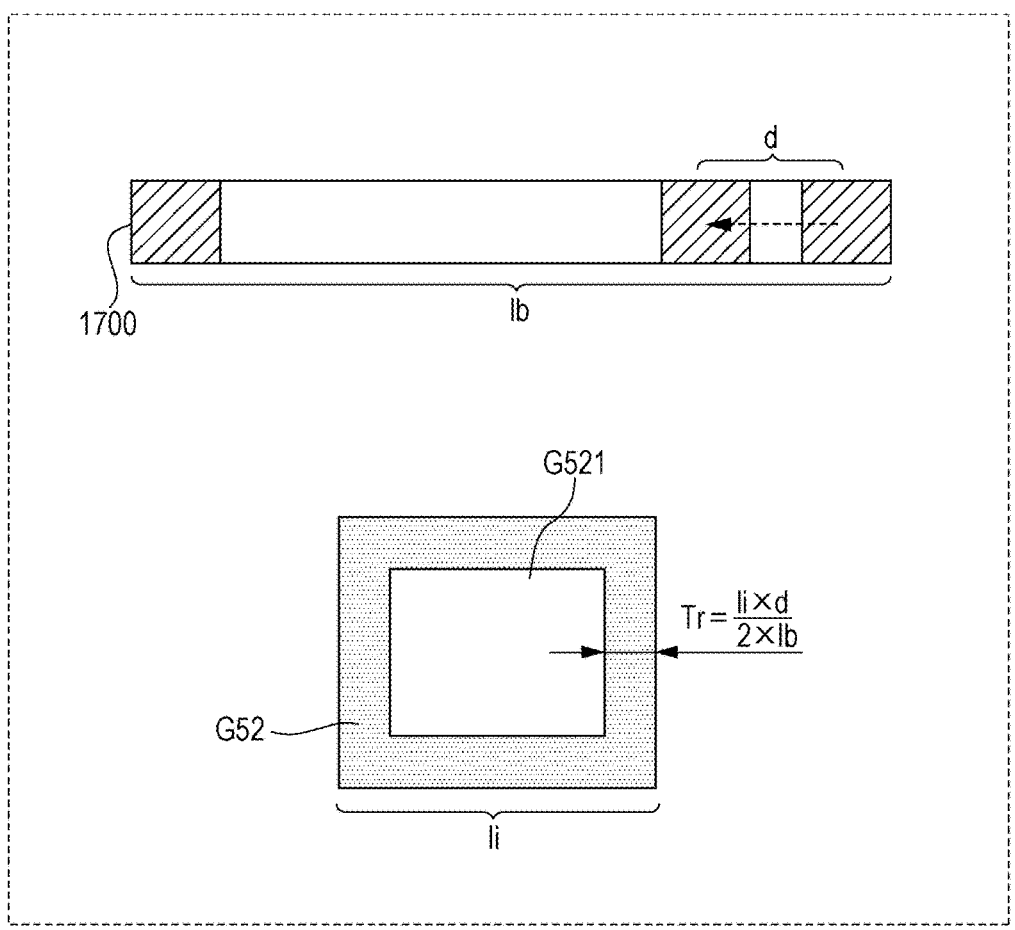
FIG. 50 illustrates processing of calculating a trimmed area.

FIG. 50 illustrates processing of calculating a trimmed area. As shown in the upper section in FIG. 50, when Ib is a total length of the scroll bar 1700, d is a moving distance of the scroll bar 1700, and Ii is an initial size of a target thumbnail image G52 for displaying, the trimming amount Tr can be calculated with the following expression. In the example in FIG. 50, it is assumed that each thumbnail image G52 displayed in the case display area 710 is a square. Also, in the example in FIG. 50, it is assumed that the scroll bar 1700 starts at the right end of the sliding allowable range and is slid leftward. Hence, the moving distance d of the scroll bar 1700 is determined by the sliding amount from the right end of the sliding allowable range to the left. The expression for the trimming amount Tr is as follows:

$$Tr = Ii \times d/2 \times Ib$$

In this case, the denominator is multiplied by 2 to determine the trimming amount Tr of each edge of the thumbnail image G52 while distributing Ii/Ib to the opposing 2 edges.

Acquire Trimming Target Case: S1200

Then, in S1200, the trimmed image generator 112 acquires target similar cases for displaying as trimming target cases among the number NC of the similar cases acquired by similar case retrieval. In this case, the target similar cases for displaying represent similar cases by a number of similar cases that can be displayed at once in the case display area 710. The details of this processing are already described in S2400 and are omitted.

Judge Trimming Availability: S1300

In S1300, the trimmed image generator 112 judges whether trimming by the trimming amount Tr is available or unavailable on the trimming target case, by using the ROI coordinates given to each trimming target case acquired in S1200 and the trimming amount Tr. If it is judged that trimming is available, the trimmed image generator 112 advances the processing to S1600. In contrast, if it is judged that trimming is unavailable, the trimmed image generator 112 advances the processing to S1400.

Figure 51:
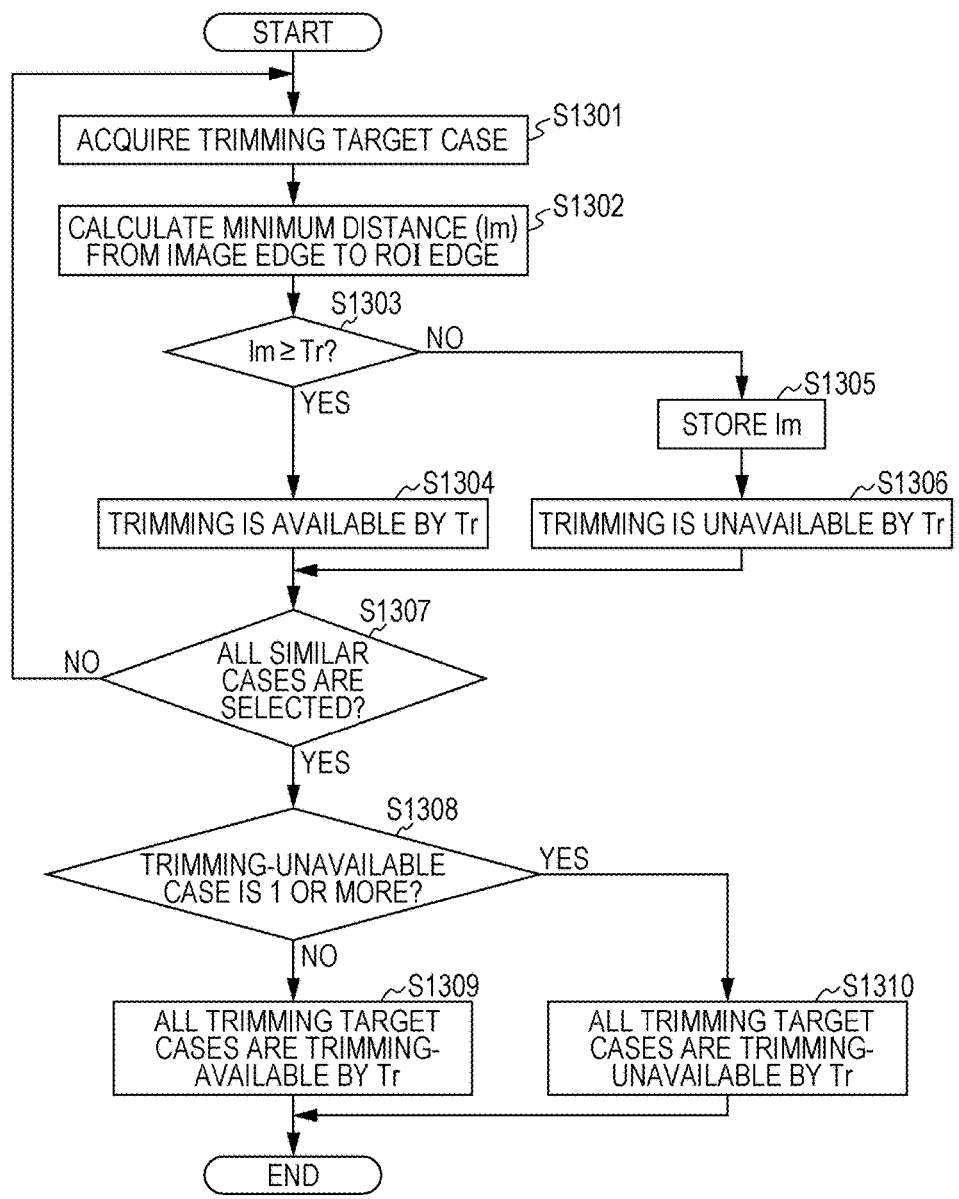
FIG. 51 is a flowchart showing the details of processing of judging whether trimming in S1300 in FIG. 49 is available or unavailable.

FIG. 51 is a flowchart showing the details of processing of judging whether trimming is available or unavailable in S1300 of FIG. 49. The judgment processing for judging trimming availability is described below with reference to FIG. 51.

In S1301, the trimmed image generator 112 acquires one trimming target case from the trimming target cases acquired in S1200 in FIG. 49. In this case, the trimmed image generator 112 may select one trimming target case from the trimming target cases acquired in S1200 in the descending order of similarity.

Then, in S1302, the trimmed image generator 112 calculates a minimum distance lm among the distances between the respective edges of the ROI and the respective edges of the thumbnail image G52 for the one trimming target case acquired in S1301.

Figure 52:
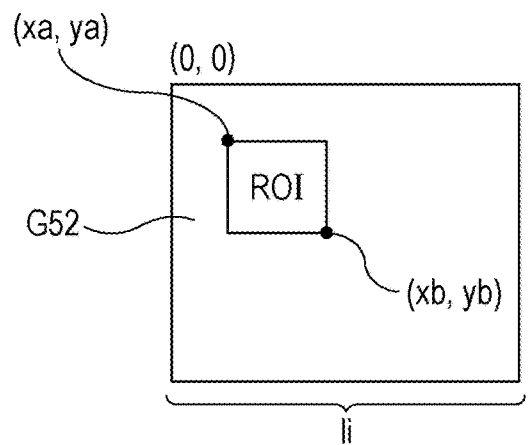
FIG. 52 is an explanatory view of the processing of judging trimming availability.

FIG. 52 is an explanatory view of the processing of judging trimming availability. As shown in FIG. 52, when the origin (0, 0) is set at the upper left apex of the thumbnail image G52, Ii represents a length of an edge of the thumbnail image G52, (xa, ya) represents coordinates of the upper left apex of the ROI, and (xb, yb) represents coordinates of the lower right apex of the ROI, the distances between the respective edges of the ROI and the respective edges of the thumbnail image G52 are calculated such that the left edge is xa, the upper edge is ya, the right edge is Ii−xb, and the lower edge is Ii−yb. Hence, the smallest value among xa, ya, Ii−xb, and Ii−yb is calculated as the minimum distance lm between the respective edges of the ROI and the respective edges of the thumbnail image G52.

Then, in S1303, the trimmed image generator 112 judges whether or not the minimum distance lm calculated in S1302 is larger than the trimming amount. If the minimum distance is equal to or larger than the trimming amount Tr (YES in S1303), the trimmed image generator 112 judges that the one trimming target case selected in S1301 is available by the trimming amount Tr (S1304). In contrast, if the minimum distance lm is smaller than the trimming amount Tr (NO in S1303), the trimmed image generator 112 stores the minimum distance lm of the one trimming target case selected in S1301 in the memory 503 (not illustrated) (S1305), and judges that trimming on the trimming target case is unavailable by the trimming amount Tr (S1306). In this case, if the minimum distance lm is already stored in the memory 503, the trimmed image generator 112 judges whether or not the minimum distance lm currently calculated is smaller than the minimum distance lm stored in the memory 503. If it is judged that the currently calculated minimum distance lm is smaller, the minimum distance lm stored in the memory 503 is updated with the currently calculated minimum distance lm.

Accordingly, if there are a plurality of trimming target cases judged as that trimming is unavailable, all the trimming target cases are trimmed by using the minimum distance lm being the smallest among the minimum distances lm of all the trimming target cases. Consequently, in all the trimming target cases, ROIs can be prevented from being trimmed, and the sizes of all the trimming target cases after trimming can be kept the same size.

In S1307, the trimmed image generator 112 judges whether or not all the similar cases obtained by similar case retrieval are selected as the trimming target cases. If the trimmed image generator 112 judges that not all the similar cases are selected (NO in S1307), the processing is returned to S1301, and the next trimming target case is selected. In contrast, if all the trimming target cases are selected (YES in S1307), the trimmed image generator 112 advances the processing to S1308.

By executing the above-described processing from S1301 to S1307, it is determined whether trimming is available or unavailable by the trimming amount Tr for each trimming target case.

In S1308, if there are at least one trimming target case judged as that trimming is unavailable among all the trimming target cases (YES in S1308), the trimmed image generator 112 judges that trimming on all the trimming target cases is unavailable by the trimming amount Tr (S1310). In this case, the judgment in S1300 in FIG. 49 is that trimming is unavailable, and the processing goes to S1400.

In contrast, if the trimming target case judged as that trimming is unavailable is 0 (NO in S1308), the trimmed image generator 112 judges that trimming is available on all trimming target cases by the trimming amount Tr (S1309). In this case, the judgment in S1300 in FIG. 49 is that trimming is available, and the processing goes to S1600.

Acquire Trimming-Available Size: S1400

Referring back to FIG. 49, in S1400, the trimmed image generator 112 reads out the minimum distance lm stored in the memory 503 in S1305 in FIG. 51, and acquires the minimum distance lm.

Generate Trimmed Image: S1500

In S1500, the trimmed image generator 112 executes trimming on the respective thumbnail images of all trimming target cases by using the minimum distance lm acquired in S1400 in FIG. 51.

To be specific, as shown in the lower section in FIG. 50, the area (the area with gray color) by the trimming amount Tr (in this case, the minimum distance Tr) from each respective edge is deleted from the thumbnail image G52 of each trimming target case.

To be more specific, the upper edge of the trimmed area G521 is set at a position separated downward from the upper edge of the thumbnail image G52 by the trimming amount Tr, the left edge of the trimmed area G521 is set at a position separated rightward from the left edge of the thumbnail image G52 by the trimming amount Tr, the right edge of the trimmed area G521 is set at a position separated leftward from the right edge of the thumbnail image G52 by the trimming amount Tr, and the lower edge of the trimmed area G521 is set at a position separated upward from the lower edge of the thumbnail image G52 by the trimming amount Tr. A frame-shaped area (the area with gray color) between the trimmed area G521 and the thumbnail image G52 is deleted from the thumbnail image G52, and thus the thumbnail image G52 is trimmed.

In this way, in S1500, if there is at least one trimming target case judged as that trimming is unavailable, all the trimming target cases are trimmed by using the minimum distance lm that is the smallest among the minimum distances lm of all the trimming target cases as the trimming amount Tr. In this case, for example, if the trimming target case is trimmed by using a minimum distance lm that is the second to the smallest minimum distance lm among the trimming target cases, part of ROI in the trimming target case with the smallest minimum distance lm may be trimmed. In the present disclosure, since the respective trimming target cases are trimmed by using the smallest minimum distance lm as the trimming amount Tr, ROIs of all trimming target cases can be prevented from being deleted, and all trimming target cases after trimming can be kept the same size.

Generate Trimmed Image: S1600

In S1600, since it is judged that trimming is available for all the trimming target cases in S1309 (FIG. 51) by using the trimming amount Tr calculated in S1100, the trimmed image generator 112 executes trimming on each thumbnail image of the trimming target case by using the trimming amount Tr calculated in S1100. The details of the processing in S1600 is the same as S1500. In this case, the respective thumbnail images of all the trimming target cases are uniformly trimmed by using the trimming amount Tr, and hence the sizes of the trimming target cases after trimming become the same size.

By executing the above-described processing from S1000 to S1600, the display sizes of the thumbnail images to be displayed in the case display area 710 can be the same as shown in FIGS. 43 and 44. Then, the display controller 104 arranges the trimmed trimming target cases in the descending order of similarity in the case display area 710, and displays the trimming target cases on the display 101. The details of this processing are already described in S2400 in FIG. 53 and are omitted.

FIG. 45 illustrates an example of a basic window K2 when similar medical images are displayed in the case display area 710 with different sizes. In FIG. 45, the respective similar medical images are trimmed by using the method shown in FIG. 55, and the trimmed similar medical images are displayed in 2 rows by 4 columns in the case display area 710 in the descending order of similarity.

With the method shown in FIG. 55, the trimming amount Tr is calculated by multiplying each of distances (lp, lq, lr, ls) between the edges of ROI and the edges of a thumbnail image by the trimming ratio Rt. Since the size of ROI is different depending on the thumbnail image G52, the distances of each of the edges (lp, lq, lr, ls) is different depending on the thumbnail image G52. Hence, when the method shown in FIG. 55 is employed, as shown in FIG. 45, the respective similar medical images may not be displayed with the same size in the case display area 710.

In contrast, with the method shown in the flowchart in FIG. 49, the areas of the number NC of the similar cases obtained by similar case retrieval other than ROIs are trimmed, and hence, the respective similar medical images to be displayed in the case display area 710 can be displayed with the same size.

Second Modification

In the above-described embodiment, the retrieval query image (the target medical image) and the thumbnail images of the similar cases (the similar medical images) are medical images captured by tomography. The tomography method may employ magnetic resonance imaging (MRI) or computed tomography (CT). Also, each of the similar medical images includes imaging condition information indicative of an imaging condition by MRI or CT. The display controller 104 may classify the number M of the similar medical images displayed in the case display area 710 among the number NC of the similar medical images obtained by similar case retrieval, by imaging condition, and display similar medical images.

Figure 46:
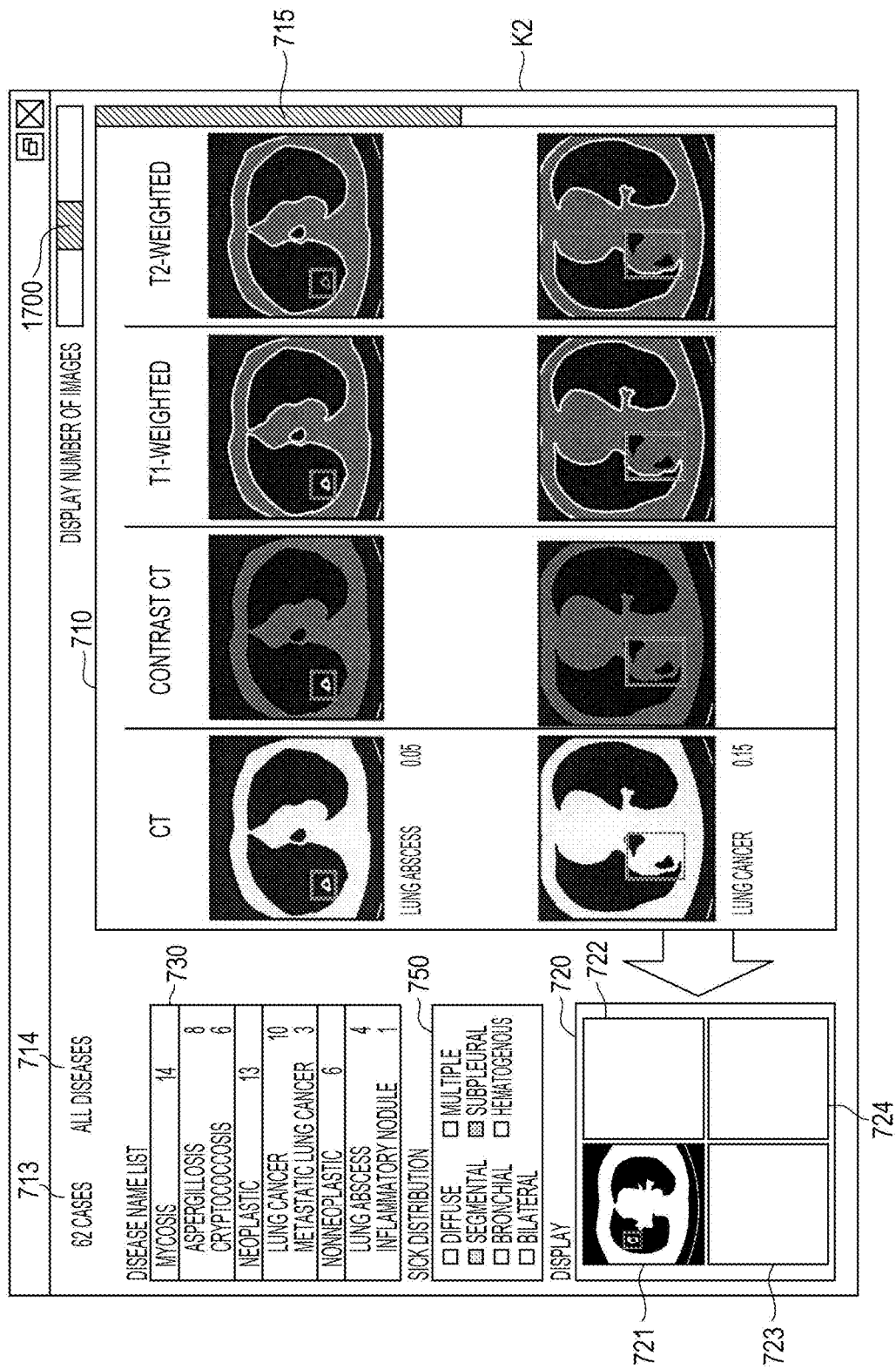
FIG. 46 illustrates an example of a case display area in which similar medical images are classified by imaging condition and displayed.

FIG. 46 illustrates an example of a case display area 710 in which similar medical images are classified and displayed by imaging condition. In this example, target similar medical images for displaying are captured under 4 different imaging conditions. The respective similar medical images are classified and displayed by 4 imaging conditions. In this case, the imaging conditions employ 4 imaging conditions including plain CT, contrast CT, T1-weighted MRI, and T2-weighted MRI.

As shown in FIG. 20, in the similar case data 4000, branch numbers are added next to underbars of the slice ID 4200, such as CT149391025_1, CT149391025_2, . . . . In this case, as described with reference to FIG. 18, the branch numbers are associated with imaging conditions in advance. For example, "1" represents plain CT, "2" represents contrast CT, "3" represents T1-weighted, and "4" represents T2-weighted. Hence, when the display controller 104 references the branch number, the display controller 104 can obtain a similar medical image captured under the imaging condition corresponding to the branch number. The branch number corresponds to an example of imaging condition information. That is, the branch number "1" indicates imaging condition information of plain CT, the branch number "2" indicates imaging condition information of contrast CT, the branch number "3" indicates imaging condition information of T1-weighted, and the branch number "4" indicates imaging condition information of T2-weighted.

A T1-weighted image is an image in which fat etc. appears white and blood etc. appears black. In contrast, a T2-weighted image is an image in which fat, blood, etc. appear white and calcification etc. appears black. That is, a target appearing white is different depending on whether the image is the T1-weighted image or the T2-weighted image. Hence, when the number M of the similar medical images are displayed in the case display area 710, if the T1-weighted image or the T2-weighted image is displayed in a mixed manner, the doctor may be confused.

With this embodiment, the number M of the similar medical images are classified and displayed in the case display area 710 by imaging condition. Accordingly, the doctor who performs diagnosis can recognize the imaging condition of each similar medical image at a glance, and the doctor can perform diagnosis without being confused. Further, since similar case determination can be held by imaging condition, diagnosis accuracy can be increased.

Third Modification

Also, in the above-described embodiment, for example, a related similar medical image with a different imaging condition is added to a similar medical image for the same imaging target. In the case display area 710, respective similar medical images and related similar medical images of the respective similar medical images may be classified and displayed by imaging condition in the same column direction (vertical direction) or the same row direction (horizontal direction).

In this case, when imaging is performed on a patient by magnetic resonance imaging, imaging may be performed under a plurality of imaging conditions in one-time imaging. That is, a plurality of similar medical images may be obtained in one-time imaging. If one of the plurality of obtained similar medical images serves as a similar medical image, the other similar medical images serve as related similar medical images. Information which cannot be obtained from the similar medical image can be obtained from the related similar medical images. This information is useful when similar cases of the retrieval query image are studied.

FIG. 46 illustrates an example in which respective similar medical images and related similar medical images of the respective similar medical images are classified and displayed by imaging condition in the same column direction (vertical direction). In FIG. 46, the case display area 710 is divided into 4 columns. Plain CT images are displayed in the 1st column to the left with a heading of "CT." Contrast CT images are displayed in the 2nd column to the left with a heading of "contrast CT." T1-weighted images are displayed in the 3rd column to the left with a heading of "T1-weighted." T2-weighted images are displayed in the 4th column to the left with a heading of "T2-weighted." When the plain CT images displayed in the 1st column serve as similar medical images, the contrast CT images, T1-weighted images, and T2-weighted images displayed in the 2nd to 4th columns serve as related similar medical images. However, this is merely an example. Medical images under an imaging condition other than plain CT image may serve as similar medical images, and similar medical images under the other 3 imaging conditions may serve as related similar medical images.

Also, in the example in FIG. 46, in the case display area 710, similar medical images of lung abscess are displayed in the 1st row, and similar medical images of lung cancer are displayed in the 2nd row. In this way, in the example in FIG. 46, the respective similar cases are classified into 4 imaging conditions and arranged in the column direction (vertical direction). Also, in the example in FIG. 46, the similar medical images and the related similar medical images are arranged so that similar medical images with higher similarities are positioned in rows closer to the top. Accordingly, the doctor can recognize at a glance that the similar medical images and the related similar medical images positioned in rows closer to the top have higher similarities to the retrieval query image.

In this case, the similar cases with higher similarities to the retrieval query image are positioned in rows closer to the top. However, this is merely an example. Alternatively, similar medical images with higher similarities to the retrieval query image may be positioned in rows closer to the bottoms.

A scroll bar 715 being long in the vertical direction is arranged at the right of the case display area 710. When the scroll bar 715 is slid downward, the case display area 710 is scrolled upward, and hidden similar medical images and related similar medical images are displayed. In the example in FIG. 46, similar cases are displayed by only 2 rows at once in the case display area 710. Hence, by sliding the scroll bar 715 downward, similar cases with 3rd or later similarities to the retrieval query image are displayed in the case display area 710.

The case display area 710 is divided in the order of plain CT, contrast CT, T1-weighted, and T2-weighted from the 1st column to the 4th column. However, this is merely an example, and the imaging conditions may be divided in another order.

Figure 47:
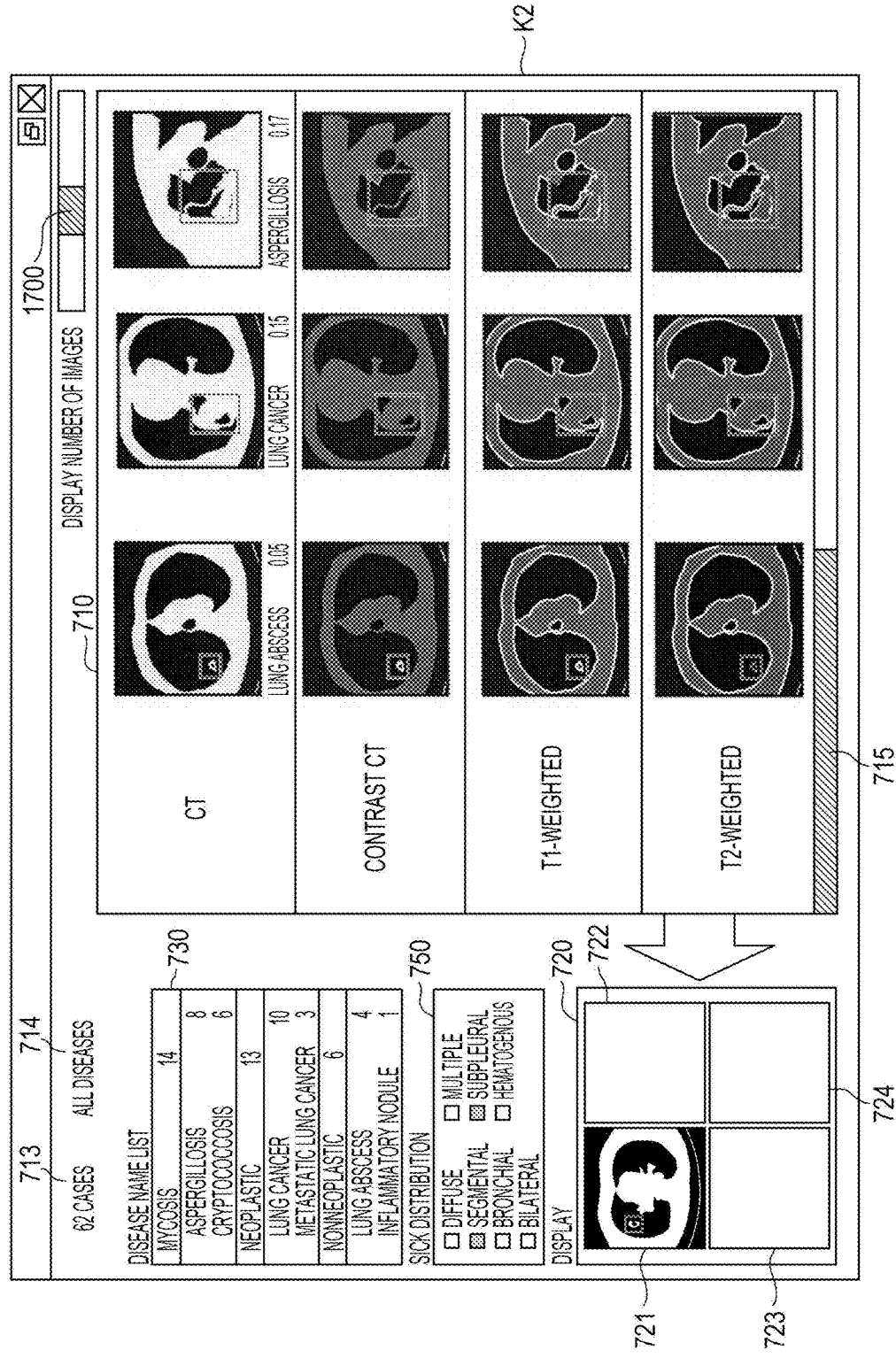
FIG. 47 illustrates an example of a case display area in which similar medical images and related similar medical images of the similar medical images are displayed in the same column direction (vertical direction) by imaging condition.

FIG. 47 illustrates an example of a case display area 710 in which respective similar medical images and related similar medical images of the respective similar medical images are displayed in the same row direction (horizontal direction) by imaging condition.

Also, in FIG. 47, the case display area 710 is divided into 4 rows. Plain CT images are displayed in the 1st row to the top with a heading of "CT." Contrast CT images are displayed in the 2nd row to the top with a heading of "contrast CT." T1-weighted images are displayed in the 3rd row to the top with a heading of "T1-weighted." T2-weighted images are displayed in the 4th row to the top with a heading of "T2-weighted." When it is assumed that the plain CT images displayed in the 1st row serve as similar medical images, the contrast CT images, T1-weighted images, and T2-weighted images displayed in the 2nd to 4th rows serve as related similar medical images. However, this is merely an example.

Also, in the example in FIG. 47, in the case display area 710, similar cases of lung abscess are displayed in the 1st column, similar cases of lung cancer are displayed in the 2nd column, and similar cases of aspergillosis are displayed in the 3rd column. In this way, in the example in FIG. 47, the respective similar cases are classified into 4 imaging conditions and arranged in the row direction (horizontal direction). Also, in the example in FIG. 47, the similar medical cases are arranged so that similar medical images with higher similarities are positioned in columns closer to the left. Accordingly, the doctor can recognize at a glance that similar medical images positioned in columns closer to the left have higher similarities to the retrieval query image.

In this case, the similar medical images with higher similarities to the retrieval query image are positioned in columns closer to the left. However, this is merely an example. Alternatively, similar medical images with higher similarities to the retrieval query image may be positioned in columns closer to the right.

A scroll bar 715 being long in the horizontal direction is arranged below the case display area 710. When the scroll bar 715 is slid rightward, the case display area 710 is scrolled leftward, and hidden similar medical images are displayed. In the example in FIG. 47, similar medical images are displayed by only 3 columns at once in the case display area 710. Hence, by sliding the scroll bar 715 rightward, similar medical images with 4th or later similarities to the retrieval query image are displayed in the case display area 710.

In the case display area 710, similar medical images are displayed in the order of plain CT images, contrast CT images, T1-weighted images, and T2-weighted images from the 1st row to the 4th row; however, this is merely an example, and similar medical images may be displayed in any of other orders.

With this embodiment, when the respective similar medical images displayed in the case display area 710 are determined whether or not being similar to the retrieval query image, the study can be held also by using the related similar medical images. Accordingly, diagnosis accuracy can be increased.

Fourth Modification

Also, in the above-described embodiment, for example, when the number NC of the similar medical images received from the case retrieval system are displayed in the case display area 710, the display sizes of the sick portions of the respective similar medical images are kept the same size and the display sizes of the individual areas for displaying the respective similar medical images are changed in accordance with the number of imaging conditions included in the number NC of the received similar medical images. In addition, the respective similar medical images and the related similar medical images of the respective similar medical images may be classified and displayed in the same column direction or the same row direction by imaging condition.

Figure 48:
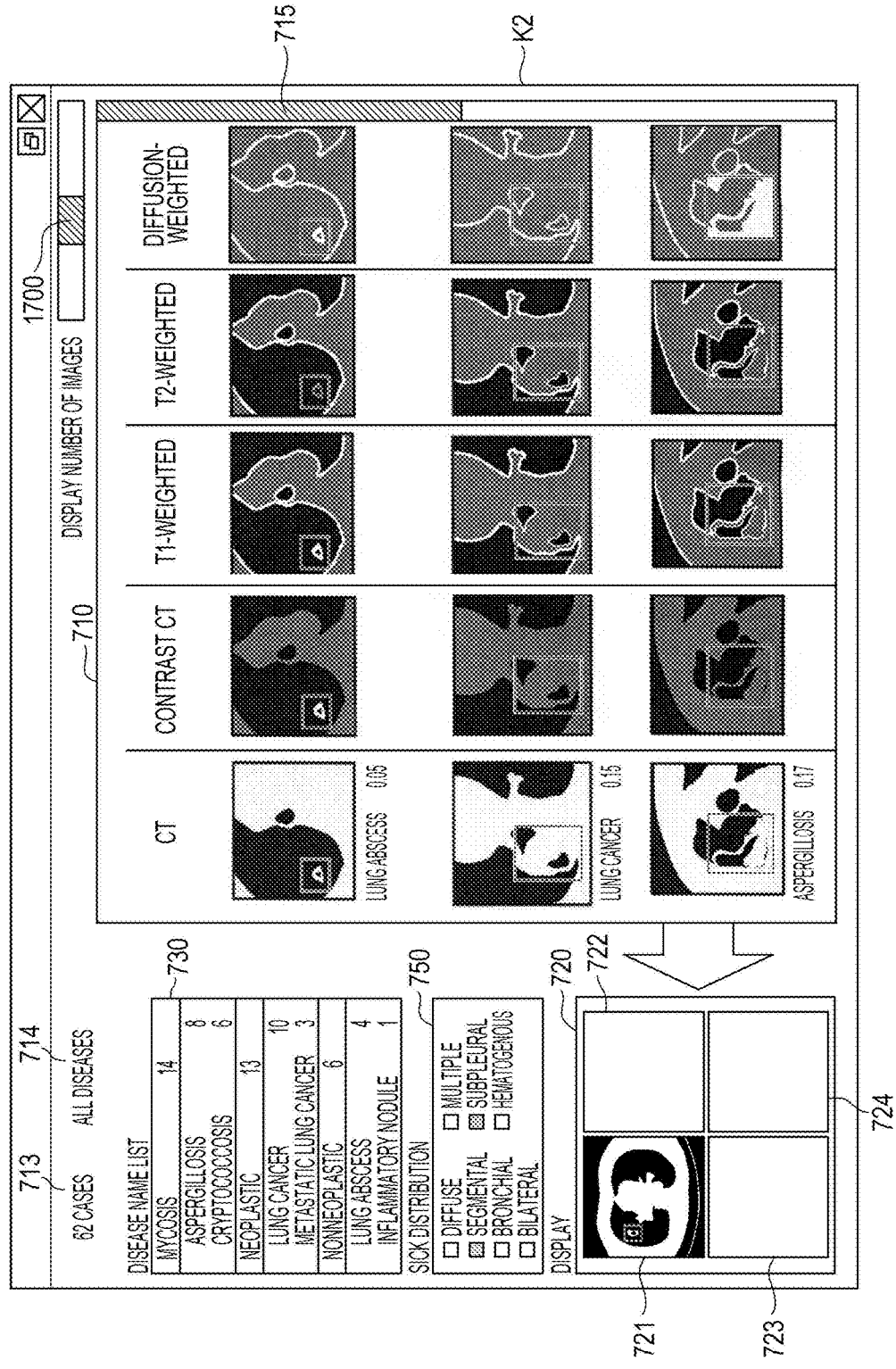
FIG. 48 illustrates an example of a case display area when a number NC of received similar medical images are captured by 5 imaging conditions (plain CT, contrast CT, T1-weighted of MRI, T2-weighted of MRI, diffusion-weighted)

FIG. 48 illustrates an example of a case display area 710 in which the number NC of the received similar medical images are captured by 5 imaging conditions (plain CT, contrast CT, T1-weighted of MRI, T2-weighted of MRI, diffusion-weighted). In FIG. 48, the trimming amount Tr of each thumbnail image to be displayed in the case display area 710 is increased by the amount of increase in the number of imaging conditions by 1 as compared with FIG. 46, the image size of the thumbnail images is reduced, and the thumbnail images are listed.

In the example in FIG. 48, the case display area 710 is divided into 5 columns, Plain CT images are displayed in the 1st column to the left with a heading of "CT." Contrast CT images are displayed in the 2nd column to the left with a heading of "contrast CT." T1-weighted images are displayed in the 3rd column to the left with a heading of "T1-weighted." T2-weighted images are displayed in the 4th column to the left with a heading of "T2-weighted." Diffusion-weighted images are displayed in the 5th column to the left with a heading of "diffusion-weighted." Also, in the example in FIG. 48, similar cases of lung abscess are displayed in the 1st row, similar cases of lung cancer are displayed in the 2nd row, and similar cases of aspergillosis are displayed in the 3rd row. In this way, in the example in FIG. 48, the respective similar cases are classified into 5 imaging conditions and arranged in the column direction (vertical direction). Also, in the example in FIG. 48, the similar cases are arranged so that similar medical images with higher similarities are positioned in rows closer to the top. Accordingly, the doctor can recognize at a glance that similar cases positioned in rows closer to the top have higher similarities to the retrieval query image.

In FIG. 48, since the number NC of the received similar medical images are captured under 5 imaging conditions, the case display area 710 are divided into 5 columns. However, similar medical images may be captured under a number i of imaging conditions, i being 2 or larger and 4 or smaller, or 6 or larger. In this case, the display controller 104 may divide the case display area 710 into the number i of columns. Also, the number of imaging conditions for the number NC of the acquired similar medical images may be different. In this case, the case display area 710 may be divided by the maximum number of imaging conditions in the number NC of the acquired similar medical images. For example, if the maximum number of imaging conditions is 5 in the number NC of the acquired similar medical images, the display controller 104 may divide the case display area 710 into 5.

In this case, for similar medical images under 4 or less imaging conditions, the display controller 104 may display a display area (individual area) for a similar medical image corresponding to a lacking imaging condition as a blank area. For example, in the example in FIG. 48, if lung cancer is not captured under the imaging condition of "contrast CT," the display area of "contrast CT" is blank. In this case, for example, a blank display form may be that the corresponding display area (individual area) is displayed in a predetermined color (for example, black or white).

In FIG. 48, the case display area 710 is divided into 5 columns. Alternatively, the case display area 710 may be divided into 5 rows similarly to the example in FIG. 47. In this case, the display controller 104 may display similar cases with higher similarities in columns closer to the left similarly to the example in FIG. 47.

Then, processing of generating the case display area 710 in FIG. 48 is described. The display controller 104 detects the maximum number of imaging conditions of the number NC of the acquired similar cases. In this case, the display controller 104 may detect the maximum number of imaging conditions by using the branch numbers in the slice ID 4200 of the similar case data 4000 respectively corresponding to the number NC of the similar cases.

Then, the display controller 104 specifies the display layout of the case display area 710 corresponding to the detected maximum number of imaging conditions. In this case, it is assumed that the display layout of the case display area 710 is previously determined in accordance with the maximum number of imaging conditions and the thumbnail display change information. In the example in FIG. 48, the case display area 710 employs a display layout divided into 3 rows by 5 columns by imaging condition. The display layout is determined based on the maximum number of imaging conditions (in this case, 5) and the thumbnail display change information.

The trimmed image generator 112 trims similar cases by the number indicated by the specified display layout. At this time, the trimmed image generator 112 may trim areas other than ROIs set in the similar cases. In this case, the trimmed image generator 112 may trim, for example, the thumbnail image G52 of the similar case by using the method illustrated in the lower section of FIG. 50. In this case, the trimmed image generator 112 shifts the 4 boundary lines defining the boundary of the trimmed area G521 toward the center from the 4 edges of the thumbnail image G52 by the trimming amount Tr. It is assumed that certain one of the 4 boundary lines reaches the edge of ROI. In this case, the trimmed image generator 112 may stop the movement of the boundary line, and may shift the residual boundary lines toward the center of the thumbnail image G52 until the total value of the moving amounts of the opposing boundary lines becomes 2×trimming amount Tr. Then, the trimmed image generator 112 trims the area outside the 4 boundary lines. Accordingly, the size of the thumbnail image G52 after trimming can be kept the same size while the size of ROI is kept unchanged.

The trimmed image generator 112 executes such trimming processing on the similar cases by the number of cases that can be displayed at once in the case display area 710. Then, the display controller 104 displays similar medical images and related similar medical images of all the trimmed similar cases in the descending order of similarity.

With this embodiment, the case display area 710 is divided in accordance with the number of imaging conditions of the number NC of the similar medical images received from the case retrieval system 300. The size of ROIs is kept unchanged, the similar medical images are trimmed to have the display size previously determined in accordance with the number of imaging conditions, and the trimmed similar medical images are displayed in the case display area 710.

That is, in the window of initial retrieval results, the above-described display window is displayed without any operation by the doctor. Accordingly, the load of operation of the doctor is decreased, the doctor can concentrate on specialized diagnosis by the amount of decreased load, and hence diagnosis accuracy can be increased.

Fifth Modification

In S1400 in FIG. 49, the similar medical images are trimmed by using the smallest value of the minimum distance lm. However, the present disclosure is not limited thereto. In the example in FIG. 50, the trimmed image generator 112 shifts the 4 boundary lines defining the boundary of the trimmed area G521 toward the center from the 4 edges of the thumbnail image G52 by the trimming amount Tr. In this case, if certain one of the 4 boundary lines reaches the edge of ROI, the movement of the boundary line may be stopped, and the residual boundary lines may be shifted toward the center of the thumbnail image G52 until the total value of the moving amounts of the opposing boundary lines become 2×trimming amount Tr. Then, the trimmed image generator 112 trims the area outside the 4 boundary lines. Accordingly, the display size of the thumbnail image G52 after trimming can be kept the same size while the display size of ROI is kept unchanged.

Sixth Modification

In the above description, the trimmed image generator 112 executes trimming on the similar cases that can be displayed at once in the case display area 710. However, the trimmed image generator 112 may execute trimming on all the number NC of the similar cases. In this case, when the scroll bar 715 is slid and hidden similar cases are displayed, the necessity of executing trimming on the hidden similar cases is omitted. Hence, the processing can be increased in speed.

The present disclosure can be used for a similar case retrieval apparatus that presents a similar case which is referenced when diagnosis is made with use of a target medical image for reading, and for a reading training apparatus for a trainee radiologist.

What is claimed is:

1. A control method of an information terminal connected to a case retrieval system that retrieves a medical image by referencing a medical image database in which the medical image is registered, the information terminal including a display, the method comprising:
   receiving, via a computer of the information terminal, a number NC, being 2 or larger, of similar medical images each having predetermined similarity to a target medical image, being a target medical image for reading, from the case retrieval system, each of the number NC of the similar medical images including sick portion information indicative of a sick portion in the similar medical image;
   causing the display to show a display window including a first display area including a number M, being in a range from 1 to the number NC, of individual areas displaying the number M of the similar medical images included in the number NC of the similar medical images, and causing an instruction function to change a display number of the similar medical images included in the number M of the similar medical images displayed in the first display area; and
   detecting an instruction by the instruction function,
   wherein if the instruction by the instruction function is detected in the detecting, changing a display size of each of the individual areas while keeping a display size of the sick portion of each of the similar medical images a same size, and hence changing the display number of the similar medical images included in the number M of the similar medical images displayed in the first display area, and
   if the instruction by the instruction function detected in the detecting is an instruction to increase the display number of the similar medical images, reducing the display size of each of the individual areas while keeping the display size of the sick portion of each of the similar medical images the same size, and hence the display number of the similar medical images included in the number M of the similar medical images displayed in the first display area is increased.

2. The control method according to claim 1,
   wherein the instruction function is a scroll bar, and
   wherein, if movement of the scroll bar is detected, the display size of each of the individual areas is changed while the display size of the sick portion of each of the similar medical images is kept the same size, and hence the display number of the similar medical images included in the number M of the similar medical images displayed in the first display area is changed.

3. The control method according to claim 2, wherein, if the instruction to increase the display number of the similar medical images by the scroll bar is detected, the display size of each of the individual areas is reduced as a moving distance of the scroll bar is increased.

4. The control method according to claim 1, wherein the display sizes of the individual areas displayed in the first display area are identical.

5. The control method according to claim 1,
   wherein the target medical image and the similar medical images are medical images captured by tomography,
   wherein each of the similar medical images includes imaging condition information indicative of an imaging condition of the tomography, and
   wherein the number M of the similar medical images are classified by the imaging condition based on the imaging condition information and displayed in the first display area.

6. The control method according to claim 5,
   wherein related similar medical images are added to the similar medical images, the related similar medical images each having an imaging condition different from the imaging condition of each of the similar medical images for a same imaging target, and
   wherein the similar medical images and the related similar medical images of the similar medical images are classified in a same column direction or a same row direction by the imaging condition and displayed in the first display area.

7. The control method according to claim 6,
   wherein, when the number NC of the similar medical images received from the case retrieval system are displayed in the first display area,
   the display size of each of the individual areas is changed while the display size of the sick portion of each of the similar medical images is kept the same size in accordance with a total number of imaging conditions included in the number NC of the received similar medical images, and
   the similar medical images and the related similar medical images of the similar medical images are classified and displayed in the same column direction or the same row direction by the imaging condition.

8. The control method according to claim 1,
   wherein the control method has the computer of the information terminal detect designation information indicative of a region of interest in the target medical image,
   transmit information indicative of a feature amount of the region of interest to the case retrieval system, and
   receive the feature amount of the region of interest and a similar medical image having the predetermined similarity from the case retrieval system.

9. The control method according to claim 1,
   wherein the control method has the computer of the information terminal
   detect designation information indicative of a region of interest in the target medical image,
   transmit the target medical image and the designation information to the case retrieval system, and
   receive a feature amount of the region of interest obtained from the target medical image and the designation information, and a similar medical image having the predetermined similarity from the case retrieval system.

10. A non-transitory computer-readable recording medium including a program causing processing to be executed in an information terminal connected to a case retrieval system that retrieves a medical image by referencing a medical image database in which the medical image is registered, the information terminal including a display and a processor, wherein the non-transitory computer-readable recording medium is non-volatile,
wherein a computer of the information terminal is capable of reading data from the non-transitory computer-readable recording medium, and
wherein the computer, via processing;
receives a number NC, being 2 or larger, of similar medical images each having predetermined similarity to a target medical image, being a target medical image for reading, from the case retrieval system, each of the number NC of the similar medical images including sick portion information indicative of a sick portion in the similar medical image;
causes the display to show a display window including a first display area including a number M, being in a range from 1 to the number NC, of individual areas displaying the number M of the similar medical images included in the number NC of the similar medical images, and causes an instruction function to change a display number of the similar medical images included in the number M of the similar medical images displayed in the first display area; and
detects an instruction by the instruction function,
wherein if the instruction by the instruction function is detected in the detecting, the computer, via the processing, changes a display size of each of the individual areas while keeping a display size of a sick portion of each of the similar medical images a same size, and hence changing the display number of the similar medical images included in the number M of the similar medical images displayed in the first display area, and
if the instruction by the instruction function detected in the detecting is an instruction to increase the display number of the similar medical images, the computer, via the processing, reduces the display size of each of the individual areas while the display size of the sick portion of each of the similar medical images is kept the same size, and hence the display number of the similar medical images included in the number M of the similar medical images displayed in the first display area is increased.

11. A control method, comprising:
receiving, via an information terminal, first thumbnail images including second thumbnail images and third thumbnail images, each of the first thumbnail images including a sick portion, similar images each having predetermined similarity to a target medical image for reading, the similar images and the first thumbnail images being in a one-to-one relationship, each of the first thumbnail images being generated based on the corresponding similar image included in the similar images;
causing a display to display first images in a predetermined area, the first images and the second thumbnail images being in a one-to-one relationship, each of the first images being generated based on the corresponding thumbnail image included in the second thumbnail images;
receiving an instruction to increase a total number of images displayed in the predetermined area from a total number of the first images; and
causing the display to display second images and third images in the predetermined area after receiving the instruction, wherein the second images and the second thumbnail images are in a one to-one relationship, and the third images and the third thumbnail images are in a one-to-one relationship,
wherein each of the second images is generated based on the corresponding thumbnail image included in the second thumbnail images, and each of the third images is generated based on the corresponding thumbnail image included in the third thumbnail images, and
wherein, if a first image included in the first images and a second image included in the second images are generated based on a same thumbnail image included in the second thumbnail images, an area of the first image is larger than an area of the second image, and an area of a sick portion included in the first image and an area of a sick portion included in the second image are identical.

12. The control method according to claim 11, further comprising:
when the first images are displayed in the predetermined area, dividing the predetermined area into areas, a total number of which is identical to the total number of the first images; and
when the second images and the third images are displayed in the predetermined area, dividing the predetermined area into areas, a total number of which is identical to a total number of the second images and the third images.

13. A control method of an information terminal connected to a case retrieval system that retrieves a medical image by referencing a medical image database in which the medical image is registered, the information terminal including a display, the method comprising:
receiving, via a computer of the information terminal, a number NC, being 2 or larger, of similar medical images each having predetermined similarity to a target medical image, being a target medical image for reading, from the case retrieval system, each of the number NC of the similar medical images including sick portion information indicative of a sick portion in the similar medical image;
causing the display to show a display window including a first display area including a number M, being in a range from 1 to the number NC, of individual areas displaying the number M of the similar medical images included in the number NC of the similar medical images, and causing an instruction function to change a display number of the similar medical images included in the number M of the similar medical images displayed in the first display area; and
detecting an instruction by the instruction function,
wherein the instruction function is a scroll bar,
if the instruction by the scroll bar is detected in the detecting, changing a display size of each of the individual areas while keeping a display size of the sick portion of each of the similar medical images a same size, and hence changing the display number of the similar medical images included in the number M of the similar medical images displayed in the first display area, and
if movement of the scroll bar is detected in the detecting, changing the display size of each of the individual areas while keeping the display size of the sick portion of each of the similar medical images the same size, and hence the display number of the similar medical images included in the number M of the similar medical images displayed in the first display area is changed.

\* \* \* \* \*